(12) United States Patent
Konnai et al.

(10) Patent No.: US 11,198,730 B2
(45) Date of Patent: Dec. 14, 2021

(54) ANTI-LAG-3 ANTIBODY

(71) Applicants: National University Corporation Hokkaido University, Hokkaido (JP); Fuso Pharmaceutical Industries, Ltd., Osaka (JP)

(72) Inventors: Satoru Konnai, Hokkaido (JP); Kazuhiko Ohashi, Hokkaido (JP); Shiro Murata, Hokkaido (JP); Tomohiro Okagawa, Hokkaido (JP); Asami Nishimori, Hokkaido (JP); Naoya Maekawa, Hokkaido (JP); Yasuhiko Suzuki, Hokkaido (JP); Chie Nakajima, Hokkaido (JP)

(73) Assignees: Fuso Pharmaceutical Industries, Ltd., Osaka (JP); National University Corporation Hokkaido University, Hokkaido (JP)

( * ) Notice: Subject to any disclaimer, the term of this patent is extended or adjusted under 35 U.S.C. 154(b) by 332 days.

(21) Appl. No.: 16/325,150

(22) PCT Filed: Aug. 10, 2017

(86) PCT No.: PCT/JP2017/029057
§ 371 (c)(1),
(2) Date: Feb. 12, 2019

(87) PCT Pub. No.: WO2018/034227
PCT Pub. Date: Feb. 22, 2018

(65) Prior Publication Data
US 2019/0169294 A1 Jun. 6, 2019

(30) Foreign Application Priority Data
Aug. 15, 2016 (JP) .............. JP2016-159091

(51) Int. Cl.
| | | |
|---|---|---|
| C07K 16/28 | (2006.01) | |
| C07K 16/46 | (2006.01) | |
| A61P 31/10 | (2006.01) | |
| A61P 31/06 | (2006.01) | |
| A61P 15/14 | (2006.01) | |
| A61P 35/02 | (2006.01) | |
| A61P 33/02 | (2006.01) | |
| C12N 15/09 | (2006.01) | |
| A61P 31/00 | (2006.01) | |
| A61K 39/395 | (2006.01) | |
| C12N 5/10 | (2006.01) | |
| A61P 31/04 | (2006.01) | |
| A61P 35/00 | (2006.01) | |
| C12N 15/85 | (2006.01) | |

(52) U.S. Cl.
CPC ........ *C07K 16/2803* (2013.01); *A61K 39/395* (2013.01); *A61P 15/14* (2018.01); *A61P 31/00* (2018.01); *A61P 31/04* (2018.01); *A61P 31/06* (2018.01); *A61P 31/10* (2018.01); *A61P 33/02* (2018.01); *A61P 35/00* (2018.01); *A61P 35/02* (2018.01); *C07K 16/28* (2013.01); *C07K 16/46* (2013.01); *C12N 5/10* (2013.01); *C12N 15/09* (2013.01); *C12N 15/85* (2013.01); *C12N 2015/8518* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen ................ | C07K 16/2866 435/69.6 |
| 6,737,056 | B1 * | 5/2004 | Presta ................ | C07K 16/4291 424/133.1 |
| 2010/0233183 | A1 | 9/2010 | Triebel et al. | |

FOREIGN PATENT DOCUMENTS

| | | | | |
|---|---|---|---|---|
| CA | 2957275 | A1 * | 2/2016 | ......... C07K 16/2803 |
| EA | 23032 | B1 | 4/2016 | |

OTHER PUBLICATIONS

Vafa, Omid, et al. "An engineered Fc variant of an IgG eliminates all immune effector functions via structural perturbations." Methods 65.1 (2014): 114-126. (Year: 2014).*

(Continued)

*Primary Examiner* — Michael Szperka
*Assistant Examiner* — Lia E Taylor
(74) *Attorney, Agent, or Firm* — Schwegman Lundberg & Woessner, P.A.

(57) ABSTRACT

The present invention provides an anti-LAG-3 antibody capable of repeated administration even to animals other than rat. An anti-LAG-3 antibody comprising (a) a light chain comprising a light chain variable region containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region of an antibody of an animal other than rat; and (b) a heavy chain comprising a heavy chain variable region containing CDR1 having the amino acid sequence of GFDFDTYP (SEQ ID NO: 18), CDR2 having the amino acid sequence of ITIKTHNYAT (SEQ ID NO: 19) and CDR3 having the amino acid sequence of NREDFDY (SEQ ID NO: 20) and the heavy chain constant region of an antibody of an animal other than rat. A pharmaceutical composition comprising the above anti-LAG-3 antibody as an active ingredient. A method for preparing the above anti-LAG-3 antibody is also provided.

12 Claims, 8 Drawing Sheets
Specification includes a Sequence Listing.

(56) References Cited

OTHER PUBLICATIONS

Jha, Vibha et al. "Lymphocyte Activation Gene-3 (LAG-3) negatively regulates environmentally-induced autoimmunity." PloS one vol. 9,8 e104484. Aug. 14, 2014, doi:10.1371/journal.pone.0104484 (Year: 2014).*
Lubert Stryer, Biochemistry, 4th, WH Freeman, New York (1995) ISBN: 0-7167-2009-4 (Year: 1995).*
Farady, Christopher J et al. "Improving the species cross-reactivity of an antibody using computational design." Bioorganic & medicinal chemistry letters vol. 19,14 (2009): 3744-7. doi:10.1016/j.bmcl.2009.05.005 (Year: 2009).*
Okagawa, Tomohiro et al. "Cooperation of PD-1 and LAG-3 Contributes to T-Cell Exhaustion in Anaplasma marginale-Infected Cattle." Infection and immunity vol. 84,10 2779-90. Sep. 19, 2016, doi:10.1128/IAI.00278-16 (Year: 2016).*
Shapiro, Mika et al. "Lymphocyte activation gene 3: a novel therapeutic target in chronic lymphocytic leukemia." Haematologica vol. 102,5 (2017): 874-882. doi:10.3324/haematol.2016.148965 (Year: 2017).*
Bergeron, Lisa M., et al. "Comparative functional characterization of canine IgG subclasses." Veterinary immunology and immunopathology 157.1-2 (2014): 31-41. (Year: 2014).*
Bruce, Catriona J., et al. "Depletion of bovine CD8+ T cells with chCC63, a chimaeric mouse-bovine antibody." Veterinary immunology and immunopathology 71.3-4 (1999): 215-231. (Year: 1999).*
Okagawa, Tomohiro et al. "Anti-Bovine Programmed Death-1 Rat-Bovine Chimeric Antibody for Immunotherapy of Bovine Leukemia Virus Infection in Cattle." Frontiers in immunology vol. 8 650. Jun. 7, 2017, doi:10.3389/fimmu.2017.00650 (Year: 2017).*
Usman, Tahir, et al. "Novel polymorphisms in bovine CD4 and LAG-3 genes associated with somatic cell counts of clinical mastitis cows." Genetics and Molecular Research 17.1 (2018). (Year: 2018).*
Gebauer, Florian et al. "Lymphocyte activation gene-3 (LAG3) mRNA and protein expression on tumour infiltrating lymphocytes (TILs) in oesophageal adenocarcinoma." Journal of cancer research and clinical oncology vol. 146,9 (2020): 2319-2327. doi:10.1007/S00432-020-03295-7 (Year: 2020).*
Janeway, A. C., et al. "Immunobiology: the immune system in health and disease. London." Current Biology (1997): 3:1-3:11. (Year: 1997).*
Kipriyanov, Sergey M., and Fabrice Le Gall. "Generation and production of engineered antibodies." Molecular biotechnology 26.1 (2004): 39-60. (Year: 2004).*
"Russian Application No. 2019105702, Office Action dated Jul. 27, 2020", w/ English Translation, (Jul. 27, 2020), 10 pgs.
"Russian Application No. 2019105702, Search Report dated Jul. 27, 2020", w/ English Translation, (Jul. 27, 2020), 4 pgs.
"2014 Fiscal Year Annual Research Report Ushi no Men'eki Yokusei Juyotai no Kino Kaiseki Oyobi Nanjisei Shippei no Shinki Seigyoho eno Oyo Kenkyu", [Online]. Retrieved from the Internet: <URL: https://kaken.nii.ac.jp/ja/report/KAKENHI-PROJECT-13J01442/13J014422014jisseki/>, (Jun. 1, 2016), 3 pgs.
"International Application Serial No. PCT/JP2017/029057, International Search Report dated Oct. 31, 2017", (dated Oct. 31, 2017), 3 pgs.
"International Application Serial No. PCT/JP2017/029057, Written Opinion dated Oct. 31, 2017", (dated Oct. 31, 2017), 5 pgs.
Ikebuchi, Ryoyo, et al., "Influence of PD-L 1 cross-linking on cell death in PD-L 1-expressing cell lines and bovine lymphocytes", Immunology 142.4, (2014), 551-561.
Okagawa, Tomohiro, et al., "Bovine immunoinhibitory receptors contribute to suppression of *Mycobacterium avium* subsp. *paratuberculosis*-specific T-cell responses", Infection and immunity 84.1, (2016), 77-89.
"International Application Serial No. PCT/JP2017/029057, International Preliminary Report on Patentability dated Feb. 28, 2019", 8 pgs.
Blackburn, Shawn D, et al., "Coregulation of CD8+ T cell exhaustion by multiple inhibitory receptors during chronic viral infection", Nature immunology 10.1, (2009), 29-37.
Konnai, Satoru, et al., "Enhanced expression of LAG-3 on lymphocyte subpopulations from persistently lymphocytotic cattle infected with bovine leukemia virus", Comparative immunology, microbiology and infectious diseases 36.1, (2013), 63-69.
Shirai, Tatsuya, et al., "Molecular cloning of bovine lymphocyte activation gene-3 and its expression characteristics in bovine leukemia virus-infected cattle", Veterinary immunology and immunopathology 144.3-4, (2011), 462-467.
Triebel, Frederic, et al., "LAG-3, a novel lymphocyte activation gene closely related to CD4", Journal of Experimental Medicine 171.5, (1990), 1393-1405.
Woo, Seng-Ryong, et al., "Immune inhibitory molecules LAG-3 and PD-1 synergistically regulate T-cell function to promote tumoral immune escape", Cancer research 72.4, (2012), 917-927.
"European Application Serial No. 17841450.4, Extended Search Report dated Apr. 8, 2020", (dated Apr. 8, 2020), 16 pgs.
Workman, Creg J., et al., "Phenotypic analysis of the murine CD-4 related glycoprotein, CD223 (LAG-3)", European journal of immunology 32.8, (Aug. 1, 2002), 2255-2263.
Rivera, Shanemae M., et al., "Molecular characterization of the lymphocyte activation gene-3 (LAG-3, CD223) of swamp-and riverine-type water buffaloes (*Bubalus bubalis*)", Japanese Journal of Veterinary Research 65.2, (May 2017), pp. 65-74.

* cited by examiner

Fig. 1

Light Chain

*Italicized: Variable region sequence (Underlined boldface: CDR1, CDR2, CDR3 in this order from the NH2 terminus)*

Non-italicized: Constant region sequence (bovine IgG lambda, GenBank: X62917)

*MMSPVQSLFLLLLWLLGTNGDVVLTQTPPTLSATIGQSVSISCTSSQSLLDSDGNTYL*
*NWLLQRPGQSPQLLIYSVSNLEGVPARFSGSGSETDFTLKISGVEAEDLGVYYCMQ*
*ATHVPPTFGSGTKLEIK*RPKSPPSVTLFPPSTRELNGNKATLVCLISDFYPGSVTVVW
KADGSTITRNVETTRASKQSNSKYAASSYLSLTSSDWKSKGSYSCEVTHEGSTVTKT
VKPSECS*

Heavy Chain

*Italicized: Variable region sequence (Underlined boldface: CDR1, CDR2, CDR3 in this order from the NH2 terminus)*

Non-italicized: Constant region sequence (bovine IgG1, modified from GenBank X62916)

Doubly underlined: mutated amino acids in bovine IgG1 (CH2 domain)
(Amino acid numbers and mutations: 247 E→P, 248 L→V, 249 P→A, 250 G→deletion, 344 A→S, 345 P→S)

*MVLLELSVLALLRQGVHCEVQLVESHGGLVQPAGSLRLSCAASGFDFDTYPMSWVR*
*QAPGKGLDWVASITKTHNYATLYAASVKERFTISRDDSQSMVYLQMNNLKTEDTAL*
*YYCNREDIDYWGQGVMVTVSSASTTAPKVYPLSSCCGDKSSSTVTLGCLVSSYMPE*
PVTVTWNSGALSSGVHTFPAVLQSSGLYSLSSMVTVPGSTSGQTFTCNVAHPASSTK
VDKAVDPTCKPSPCDCCPPPEVAGPSVFIFPPKPKDTLTISGTPEVTCVVVDVGHDIP
EVKFSWFVDDVEVNTATTKPREEQFNSTYRVVSALRIQHQDWTGGKEFKCKVHNE
GLPSSIVRTISRTKGPAREPQVYVLAPPQEELSKSTVSLTCMVTSFYPDYIAVEWQRN
GQPESEDKYGTTPPQLDADSSYFLYSKLRVDRNSWQEGDTYTCVVMHEALHNHYT
QKSTSKSAGK*

SEQUENCE LISTING

```
<160> NUMBER OF SEQ ID NOS: 72

<210> SEQ ID NO 1
<211> LENGTH: 132
<212> TYPE: PRT
<213> ORGANISM: Rattus norvegicus

<400> SEQUENCE: 1

Met Met Ser Pro Val Gln Ser Leu Phe Leu Leu Leu Trp Ile Leu
1               5                   10                  15

Gly Thr Asn Gly Asp Val Val Leu Thr Gln Thr Pro Thr Leu Ser
                20                  25                  30

Ala Thr Ile Gly Gln Ser Val Ser Ile Ser Cys Arg Ser Ser Gln Ser
            35                  40                  45

Leu Leu Asp Ser Asp Gly Asn Thr Tyr Leu Asn Trp Leu Leu Gln Arg
    50                  55                  60

Pro Gly Gln Ser Pro Gln Leu Leu Ile Tyr Ser Val Ser Asn Leu Glu
65                  70                  75                  80

Ser Gly Val Pro Asn Arg Phe Ser Gly Ser Gly Ser Glu Thr Asp Phe
                85                  90                  95

Thr Leu Lys Ile Ser Gly Val Glu Ala Glu Asp Leu Gly Val Tyr Tyr
            100                 105                 110

Cys Met Gln Ala Thr His Val Pro Phe Thr Phe Gly Ser Gly Thr Lys
        115                 120                 125

Leu Glu Ile Lys
    130

<210> SEQ ID NO 2
<211> LENGTH: 134
<212> TYPE: PRT
<213> ORGANISM: Rattus norvegicus

<400> SEQUENCE: 2

Met Val Leu Leu Glu Leu Val Ser Val Ile Ala Leu Phe Gln Gly Val
1               5                   10                  15

His Cys Glu Val Gln Leu Val Glu Ser Gly Gly Gly Leu Val Gln Pro
                20                  25                  30

Lys Gly Ser Leu Arg Leu Ser Cys Ala Ala Ser Gly Phe Asp Phe Asp
```

```
                35                  40                  45
Thr Tyr Pro Met Ser Trp Val Arg Gln Ala Pro Gly Lys Gly Leu Asp
 50                  55                  60
Trp Val Ala Ser Ile Thr Ile Lys Thr His Asn Tyr Ala Thr Leu Tyr
 65                  70                  75                  80
Ala Ala Ser Val Lys Glu Arg Phe Thr Ile Ser Arg Asp Asp Ser Gln
                 85                  90                  95
Ser Met Val Tyr Leu Gln Met Asn Asn Leu Lys Thr Glu Asp Thr Ala
                100                 105                 110
Leu Tyr Tyr Cys Asn Arg Glu Asp Phe Asp Tyr Trp Gly Gln Gly Val
                115                 120                 125
Met Val Thr Val Ser Ser
                130

<210> SEQ ID NO 3
<211> LENGTH: 105
<212> TYPE: PRT
<213> ORGANISM: Bos taurus

<400> SEQUENCE: 3

Gln Pro Lys Ser Pro Ser Val Thr Leu Phe Pro Pro Ser Thr Glu
 1               5                  10                  15
Glu Leu Asn Gly Asn Lys Ala Thr Leu Val Cys Leu Ile Ser Asp Phe
                 20                  25                  30
Tyr Pro Gly Ser Val Thr Val Val Trp Lys Ala Asp Gly Ser Thr Ile
                 35                  40                  45
Thr Arg Asn Val Glu Thr Thr Arg Ala Ser Lys Gln Ser Asn Ser Lys
 50                  55                  60
Tyr Ala Ala Ser Ser Tyr Leu Ser Leu Thr Ser Ser Asp Trp Lys Ser
 65                  70                  75                  80
Lys Gly Ser Tyr Ser Cys Glu Val Thr His Glu Gly Ser Thr Val Thr
                 85                  90                  95
Lys Thr Val Lys Pro Ser Glu Cys Ser
                100                 105

<210> SEQ ID NO 4
<211> LENGTH: 328
<212> TYPE: PRT
<213> ORGANISM: Bos taurus

<400> SEQUENCE: 4

Ala Ser Thr Thr Ala Pro Lys Val Tyr Pro Leu Ser Ser Cys Cys Gly
 1               5                  10                  15
Asp Lys Ser Ser Ser Thr Val Thr Leu Gly Cys Leu Val Ser Ser Tyr
                 20                  25                  30
Met Pro Glu Pro Val Thr Val Thr Trp Asn Ser Gly Ala Leu Lys Ser
                 35                  40                  45
Gly Val His Thr Phe Pro Ala Val Leu Gln Ser Ser Gly Leu Tyr Ser
                 50                  55                  60
Leu Ser Ser Met Val Thr Val Pro Gly Ser Thr Ser Gly Gln Thr Phe
 65                  70                  75                  80
Thr Cys Asn Val Ala His Pro Ala Ser Ser Thr Lys Val Asp Lys Ala
                 85                  90                  95
Val Asp Pro Thr Cys Lys Pro Ser Pro Cys Asp Cys Cys Pro Pro Pro
                100                 105                 110
Pro Val Ala Gly Pro Ser Val Phe Ile Phe Pro Pro Lys Pro Lys Asp
```

```
                115                 120                 125
Thr Leu Thr Ile Ser Gly Thr Pro Glu Val Thr Cys Val Val Val Asp
        130                 135                 140

Val Gly His Asp Asp Pro Glu Val Lys Phe Ser Trp Phe Val Asp Asp
145                 150                 155                 160

Val Glu Val Asn Thr Ala Thr Thr Lys Pro Arg Glu Glu Gln Phe Asn
                165                 170                 175

Ser Thr Tyr Arg Val Val Ser Ala Leu Arg Ile Gln His Gln Asp Trp
            180                 185                 190

Thr Gly Gly Lys Glu Phe Lys Cys Lys Val His Asn Glu Gly Leu Pro
        195                 200                 205

Ser Ser Ile Val Arg Thr Ile Ser Arg Thr Lys Gly Pro Ala Arg Glu
    210                 215                 220

Pro Gln Val Tyr Val Leu Ala Pro Pro Gln Glu Glu Leu Ser Lys Ser
225                 230                 235                 240

Thr Val Ser Leu Thr Cys Met Val Thr Ser Phe Tyr Pro Asp Tyr Ile
                245                 250                 255

Ala Val Glu Trp Gln Arg Asn Gly Gln Pro Glu Ser Glu Asp Lys Tyr
            260                 265                 270

Gly Thr Thr Pro Pro Gln Leu Asp Ala Asp Ser Ser Tyr Phe Leu Tyr
        275                 280                 285

Ser Lys Leu Arg Val Asp Arg Asn Ser Trp Gln Glu Gly Asp Thr Tyr
    290                 295                 300

Thr Cys Val Val Met His Glu Ala Leu His Asn His Tyr Thr Gln Lys
305                 310                 315                 320

Ser Thr Ser Lys Ser Ala Gly Lys
                325

<210> SEQ ID NO 5
<211> LENGTH: 396
<212> TYPE: DNA
<213> ORGANISM: Rattus norvegicus

<400> SEQUENCE: 5
atgatgagtc ctgtccaatc cctgttttg ttattgcttt ggattctggg aaccaatggt      60
gatgttgtgc tgacccagac tccacccact ttatcggcta ccattggaca atcggtctcc    120
atctcttgca ggtcaagtca gagtctctta gatagtgatg gaaataccta tttaaattgg    180
ttgctacaga ggccaggcca atctccacag cttctaattt attcggtatc caacctggaa    240
tctggggtcc ccaacaggtt cagtggcagt gggtcagaaa cagatttcac actcaaaatc    300
agtggagtgg aggctgaaga tttgggagtt tattactgca tgcaagctac ccatgttcca    360
ttcacgttcg gctcagggac gaagttggaa ataaaa                              396

<210> SEQ ID NO 6
<211> LENGTH: 396
<212> TYPE: DNA
<213> ORGANISM: Rattus norvegicus

<400> SEQUENCE: 6
atgatgtctc ccgtccaaag cttgttcctg cttctcctct ggattctggg cacaaacgga     60
gatgtggttc tcacccagac ccccctact ctgtctgcca ccatcggcca gagcgtgtcc     120
atatcctgtc gcagctccca aagcctgctg gactccgatg gaatactta cctgaattgg     180 ctgttgcagc ggcctggcca gtccccccag ctgttgatct acagcgttag caatctggaa    240
```

```
agcggggtcc ccaaccgatt ctccggaagc ggctccgaga ccgattttac cctcaagatc      300
tccggcgtgg aagccgagga cctgggagtg tattattgca tgcaggccac ccatgtgccc      360
ttcaccttcg gtagcggtac caagttggag atcaag                                396

<210> SEQ ID NO 7
<211> LENGTH: 318
<212> TYPE: DNA
<213> ORGANISM: Bos taurus

<400> SEQUENCE: 7
cagcccaagt ccccaccctc ggtcaccctg ttcccgccct ccacggagga gctcaacggc       60
aacaaggcca ccctggtgtg tctcatcagc gacttctacc cgggtagcgt gaccgtggtc      120
tggaaggcag acggcagcac catcacccgc aacgtggaga ccacccgggc ctccaaacag      180
agcaacagca agtacgcggc cagcagctac ctgagcctga cgagcagcga ctggaaatcg      240
aaaggcagtt acagctgcga ggtcacgcac gaggggagca ccgtgacgaa gacagtgaag      300
ccctcagagt gttcttag                                                   318

<210> SEQ ID NO 8
<211> LENGTH: 987
<212> TYPE: DNA
<213> ORGANISM: Artificial Sequence
<220> FEATURE:
<223> OTHER INFORMATION: codon-optimized sequence

<400> SEQUENCE: 8
gctagcacca cagcacctaa agtttaccct ctgtcttcct gctgcggcga caagtcttca       60
tcaactgtta ctcttggatg cctggtctca agttacatgc ccgagcccgt gacagtgacc      120
tggaactcag gcgctctgaa gtctggagtg cacacatttc cagctgtgct tcagtctagc      180
ggcctgtatt ccctcagctc tatggttact gtacctggta gcaccagcgg acagactttc      240
acctgtaatg ttgcccatcc cgcatcttct accaaggtcg ataaagccgt tgaccccact      300
tgcaaaccat cccctttgtga ttgttgtcca cccctccag tggctggccc ttccgtcttc      360
attttccctc ctaaacctaa ggatactctg accatctcag ggacaccgga ggtcacctgt      420
gtcgtcgtgg acgtgggaca tgacgaccca gaagtcaagt tctcatggtt cgtggacgat      480
gtggaggtga acacagcaac aacaaagccc agagaagaac agtttaacag cacatatcgg      540
gtggtcagcg ccttgcgtat tcagcaccag gactggactg gtggcaagga gtttaagtgc      600
aaggtgcata cgaaggtct gccctcttct atagtgagaa ctatctcccg aactaagggc      660
cccgctcggg agcccaggt ttacgtcctt gctccccctc aggaggaact gagtaaatca      720
accgtgagtc tcacctgtat ggttacctca ttttacccag actacatcgc cgtagagtgg      780
cagaggaatg gacagccaga gtctgaggac aaatacggca ctactcctcc ccaactggat      840
gccgactctt cctacttcct ctactccaaa ttgcgagttg accggaactc atggcaggag      900
ggggacacat acacatgcgt cgttatgcac gaggccctgc acaaccatta cacccagaag      960
tccacatcta aaagtgcagg taagtaa                                         987

<210> SEQ ID NO 9
<211> LENGTH: 237
<212> TYPE: PRT
<213> ORGANISM: Artificial Sequence
<220> FEATURE:
<223> OTHER INFORMATION: chimeric L chain

<400> SEQUENCE: 9
```

Met Met Ser Pro Val Gln Ser Leu Phe Leu Leu Leu Trp Ile Leu
1               5                   10                  15

Gly Thr Asn Gly Asp Val Val Leu Thr Gln Thr Pro Thr Leu Ser
                20                  25                  30

Ala Thr Ile Gly Gln Ser Val Ser Ile Ser Cys Arg Ser Ser Gln Ser
            35                  40                  45

Leu Leu Asp Ser Asp Gly Asn Thr Tyr Leu Asn Trp Leu Leu Gln Arg
        50                  55                  60

Pro Gly Gln Ser Pro Gln Leu Leu Ile Tyr Ser Val Ser Asn Leu Glu
65                  70                  75                  80

Ser Gly Val Pro Asn Arg Phe Ser Gly Ser Gly Ser Glu Thr Asp Phe
                85                  90                  95

Thr Leu Lys Ile Ser Gly Val Glu Ala Glu Asp Leu Gly Val Tyr Tyr
            100                 105                 110

Cys Met Gln Ala Thr His Val Pro Phe Thr Phe Gly Ser Gly Thr Lys
        115                 120                 125

Leu Glu Ile Lys Gln Pro Lys Ser Pro Pro Ser Val Thr Leu Phe Pro
    130                 135                 140

Pro Ser Thr Glu Glu Leu Asn Gly Asn Lys Ala Thr Leu Val Cys Leu
145                 150                 155                 160

Ile Ser Asp Phe Tyr Pro Gly Ser Val Thr Val Val Trp Lys Ala Asp
                165                 170                 175

Gly Ser Thr Ile Thr Arg Asn Val Glu Thr Thr Arg Ala Ser Lys Gln
            180                 185                 190

Ser Asn Ser Lys Tyr Ala Ala Ser Ser Tyr Leu Ser Leu Thr Ser Ser
        195                 200                 205

Asp Trp Lys Ser Lys Gly Ser Tyr Ser Cys Glu Val Thr His Glu Gly
    210                 215                 220

Ser Thr Val Thr Lys Thr Val Lys Pro Ser Glu Cys Ser
225                 230                 235

<210> SEQ ID NO 10
<211> LENGTH: 462
<212> TYPE: PRT
<213> ORGANISM: Artificial Sequence
<220> FEATURE:
<223> OTHER INFORMATION: chimeric H chain

<400> SEQUENCE: 10

Met Val Leu Leu Glu Leu Val Ser Val Ile Ala Leu Phe Gln Gly Val
1               5                   10                  15

His Cys Glu Val Gln Leu Val Glu Ser Gly Gly Gly Leu Val Gln Pro
                20                  25                  30

Lys Gly Ser Leu Arg Leu Ser Cys Ala Ala Ser Gly Phe Asp Phe Asp
            35                  40                  45

Thr Tyr Pro Met Ser Trp Val Arg Gln Ala Pro Gly Lys Gly Leu Asp
        50                  55                  60

Trp Val Ala Ser Ile Thr Ile Lys Thr His Asn Tyr Ala Thr Leu Tyr
65                  70                  75                  80

Ala Ala Ser Val Lys Glu Arg Phe Thr Ile Ser Arg Asp Asp Ser Gln
                85                  90                  95

Ser Met Val Tyr Leu Gln Met Asn Asn Leu Lys Thr Glu Asp Thr Ala
            100                 105                 110

Leu Tyr Tyr Cys Asn Arg Glu Asp Phe Asp Tyr Trp Gly Gln Gly Val
        115                 120                 125

```
Met Val Thr Val Ser Ser Ala Ser Thr Thr Ala Pro Lys Val Tyr Pro
130                 135                 140

Leu Ser Ser Cys Cys Gly Asp Lys Ser Ser Thr Val Thr Leu Gly
145                 150                 155                 160

Cys Leu Val Ser Ser Tyr Met Pro Glu Pro Val Thr Val Thr Trp Asn
                165                 170                 175

Ser Gly Ala Leu Lys Ser Gly Val His Thr Phe Pro Ala Val Leu Gln
                180                 185                 190

Ser Ser Gly Leu Tyr Ser Leu Ser Ser Met Val Thr Val Pro Gly Ser
                195                 200                 205

Thr Ser Gly Gln Thr Phe Thr Cys Asn Val Ala His Pro Ala Ser Ser
210                 215                 220

Thr Lys Val Asp Lys Ala Val Asp Pro Thr Cys Lys Pro Ser Pro Cys
225                 230                 235                 240

Asp Cys Cys Pro Pro Pro Val Ala Gly Pro Ser Val Phe Ile Phe
                245                 250                 255

Pro Pro Lys Pro Lys Asp Thr Leu Thr Ile Ser Gly Thr Pro Glu Val
                260                 265                 270

Thr Cys Val Val Asp Val Gly His Asp Asp Pro Glu Val Lys Phe
                275                 280                 285

Ser Trp Phe Val Asp Asp Val Glu Val Asn Thr Ala Thr Thr Lys Pro
290                 295                 300

Arg Glu Glu Gln Phe Asn Ser Thr Tyr Arg Val Val Ser Ala Leu Arg
305                 310                 315                 320

Ile Gln His Gln Asp Trp Thr Gly Gly Lys Glu Phe Lys Cys Lys Val
                325                 330                 335

His Asn Glu Gly Leu Pro Ser Ser Ile Val Arg Thr Ile Ser Arg Thr
                340                 345                 350

Lys Gly Pro Ala Arg Glu Pro Gln Val Tyr Val Leu Ala Pro Pro Gln
                355                 360                 365

Glu Glu Leu Ser Lys Ser Thr Val Ser Leu Thr Cys Met Val Thr Ser
370                 375                 380

Phe Tyr Pro Asp Tyr Ile Ala Val Glu Trp Gln Arg Asn Gly Gln Pro
385                 390                 395                 400

Glu Ser Glu Asp Lys Tyr Gly Thr Thr Pro Pro Gln Leu Asp Ala Asp
                405                 410                 415

Ser Ser Tyr Phe Leu Tyr Ser Lys Leu Arg Val Asp Arg Asn Ser Trp
                420                 425                 430

Gln Glu Gly Asp Thr Tyr Thr Cys Val Val Met His Glu Ala Leu His
                435                 440                 445

Asn His Tyr Thr Gln Lys Ser Thr Ser Lys Ser Ala Gly Lys
450                 455                 460

<210> SEQ ID NO 11
<211> LENGTH: 396
<212> TYPE: DNA
<213> ORGANISM: Artificial Sequence
<220> FEATURE:
<223> OTHER INFORMATION: codon-optimized sequence

<400> SEQUENCE: 11
atgatgtctc ccgtccaaag cttgttcctg cttctcctct ggattctggg cacaaacgga      60
gatgtggttc tcacccagac ccccctact ctgtctgcca ccatcggcca gagcgtgtcc     120
atatcctgtc gcagctccca aagcctgctg gactccgatg ggaatactta cctgaattgg     180
```

```
ctgttgcagc ggcctggcca gtcccccag ctgttgatct acagcgttag caatctggaa      240
agcggggtcc ccaaccgatt ctccggaagc ggctccgaga ccgatttac cctcaagatc       300 tccggcgtgg aagccgagga cctgggagtg tattattgca tgcaggccac ccatgtgccc      360
ttcaccttcg gtagcggtac caagttggag atcaag                               396

<210> SEQ ID NO 12
<211> LENGTH: 402
<212> TYPE: DNA
<213> ORGANISM: Artificial Sequence
<220> FEATURE:
<223> OTHER INFORMATION: codon-optimized sequence

<400> SEQUENCE: 12
atggtgcttc tcgagctggt cagcgtgatt gctctgtttc agggcgtgca ctgcgaagtg       60
cagctggtgg agagtggtgg tgggctcgtg caaccaaaag gcagtctcag gctgagttgt      120
gccgcctccg gattcgattt cgacacctac ccaatgagct gggtcaggca agccccaggg      180
aaaggactcg attgggtggc aagcattacc atcaagacac acaattatgc taccctgtat      240
gccgcaagcg taaaggaacg ctttaccatc tcccgcgatg atagccagtc catggtatat      300
ttgcaaatga ataatttgaa cagaagat accgctttgt attattgcaa cagagaagat      360
tttgattatt gggggcaggg ggtgatggta accgtgtcca gc                        402

<210> SEQ ID NO 13
<211> LENGTH: 318
<212> TYPE: DNA
<213> ORGANISM: Artificial Sequence
<220> FEATURE:
<223> OTHER INFORMATION: codon-optimized sequence

<400> SEQUENCE: 13
cagcctaagt cccctccttc agtcaccctg tttccaccat ctaccgaaga actcaacggg       60
aataaagcaa cactggtgtg ccttatttct gatttttacc cagggtctgt gacagtggtt      120
tggaaagctg acggttcaac aattacaaga acgtggaga caacaagggc ttctaagcag      180
tcaaactcta agtatgctgc aagttcttac ctttctctta agtagtga ctggaaaagt      240 aagggcagtt attcatgcga ggtcactcac gagggaagta ctgtaactaa aactgtaaaa      300
ccatcagagt gttcatag                                                   318

<210> SEQ ID NO 14
<211> LENGTH: 714
<212> TYPE: DNA
<213> ORGANISM: Artificial Sequence
<220> FEATURE:
<223> OTHER INFORMATION: codon-optimized sequence

<400> SEQUENCE: 14
atgatgtctc ccgtccaaag cttgttcctg cttctcctct ggattctggg cacaaacgga       60
gatgtggttc tcacccagac ccccctact ctgtctgcca ccatcggcca gagcgtgtcc       120
atatcctgtc gcagctccca aagcctgctg gactccgatg gaatactta cctgaattgg      180 ctgttgcagc ggcctggcca gtcccccag ctgttgatct acagcgttag caatctggaa      240
agcggggtcc ccaaccgatt ctccggaagc ggctccgaga ccgatttac cctcaagatc      300 tccggcgtgg aagccgagga cctgggagtg tattattgca tgcaggccac ccatgtgccc      360
ttcaccttcg gtagcggtac caagttggag atcaagcagc ctaagtcccc tccttcagtc     420
```

```
acctgtttc caccatctac cgaagaactc aacgggaata agcaacact ggtgtgcctt      480 atttctgatt tttacccagg gtctgtgaca gtggtttgga aagctgacgg ttcaacaatt     540
acaagaaacg tggagacaac aagggcttct aagcagtcaa actctaagta tgctgcaagt     600
tcttaccttt ctcttacaag tagtgactgg aaaagtaagg gcagttattc atgcgaggtc     660
actcacgagg gaagtactgt aactaaaact gtaaaaccat cagagtgttc atag            714
```

<210> SEQ ID NO 15
<211> LENGTH: 1389
<212> TYPE: DNA
<213> ORGANISM: Artificial Sequence
<220> FEATURE:
<223> OTHER INFORMATION: codon-optimized sequence

<400> SEQUENCE: 15

```
atggtgcttc tcgagctggt cagcgtgatt gctctgtttc agggcgtgca ctgcgaagtg      60
cagctggtgg agagtggtgg tgggctcgtg caaccaaaag gcagtctcag gctgagttgt     120
gccgcctccg gattcgattt cgacacctac ccaatgagct gggtcaggca agccccaggg     180
aaaggactcg attgggtggc aagcattacc atcaagacac acaattatgc taccctgtat     240
gccgcaagcg taaggaacg ctttaccatc tcccgcgatg atagccagtc catggtatat     300
ttgcaaatga ataattaa gacagaagat accgctttgt attattgcaa cagagaagat     360
tttgattatt gggggcaggg ggtgatggta ccgtgtcca cgctagcac cacagcacct     420 aaagtttacc ctctgtcttc ctgctgcggc gacaagtctt catcaactgt tactcttgga     480
tgcctggtct caagttacat gcccgagccc gtgacagtga cctggaactc aggcgctctg     540
aagtctggag tgcacacatt tccagctgtg cttcagtcta gcggcctgta ttccctcagc     600
tctatggtta ctgtacctgg tagcaccagc ggacagactt tcacctgtaa tgttgcccat     660
cccgcatctt ctaccaaggt cgataaagcc gttgaccca cttgcaaacc atccccttgt     720
gattgttgtc cacccctcc agtggctggc ccttccgtct tcattttccc tcctaaacct     780
aaggatactc tgaccatctc agggacaccc gaggtcacct gtgtcgtcgt ggacgtggga     840
catgacgacc cagaagtcaa gttctcatgg ttcgtggacg atgtggaggt gaacacagca     900
acaacaaagc ccagagaaga acagtttaac agcacatatc gggtggtcag cgccttgcgt     960
attcagcacc aggactggac tggtggcaag gagtttaagt gcaaggtgca taacgaaggt    1020
ctgccctctt ctatagtgag aactatctcc gaactaagg gccccgctcg ggagcccag      1080 gtttacgtcc ttgctccccc tcaggaggaa ctgagtaaat caaccgtgag tctcacctgt    1140
atggttacct catttttaccc agactacatc gccgtagagt ggcagaggaa tggacagcca    1200
gagtctgagg acaaatacgg cactactcct ccccaactgg atgccgactc ttcctacttc    1260
ctctactcca aattgcgagt tgaccggaac tcatggcagg aggggacac atacacatgc    1320 gtcgttatgc acgaggccct gcacaaccat tacacccaga gtccacatc taaaagtgca    1380 ggtaagtaa                                                             1389
```

<210> SEQ ID NO 16
<211> LENGTH: 11
<212> TYPE: PRT
<213> ORGANISM: Rattus norvegicus

<400> SEQUENCE: 16

Gln Ser Leu Leu Asp Ser Asp Gly Asn Thr Tyr
1               5                   10

<210> SEQ ID NO 17
<211> LENGTH: 9
<212> TYPE: PRT
<213> ORGANISM: Rattus norvegicus

<400> SEQUENCE: 17

Met Gln Ala Thr His Val Pro Phe Thr
1               5

<210> SEQ ID NO 18
<211> LENGTH: 8
<212> TYPE: PRT
<213> ORGANISM: Rattus norvegicus

<400> SEQUENCE: 18

Gly Phe Asp Phe Asp Thr Tyr Pro
1               5

<210> SEQ ID NO 19
<211> LENGTH: 10
<212> TYPE: PRT
<213> ORGANISM: Rattus norvegicus

<400> SEQUENCE: 19

Ile Thr Ile Lys Thr His Asn Tyr Ala Thr
1               5                   10

<210> SEQ ID NO 20
<211> LENGTH: 7
<212> TYPE: PRT
<213> ORGANISM: Rattus norvegicus

<400> SEQUENCE: 20

Asn Arg Glu Asp Phe Asp Tyr
1               5

<210> SEQ ID NO 21
<211> LENGTH: 329
<212> TYPE: PRT
<213> ORGANISM: Bos taurus

<400> SEQUENCE: 21

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Asp Pro Thr Cys Lys Pro Ser Pro Cys Asp Cys Pro Pro Pro
            100                 105                 110

Glu Leu Pro Gly Gly Pro Ser Val Phe Ile Phe Pro Pro Lys Pro Lys
        115                 120                 125

Asp Thr Leu Thr Ile Ser Gly Thr Pro Glu Val Thr Cys Val Val Val
    130                 135                 140

-continued

```
Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
            165                 170                 175

Asn Ser Thr Tyr Arg Val Val Ser Ala Leu Arg Ile Gln His Gln Asp
        180                 185                 190

Trp Thr Gly Gly Lys Glu Phe Lys Cys Lys Val His Asn Glu Gly Leu
    195                 200                 205

Pro Ala Pro Ile Val Arg Thr Ile Ser Arg Thr Lys Gly Pro Ala Arg
210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
            245                 250                 255

Ile Ala Val Glu Trp Gln Arg Asn Gly Gln Pro Glu Ser Glu Asp Lys
        260                 265                 270

Tyr Gly Thr Thr Pro Pro Gln Leu Asp Ala Asp Ser Ser Tyr Phe Leu
    275                 280                 285

Tyr Ser Lys Leu Arg Val Asp Arg Asn Ser Trp Gln Glu Gly Asp Thr
290                 295                 300

Tyr Thr Cys Val Val Met His Glu Ala Leu His Asn His Tyr Thr Gln
305                 310                 315                 320

Lys Ser Thr Ser Lys Ser Ala Gly Lys
            325
```

```
<210> SEQ ID NO 22
<211> LENGTH: 329
<212> TYPE: PRT
<213> ORGANISM: Bos taurus

<400> SEQUENCE: 22

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
            85                  90                  95

Val Asp Pro Thr Cys Lys Pro Ser Pro Cys Asp Cys Cys Pro Pro Pro
        100                 105                 110

Glu Leu Pro Gly Gly Pro Ser Val Phe Ile Phe Pro Pro Lys Pro Lys
    115                 120                 125

Asp Thr Leu Thr Ile Ser Gly Thr Pro Glu Val Thr Cys Val Val Val
130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
            165                 170                 175

Asn Ser Thr Tyr Arg Val Val Ser Ala Leu Arg Ile Gln His Gln Asp
        180                 185                 190
```

Trp Thr Gly Gly Lys Glu Phe Lys Cys Lys Val His Asn Glu Gly Leu
            195                 200                 205

Pro Ala Pro Ile Val Arg Thr Ile Ser Arg Thr Lys Gly Pro Ala Arg
210                 215                 220

Glu Pro Gln Val Tyr Val Leu Ala Pro Pro Gln Glu Glu Leu Ser Lys
225                 230                 235                 240

Ser Thr Val Ser Leu Thr Cys Met Val Thr Ser Phe Tyr Pro Asp Tyr
            245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Ser Ser Tyr Phe Leu
            275                 280                 285

Tyr Ser Lys Leu Arg Val Asp Arg Asn Ser Trp Gln Glu Gly Asp Thr
290                 295                 300

Tyr Thr Cys Val Val Met His Glu Ala Leu His Asn His Tyr Thr Gln
305                 310                 315                 320

Lys Ser Thr Ser Lys Ser Ala Gly Lys
            325

<210> SEQ ID NO 23
<211> LENGTH: 329
<212> TYPE: PRT
<213> ORGANISM: Bos taurus

<400> SEQUENCE: 23

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Thr Gln Thr
65                  70                  75                  80

Phe Thr Cys Asn Val Ala His Pro Ala Ser Ser Thr Lys Val Asp Lys
            85                  90                  95

Ala Val Asp Pro Arg Cys Lys Thr Thr Cys Asp Cys Cys Pro Pro Pro
            100                 105                 110

Glu Leu Pro Gly Gly Pro Ser Val Phe Ile Phe Pro Pro Lys Pro Lys
            115                 120                 125

Asp Thr Leu Thr Ile Ser Gly Thr Pro Glu Val Thr Cys Val Val Val
130                 135                 140

Asp Val Gly His Asp Asp Pro Glu Val Lys Phe Ser Trp Phe Val Asp
145                 150                 155                 160

Asp Val Glu Val Asn Thr Ala Thr Thr Lys Pro Arg Glu Glu Gln Phe
            165                 170                 175

Asn Ser Thr Tyr Arg Val Val Ser Ala Leu Arg Ile Gln His Gln Asp
            180                 185                 190

Trp Thr Gly Gly Lys Glu Phe Lys Cys Lys Val His Asn Glu Gly Leu
            195                 200                 205

Pro Ala Pro Ile Val Arg Thr Ile Ser Arg Thr Lys Gly Pro Ala Arg
210                 215                 220

Glu Pro Gln Val Tyr Val Leu Ala Pro Pro Gln Glu Glu Leu Ser Lys

```
225                 230                 235                 240
Ser Thr Val Ser Leu Thr Cys Met Val Thr Ser Phe Tyr Pro Asp Tyr
                245                 250                 255

Ile Ala Val Glu Trp Gln Arg Asn Gly Gln Pro Glu Ser Glu Asp Lys
            260                 265                 270

Tyr Gly Thr Thr Pro Pro Gln Leu Asp Ala Asp Gly Ser Tyr Phe Leu
            275                 280                 285

Tyr Ser Arg Leu Arg Val Asp Arg Asn Ser Trp Gln Glu Gly Asp Thr
290                 295                 300

Tyr Thr Cys Val Val Met His Glu Ala Leu His Asn His Tyr Thr Gln
305                 310                 315                 320

Lys Ser Thr Ser Lys Ser Ala Gly Lys
                325

<210> SEQ ID NO 24
<211> LENGTH: 326
<212> TYPE: PRT
<213> ORGANISM: Bos taurus

<400> SEQUENCE: 24

Ala Ser Thr Thr Ala Pro Lys Val Tyr Pro Leu Ala Ser Ser Cys Gly
1               5                   10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Ala Ser Ser Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ile Asp Cys Ser Lys Cys His Asn Gln Pro Cys Val
            100                 105                 110

Arg Glu Pro Ser Val Phe Ile Phe Pro Pro Lys Pro Lys Asp Thr Leu
        115                 120                 125

Met Ile Thr Gly Thr Pro Glu Val Thr Cys Val Val Val Asn Val Gly
    130                 135                 140

His Asp Asn Pro Glu Val Gln Phe Ser Trp Phe Val Asp Asp Val Glu
145                 150                 155                 160

Val His Thr Ala Arg Ser Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Asn Lys Gly Leu Ser Ala Pro
        195                 200                 205

Ile Val Arg Ile Ile Ser Arg Ser Lys Gly Pro Ala Arg Glu Pro Gln
    210                 215                 220

Val Tyr Val Leu Asp Pro Pro Lys Glu Glu Leu Ser Lys Ser Thr Leu
225                 230                 235                 240

Ser Val Thr Cys Met Val Thr Gly Phe Tyr Pro Glu Asp Val Ala Val
                245                 250                 255

Glu Trp Gln Arg Asn Arg Gln Thr Glu Ser Glu Asp Lys Tyr Arg Thr
            260                 265                 270
```

```
Thr Pro Pro Gln Leu Asp Thr Asp Arg Ser Tyr Phe Leu Tyr Ser Lys
            275                 280                 285

Leu Arg Val Asp Arg Asn Ser Trp Gln Glu Gly Asp Ala Tyr Thr Cys
        290                 295                 300

Val Val Met His Glu Ala Leu His Asn His Tyr Met Gln Lys Ser Thr
305                 310                 315                 320

Ser Lys Ser Ala Gly Lys
                325

<210> SEQ ID NO 25
<211> LENGTH: 326
<212> TYPE: PRT
<213> ORGANISM: Bos taurus

<400> SEQUENCE: 25

Ala Ser Thr Thr Ala Pro Lys Val Tyr Pro Leu Ser Ser Cys Cys Gly
1               5                   10                  15

Asp Lys Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
        35                  40                  45

Gly Val His Thr Phe Pro Ala Val Leu Gln Ser Ser Gly Leu Tyr Ser
    50                  55                  60

Leu Ser Ser Met Val Thr Val Pro Gly Ser Thr Ser Gly Gln Thr Phe
65                  70                  75                  80

Thr Cys Asn Val Ala His Pro Ala Ser Ser Thr Lys Val Asp Lys Ala
                85                  90                  95

Val Gly Val Ser Ser Asp Cys Ser Lys Pro Asn Asn Gln His Cys Val
            100                 105                 110

Arg Glu Pro Ser Val Phe Ile Phe Pro Pro Lys Pro Lys Asp Thr Leu
        115                 120                 125

Met Ile Thr Gly Thr Pro Glu Val Thr Cys Val Val Val Asn Val Gly
    130                 135                 140

His Asp Asn Pro Glu Val Gln Phe Ser Trp Phe Val Asp Asp Val Glu
145                 150                 155                 160

Val His Thr Ala Arg Thr Lys Pro Arg Glu Glu Gln Phe Asn Ser Thr
                165                 170                 175

Tyr Arg Val Val Ser Ala Leu Pro Ile Gln His Gln Asp Trp Thr Gly
            180                 185                 190

Gly Lys Glu Phe Lys Cys Lys Val Asn Ile Lys Gly Leu Ser Ala Ser
        195                 200                 205

Ile Val Arg Ile Ile Ser Arg Ser Lys Gly Pro Ala Arg Glu Pro Gln
    210                 215                 220

Val Tyr Val Leu Asp Pro Pro Lys Glu Glu Leu Ser Lys Ser Thr Val
225                 230                 235                 240

Ser Val Thr Cys Met Val Ile Gly Phe Tyr Pro Glu Asp Val Asp Val
                245                 250                 255

Glu Trp Gln Arg Asp Arg Gln Thr Glu Ser Glu Asp Lys Tyr Arg Thr
            260                 265                 270

Thr Pro Pro Gln Leu Asp Ala Asp Arg Ser Tyr Phe Leu Tyr Ser Lys
        275                 280                 285

Leu Arg Val Asp Arg Asn Ser Trp Gln Arg Gly Asp Thr Tyr Thr Cys
    290                 295                 300

Val Val Met His Glu Ala Leu His Asn His Tyr Met Gln Lys Ser Thr
305                 310                 315                 320
```

Ser Lys Ser Ala Gly Lys
            325

<210> SEQ ID NO 26
<211> LENGTH: 327
<212> TYPE: PRT
<213> ORGANISM: Bos taurus

<400> SEQUENCE: 26

Ala Ser Thr Thr Ala Pro Lys Val Tyr Pro Leu Ser Cys Cys Gly
1               5                   10                  15

Asp Lys Ser Ser Ser Gly Val Thr Leu Gly Cys Leu Val Ser Ser Tyr
            20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
        50                  55                  60

Leu Ser Ser Met Val Thr Val Pro Ala Ser Ser Gly Thr Gln Thr
65                  70                  75                  80

Phe Thr Cys Asn Val Ala His Pro Ala Ser Ser Thr Lys Val Asp Lys
                85                  90                  95

Ala Val Gly Val Ser Ser Asp Cys Ser Lys Pro Asn Asn Gln His Cys
            100                 105                 110

Val Arg Glu Pro Ser Val Phe Ile Phe Pro Lys Pro Lys Asp Thr
            115                 120                 125

Leu Met Ile Thr Gly Thr Pro Glu Val Thr Cys Val Val Asn Val
130                 135                 140

Gly His Asp Asn Pro Glu Val Gln Phe Ser Trp Phe Val Asp Asp Val
145                 150                 155                 160

Glu Val His Thr Ala Arg Thr Lys Pro Arg Glu Gln Phe Asn Ser
                165                 170                 175

Thr Tyr Arg Val Val Ser Ala Leu Pro Ile Gln His Gln Asp Trp Thr
            180                 185                 190

Gly Gly Lys Glu Phe Lys Cys Lys Val Asn Ile Lys Gly Leu Ser Ala
        195                 200                 205

Ser Ile Val Arg Ile Ile Ser Arg Ser Lys Gly Pro Ala Arg Glu Pro
210                 215                 220

Gln Val Tyr Val Leu Asp Pro Pro Lys Glu Glu Leu Ser Lys Ser Thr
225                 230                 235                 240

Val Ser Leu Thr Cys Met Val Ile Gly Phe Tyr Pro Glu Asp Val Asp
                245                 250                 255

Val Glu Trp Gln Arg Asp Arg Gln Thr Glu Ser Glu Asp Lys Tyr Arg
            260                 265                 270

Thr Thr Pro Pro Gln Leu Asp Ala Asp Arg Ser Tyr Phe Leu Tyr Ser
        275                 280                 285

Lys Leu Arg Val Asp Arg Asn Ser Trp Gln Arg Gly Asp Thr Tyr Thr
290                 295                 300

Cys Val Val Met His Glu Ala Leu His Asn His Tyr Met Gln Lys Ser
305                 310                 315                 320

Thr Ser Lys Ser Ala Gly Lys
            325

<210> SEQ ID NO 27
<211> LENGTH: 352
<212> TYPE: PRT

<213> ORGANISM: Bos taurus

<400> SEQUENCE: 27

```
Ala Ser Thr Thr Ala Pro Lys Val Tyr Pro Leu Ala Ser Ser Cys Gly
1               5                   10                  15
Asp Thr Ser Ser Ser Thr Val Thr Leu Gly Cys Leu Val Ser Ser Tyr
            20                  25                  30
Met Pro Glu Pro Val Thr Val Thr Trp Asn Ser Gly Ala Leu Lys Ser
        35                  40                  45
Gly Val His Thr Phe Pro Ala Val Arg Gln Ser Ser Gly Leu Tyr Ser
    50                  55                  60
Leu Ser Ser Met Val Thr Val Pro Ala Ser Ser Glu Thr Gln Thr
65                  70                  75                  80
Phe Thr Cys Asn Val Ala His Pro Ala Ser Ser Thr Lys Val Asp Lys
                85                  90                  95
Ala Val Thr Ala Arg Arg Pro Val Pro Thr Thr Pro Lys Thr Ile
            100                 105                 110
Pro Pro Gly Lys Pro Thr Thr Pro Lys Ser Glu Val Glu Lys Thr Pro
            115                 120                 125
Cys Gln Cys Ser Lys Cys Pro Glu Pro Leu Gly Gly Leu Ser Val Phe
130                 135                 140
Ile Phe Pro Pro Lys Pro Lys Asp Thr Leu Thr Ile Ser Gly Thr Pro
145                 150                 155                 160
Glu Val Thr Cys Val Val Val Asp Val Gly Gln Asp Pro Glu Val
            165                 170                 175
Gln Phe Ser Trp Phe Val Asp Asp Val Glu Val His Thr Ala Arg Thr
            180                 185                 190
Lys Pro Arg Glu Glu Gln Phe Asn Ser Thr Tyr Arg Val Val Ser Ala
            195                 200                 205
Leu Arg Ile Gln His Gln Asp Trp Leu Gln Gly Lys Glu Phe Lys Cys
210                 215                 220
Lys Val Asn Asn Lys Gly Leu Pro Ala Pro Ile Val Arg Thr Ile Ser
225                 230                 235                 240
Arg Thr Lys Gly Gln Ala Arg Glu Pro Gln Val Tyr Val Leu Ala Pro
            245                 250                 255
Pro Arg Glu Glu Leu Ser Lys Ser Thr Leu Ser Leu Thr Cys Leu Ile
            260                 265                 270
Thr Gly Phe Tyr Pro Glu Glu Ile Asp Val Glu Trp Gln Arg Asn Gly
            275                 280                 285
Gln Pro Glu Ser Glu Asp Lys Tyr His Thr Thr Ala Pro Gln Leu Asp
        290                 295                 300
Ala Asp Gly Ser Tyr Phe Leu Tyr Ser Lys Leu Arg Val Asn Lys Ser
305                 310                 315                 320
Ser Trp Gln Glu Gly Asp His Tyr Thr Cys Ala Val Met His Glu Ala
                325                 330                 335
Leu Arg Asn His Tyr Lys Glu Lys Ser Ile Ser Arg Ser Pro Gly Lys
            340                 345                 350
```

<210> SEQ ID NO 28
<211> LENGTH: 352
<212> TYPE: PRT
<213> ORGANISM: Bos taurus

<400> SEQUENCE: 28

Ala Ser Thr Thr Ala Pro Lys Val Tyr Pro Leu Ala Ser Arg Cys Gly

```
1               5                   10                  15
Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
            50                  55                  60

Leu Ser Ser Met Val Thr Val Pro Ala Ser Ser Glu Thr Gln Thr
65                  70                  75                  80

Phe Thr Cys Asn Val Ala His Pro Ala Ser Ser Thr Lys Val Asp Lys
                85                  90                  95

Ala Val Thr Ala Arg Arg Pro Val Pro Thr Thr Pro Lys Thr Thr Ile
            100                 105                 110

Pro Pro Gly Lys Pro Thr Thr Gln Glu Ser Glu Val Glu Lys Thr Pro
            115                 120                 125

Cys Gln Cys Ser Lys Cys Pro Glu Pro Leu Gly Gly Leu Ser Val Phe
        130                 135                 140

Ile Phe Pro Pro Lys Pro Lys Asp Thr Leu Thr Ile Ser Gly Thr Pro
145                 150                 155                 160

Glu Val Thr Cys Val Val Val Asp Val Gly Gln Asp Pro Glu Val
            165                 170                 175

Gln Phe Ser Trp Phe Val Asp Asp Val Glu Val His Thr Ala Arg Thr
        180                 185                 190

Lys Pro Arg Glu Glu Gln Phe Asn Ser Thr Tyr Arg Val Val Ser Ala
            195                 200                 205

Leu Arg Ile Gln His Gln Asp Trp Leu Gln Gly Lys Glu Phe Lys Cys
        210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
            245                 250                 255

Pro Arg Glu Glu Leu Ser Lys Ser Thr Leu Ser Leu Thr Cys Leu Ile
            260                 265                 270

Thr Gly Phe Tyr Pro Glu Glu Ile Asp Val Glu Trp Gln Arg Asn Gly
            275                 280                 285

Gln Pro Glu Ser Glu Asp Lys Tyr His Thr Thr Ala Pro Gln Leu Asp
            290                 295                 300

Ala Asp Gly Ser Tyr Phe Leu Tyr Ser Arg Leu Arg Val Asn Lys Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Ser Ile Ser Arg Ser Pro Gly Lys
            340                 345                 350
```

<210> SEQ ID NO 29
<211> LENGTH: 990
<212> TYPE: DNA
<213> ORGANISM: Bos taurus

<400> SEQUENCE: 29

```
gcctccacca cagccccgaa agtctaccct ctgagttctt gctgcgggga caagtccagc      60
tccaccgtga ccctgggctg cctggtctcc agctacatgc ccgagccggt gaccgtgacc     120
tggaactcgg gtgccctgaa gagcggcgtg cacaccttcc cggctgtcct tcagtcctcc     180
```

```
gggctgtact ctctcagcag catggtgacc gtgcccggca gcacctcagg acagaccttc     240
acctgcaacg tagcccaccc ggccagcagc accaaggtgg acaaggctgt tgatcccaca     300
tgcaaaccat caccctgtga ctgttgccca ccccctgagc tccccggagg accctctgtc     360
ttcatcttcc caccgaaacc caaggacacc ctcacaatct cgggaacgcc cgaggtcacg     420
tgtgtggtgg tggacgtggg ccacgatgac cccgaggtga agttctcctg gttcgtggac     480
gacgtggagg taaacacagc cacgacgaag ccgagagagg agcagttcaa cagcacctac     540
cgcgtggtca gcgccctgcg catccagcac caggactgga ctggaggaaa ggagttcaag     600
tgcaaggtcc acaacgaagg cctcccggcc ccatcgtga ggaccatctc caggaccaaa      660
gggccggccc gggagccgca ggtgtatgtc ctgccccac cccaggaaga gctcagcaaa      720
agcacggtca gcctcacctg catggtcacc agcttctacc cagactacat cgccgtggag     780
tggcagagaa acgggcagcc tgagtcggag gacaagtacg gcacgacccc gccccagctg     840
gacgccgaca gctcctactt cctgtacagc aagctcaggg tggacaggaa cagctggcag     900
gaaggagaca cctacgcgtg tgtggtgatg cacgaggccc tgcacaatca ctacacgcag     960
aagtccacct ctaagtctgc gggtaaatga                                      990
```

```
<210> SEQ ID NO 30
<211> LENGTH: 990
<212> TYPE: DNA
<213> ORGANISM: Bos taurus

<400> SEQUENCE: 30
gcctccacca cagccccgaa agtctaccct ctgagttctt gctgcgggga caagtccagc     60
tccaccgtga ccctgggctg cctggtctcc agctacatgc ccgagccggt gaccgtgacc     120
tggaactcgg gtgccctgaa gagcggcgtg cacaccttcc cggccgtcct tcagtcctcc    180
gggctgtact ctctcagcag catggtgacc gtgcccggca gcacctcagg acagaccttc    240
acctgcaacg tagcccaccc ggccagcagc accaaggtgg acaaggctgt tgatcccaca    300
tgcaaaccat caccctgtga ctgttgccca ccccctgagc tccccggagg accctctgtc    360
ttcatcttcc caccgaaacc caaggacacc ctcacaatct cgggaacgcc cgaggtcacg    420
tgtgtggtgg tggacgtggg ccacgatgac cccgaggtga agttctcctg gttcgtggac    480
gacgtggagg taaacacagc cacgacgaag ccgagagagg agcagttcaa cagcacctac    540
cgcgtggtca gcgccctgcg catccagcac caggactgga ctggaggaaa ggagttcaag    600
tgcaaggtcc acaacgaagg cctcccggcc ccatcgtga ggaccatctc caggaccaaa     660
gggccggccc gggagccgca ggtgtatgtc ctgccccac cccaggaaga gctcagcaaa     720
agcacggtca gcctcacctg catggtcacc agcttctacc cagactacat cgccgtggag    780
tggcagagaa acgggcagcc tgagtcggag gacaagtacg gcacgacccc gccccagctg    840
gacgccgaca gctcctactt cctgtacagc aagctcaggg tggacaggaa cagctggcag    900
gaaggagaca cctacgcgtg tgtggtgatg cacgaggccc tgcacaatca ctacacgcag    960
aagtccacct ctaagtctgc gggtaaatga                                     990
```

```
<210> SEQ ID NO 31
<211> LENGTH: 990
<212> TYPE: DNA
<213> ORGANISM: Bos taurus

<400> SEQUENCE: 31
gcctccacca cagccccgaa agtctaccct ctgagttctt gctgcgggga caagtccagc     60
```

```
tccaccgtga ccctgggctg cctggtctcc agctacatgc ccgagccggt gaccgtgacc      120
tggaactcgg gtgccctgaa gagcggcgtg cacaccttcc cggccgtcct tcagtcctcc      180
gggctctact ctctcagcag catggtgacc gtgcccggca gcacctcagg aacccagacc      240
ttcacctgca acgtagccca cccggccagc agcaccaagg tggacaaggc tgttgatccc      300
agatgcaaaa caacctgtga ctgttgccca ccgcctgagc tccctggagg accctctgtc      360
ttcatcttcc caccgaaacc caaggacacc ctcacaatct cgggaacgcc cgaggtcacg      420
tgtgtggtgg tggacgtggg ccacgatgac cccgaggtga agttctcctg gttcgtggac      480
gacgtggagg taaacacagc cacgacgaag ccgagagagg agcagttcaa cagcacctac      540
cgcgtggtca gcgccctgcg catccagcac caggactgga ctggaggaaa ggagttcaag      600
tgcaaggtcc acaacgaagg cctcccagcc ccatcgtga ggaccatctc caggaccaaa      660
gggccggccc gggagccgca ggtgtatgtc ctggccccac ccaggaaga gctcagcaaa      720 agcacggtca gcctcacctg catggtcacc agcttctacc cagactacat cgccgtggag      780
tggcagagaa atgggcagcc tgagtcagag gacaagtacg gcacgacccc tccccagctg      840
gacgccgacg gctcctactt cctgtacagc aggctcaggg tggacaggaa cagctggcag      900
gaaggagaca cctacacgtg tgtggtgatg cacgaggccc tgcacaatca ctacacgcag      960
aagtccacct ctaagtctgc gggtaaatga                                        990

<210> SEQ ID NO 32
<211> LENGTH: 981
<212> TYPE: DNA
<213> ORGANISM: Bos taurus

<400> SEQUENCE: 32
gcctccacca cagccccgaa agtctaccct ctggcatcca gctgcggaga cacatccagc       60
tccaccgtga ccctgggctg cctggtgtcc agctacatgc ccgagccggt gaccgtgacc      120
tggaactcgg gtgccctgaa gagcggcgtg cacaccttcc cggctgtcct tcagtcctcc      180
gggctctact ctctcagcag catggtgacc gtgcccgcca gcagctcagg acagaccttc      240
acctgcaacg tagcccaccc ggccagcagc accaaggtgg acaaggctgt tggggtctcc      300
attgactgct ccaagtgtca taaccagcct tgcgtgaggg aaccatctgt cttcatcttc      360
ccaccgaaac ccaaagacac cctgatgatc acaggaacgc ccgaggtcac gtgtgtggtg      420
gtgaacgtgg ccacgataa ccccgaggtg cagttctcct ggttcgtgga tgacgtggag      480
gtgcacacgc caggtcgaa gccaagagag gagcagttca acagcacgta ccgcgtggtc      540
agcgccctgc ccatccagca ccaggactgg actggaggaa aggagttcaa gtgcaaggtc      600
aacaacaaag gcctctcggc cccatcgtga ggatcatct ccaggagcaa agggccggcc      660
cgggagccgc aggtgtatgt cctggaccca cccaaggaag agctcagcaa aagcacgctc      720
agcgtcacct gcatggtcac cggcttctac ccagaagatg tagccgtgga gtggcagaga      780
aaccggcaga ctgagtcgga ggacaagtac cgcacgaccc cgccccagct ggacaccgac      840
cgctcctact cctgtacag caagctcagg gtgacagga acagctggca ggaaggagac      900
gcctacacgt gtgtggtgat gcacgaggcc ctgcacaatc actacatgca gaagtccacc      960
tctaagtctg cgggtaaatg a                                                981

<210> SEQ ID NO 33
<211> LENGTH: 981
<212> TYPE: DNA
```

<213> ORGANISM: Bos taurus

<400> SEQUENCE: 33

| | | | | | |
|---|---|---|---|---|---|
| gcctccacca | cagccccgaa | agtctaccct | ctgagttctt | gctgcgggga | caagtccagc | 60
| tccaccgtga | ccctgggctg | cctggtgtcc | agctacatgc | ccgagccggt | gaccgtgacc | 120
| tggaactcgg | gtgccctgaa | gagcggcgtg | cacaccttcc | cggccgtcct | tcagtcctcc | 180
| gggctctact | ctctcagcag | catggtgacc | gtgcccggca | gcacctcagg | acagaccttc | 240
| acctgcaacg | tagcccaccc | ggccagcagc | accaaggtgg | acaaggctgt | ggggtctcc | 300
| agtgactgct | ccaagcctaa | taaccagcat | tgcgtgaggg | aaccatctgt | cttcatcttc | 360
| ccaccgaaac | ccaaagacac | cctgatgatc | acaggaacgc | ccgaggtcac | gtgtgtggtg | 420
| gtgaacgtgg | ccacgataa | ccccgaggtg | cagttctcct | ggttcgtgga | cgacgtggag | 480
| gtgcacacgg | ccaggacgaa | gccgagagag | gagcagttca | cagcacgta | ccgcgtggtc | 540
| agcgccctgc | ccatccagca | ccaggactgg | actggaggaa | aggagttcaa | gtgcaaggtc | 600
| aacatcaaag | gcctctcggc | ctccatcgtg | aggatcatct | ccaggagcaa | agggccggcc | 660
| cgggagccgc | aggtgtatgt | cctggaccca | cccaaggaag | agctcagcaa | agcacggtc | 720
| agcgtcacct | gcatggtcat | cggcttctac | ccagaagatg | tagacgtgga | gtggcagaga | 780
| gaccggcaga | ctgagtcgga | ggacaagtac | cgcacgaccc | cgccccagct | ggacgccgac | 840
| cgctcctact | tcctgtacag | caagctcagg | gtggacagga | acagctggca | gagaggagac | 900
| acctacacgt | gtgtggtgat | gcacgaggcc | ctgcacaatc | actacatgca | gaagtccacc | 960
| tctaagtctg | cgggtaaatg | a | | | | 981

<210> SEQ ID NO 34
<211> LENGTH: 984
<212> TYPE: DNA
<213> ORGANISM: Bos taurus

<400> SEQUENCE: 34

| | | | | | |
|---|---|---|---|---|---|
| gcctccacca | cagccccgaa | agtctaccct | ctgagttctt | gctgcgggga | caagtccagc | 60
| tcggggtga | ccctgggctg | cctggtctcc | agctacatgc | ccgagccggt | gaccgtgacc | 120
| tggaactcgg | gtgccctgaa | gagcggcgtg | cacaccttcc | cggccgtcct | tcagtcctcc | 180
| gggctctact | ctctcagcag | catggtgacc | gtgcccgcca | gcagctcagg | aacccagacc | 240
| ttcacctgca | acgtagccca | cccggccagc | agcaccaagg | tggacaaggc | tgttggggtc | 300
| tccagtgact | gctccaagcc | taataaccag | cattgcgtga | gggaaccatc | tgtcttcatc | 360
| ttcccaccga | aacccaaaga | caccctgatg | atcacaggaa | cgcccgaggt | cacgtgtgtg | 420
| gtggtgaacg | tgggccacga | taaccccgag | gtgcagttct | cctggttcgt | ggacgacgtg | 480
| gaggtgcaca | cggccaggac | gaagccgaga | gaggagcagt | tcaacagcac | gtaccgcgtg | 540
| gtcagcgccc | tgcccatcca | gcaccaggac | tggactggag | aaaggagtt | caagtgcaag | 600
| gtcaacatca | aaggcctctc | ggcctccatc | gtgaggatca | tctccaggag | caaagggccg | 660
| gcccgggagc | cgcaggtgta | tgtcctggac | ccacccaagg | aagagctcag | caaaagcacg | 720
| gtcagcctca | cctgcatggt | catcggcttc | tacccagaag | atgtagacgt | ggagtggcag | 780
| agagaccggc | agactgagtc | ggaggacaag | taccgcacga | ccccgcccca | gctggacgcc | 840
| gaccgctcct | acttcctgta | cagcaagctc | agggtggaca | ggaacagctg | gcagagagga | 900
| gacacctaca | cgtgtgtggt | gatgcacgag | gccctgcaca | atcactacat | gcagaagtcc | 960
| acctctaagt | ctgcgggtaa | atga | | | | 984

<210> SEQ ID NO 35
<211> LENGTH: 1059
<212> TYPE: DNA
<213> ORGANISM: Bos taurus

<400> SEQUENCE: 35

```
gcctccacca cagccccgaa agtctaccct ctggcatcca gctgcggaga cacatccagc      60
tccaccgtga ccctgggctg cctggtctcc agctacatgc ccgagccggt gaccgtgacc     120
tggaactcgg gtgccctgaa gagcggcgtg cacaccttcc cggccgtccg gcagtcctct     180
gggctgtact ctctcagcag catggtgact gtgcccgcca gcagctcaga aacccagacc     240
ttcacctgca acgtagccca cccggccagc agcaccaagg tggacaaggc tgtcactgca     300
aggcgtccag tcccgacgac gccaaagaca actatccctc ctggaaaacc cacaaccca     360
aagtctgaag ttgaaaagac ccctgccag tgttccaaat gcccagaacc tctgggagga     420
ctgtctgtct tcatcttccc accgaaaccc aaggacaccc tcacaatctc gggaacgccc     480
gaggtcacgt gtgtggtggt ggacgtgggc caggatgacc ccgaggtgca gttctcctgg     540
ttcgtggacg acgtggaggt gcacacggcc aggacgaagc cgagagagga gcagttcaac     600
agcacctacc gcgtggtcag cgccctgcgc atccagcacc aggactggct gcagggaaag     660
gagttcaagt gcaaggtcaa caacaaaggc ctcccggccc ccattgtgag gaccatctcc     720
aggaccaaag ggcaggcccg ggagccgcag gtgtatgtcc tggccccacc ccgggaagag     780
ctcagcaaaa gcacgctcag cctcacctgc ctgatcaccg gtttctaccc agaagagata     840
gacgtggagt ggcagagaaa tgggcagcct gagtcggagg acaagtacca cacgaccgca     900
ccccagctgg atgctgacgg ctcctacttc ctgtacagca gctcaggggt gaacaagagc     960
agctggcagg aaggagacca ctacacgtgt gcagtgatgc acgaagcttt acggaatcac    1020
tacaaagaga agtccatctc gaggtctccg ggtaaatga                            1059
```

<210> SEQ ID NO 36
<211> LENGTH: 1059
<212> TYPE: DNA
<213> ORGANISM: Bos taurus

<400> SEQUENCE: 36

```
gcctccacca cagccccgaa agtctaccct ctggcatccc gctgcggaga cacatccagc      60
tccaccgtga ccctgggctg cctggtctcc agctacatgc ccgagccggt gaccgtgacc     120
tggaactcgg gtgccctgaa gagtggcgtg cacaccttcc cggccgtcct tcagtcctcc     180
gggctgtact ctctcagcag catggtgacc gtgcccgcca gcacctcaga aacccagacc     240
ttcacctgca acgtagccca cccggccagc agcaccaagg tggacaaggc tgtcactgca     300
aggcgtccag tcccgacgac gccaaagaca accatccctc ctggaaaacc cacaacccag     360
gagtctgaag ttgaaaagac ccctgccag tgttccaaat gcccagaacc tctgggagga     420
ctgtctgtct tcatcttccc accgaaaccc aaggacaccc tcacaatctc gggaacgccc     480
gaggtcacgt gtgtggtggt ggacgtgggc caggatgacc ccgaggtgca gttctcctgg     540
ttcgtggacg acgtggaggt gcacacggcc aggacgaagc cgagagagga gcagttcaac     600
agcacctacc gcgtggtcag cgccctgcgc atccagcacc aggactggct gcagggaaag     660
gagttcaagt gcaaggtcaa caacaaaggc ctcccggccc ccattgtgag gaccatctcc     720
aggaccaaag ggcaggcccg ggagccgcag gtgtatgtcc tggccccacc ccgggaagag     780
```

```
ctcagcaaaa gcacgctcag cctcacctgc ctgatcaccg gtttctaccc agaagagata    840
gacgtggagt ggcagagaaa tgggcagcct gagtcggagg acaagtacca cacgaccgca    900
ccccagctgg atgctgacgg ctcctacttc ctgtacagca ggctcagggt gaacaagagc    960
agctggcagg aaggagacca ctacacgtgt gcagtgatgc atgaagcttt acggaatcac   1020
tacaaagaga agtccatctc gaggtctccg ggtaaatga                         1059
```

<210> SEQ ID NO 37
<211> LENGTH: 331
<212> TYPE: PRT
<213> ORGANISM: Ovis aries

<400> SEQUENCE: 37

```
Ala Ser Thr Thr Pro Pro Lys Val Tyr Pro Leu Thr Ser Cys Cys Gly
1               5                   10                  15

Asp Thr Ser Ser Ser Ile Val Thr Leu Gly Cys Leu Val Ser Ser Tyr
            20                  25                  30

Met Pro Glu Pro Val Thr Val Thr Trp Asn Ser Gly Ala Leu Thr Ser
        35                  40                  45

Gly Val His Thr Phe Pro Ala Ile Leu Gln Ser Ser Gly Leu Tyr Ser
    50                  55                  60

Leu Ser Ser Val Val Thr Val Pro Ala Ser Thr Ser Gly Ala Gln Thr
65                  70                  75                  80

Phe Ile Cys Asn Val Ala His Pro Ala Ser Ser Thr Lys Val Asp Lys
                85                  90                  95

Arg Val Glu Pro Gly Cys Pro Asp Pro Cys Lys His Cys Arg Cys Pro
            100                 105                 110

Pro Pro Glu Leu Pro Gly Gly Pro Ser Val Phe Ile Phe Pro Pro Lys
        115                 120                 125

Pro Lys Asp Thr Leu Thr Ile Ser Gly Thr Pro Glu Val Thr Cys Val
    130                 135                 140

Val Val Asp Val Gly Gln Asp Asp Pro Glu Val Gln Phe Ser Trp Phe
145                 150                 155                 160

Val Asp Asn Val Glu Val Arg Thr Ala Arg Thr Lys Pro Arg Glu Glu
                165                 170                 175

Gln Phe Asn Ser Thr Phe Arg Val Val Ser Ala Leu Pro Ile Gln His
            180                 185                 190

Gln Asp Trp Thr Gly Gly Lys Glu Phe Lys Cys Lys Val His Asn Glu
        195                 200                 205

Ala Leu Pro Ala Pro Ile Val Arg Thr Ile Ser Arg Thr Lys Gly Gln
    210                 215                 220

Ala Arg Glu Pro Gln Val Tyr Val Leu Ala Pro Pro Gln Glu Glu Leu
225                 230                 235                 240

Ser Lys Ser Thr Leu Ser Val Thr Cys Leu Val Thr Gly Phe Tyr Pro
                245                 250                 255

Asp Tyr Ile Ala Val Glu Trp Gln Lys Asn Gly Gln Pro Glu Ser Glu
            260                 265                 270

Asp Lys Tyr Gly Thr Thr Thr Ser Gln Leu Asp Ala Asp Gly Ser Tyr
        275                 280                 285

Phe Leu Tyr Ser Arg Leu Arg Val Asp Lys Asn Ser Trp Gln Glu Gly
    290                 295                 300

Asp Thr Tyr Ala Cys Val Val Met His Glu Ala Leu His Asn His Tyr
305                 310                 315                 320

Thr Gln Lys Ser Ile Ser Lys Pro Pro Gly Lys
                325                 330
```

<210> SEQ ID NO 38
<211> LENGTH: 996
<212> TYPE: DNA
<213> ORGANISM: Ovis aries

<400> SEQUENCE: 38

```
gcctcaacaa caccccgaa agtctaccct ctgacttctt gctgcgggga cacgtccagc      60
tccatcgtga ccctgggctg cctggtctcc agctatatgc ccgagccggt gaccgtgacc     120
tggaactctg gtgccctgac cagcggcgtg cacaccttcc cggccatcct gcagtcctcc     180
gggctctact ctctcagcag cgtggtgacc gtgccggcca gcacctcagg agcccagacc     240
ttcatctgca acgtagccca cccggccagc agcaccaagg tggacaagcg tgttgagccc     300
ggatgcccgg acccatgcaa acattgccga tgcccacccc ctgagctccc cggaggaccg     360
tctgtcttca tcttcccacc gaaacccaag gacacccta caatctctgg aacgcccgag     420
gtcacgtgtg tggtggtgga cgtgggccag gatgaccccg aggtgcagtt ctcctggttc     480
gtggacaacg tggaggtgcg cacggccagg acaaagccga gaggagca gttcaacagc      540
accttccgcg tggtcagcgc cctgcccatc agcaccaag actggactgg aggaaaggag     600
ttcaagtgca aggtccacaa cgaagccctc ccggccccca tcgtgaggac catctccagg     660
accaaagggc aggcccggga ccgcaggtg tacgtcctgg ccccaccca ggaagagctc      720
agcaaaagca cgctcagcgt cacctgcctg gtcaccggct tctacccaga ctacatcgcc     780
gtggagtggc agaaaaatgg gcagcctgag tcggaggaca gtacggcac gaccacatcc      840
cagctggacg ccgacggctc ctacttcctg tacagcaggc tcagggtgga caagaacagc     900
tggcaagaag agacaccta cgcgtgtgtg gtgatgcacg aggctctgca caaccactac     960
acacagaagt cgatctctaa gcctccgggt aaatga                              996
```

<210> SEQ ID NO 39
<211> LENGTH: 329
<212> TYPE: PRT
<213> ORGANISM: Ovis aries

<400> SEQUENCE: 39

```
Ala Ser Thr Thr Ala Pro Lys Val Tyr Pro Leu Thr Ser Cys Cys Gly
1               5                   10                  15

Asp Thr Ser Ser Ser Ser Ile Val Thr Leu Gly Cys Leu Val Ser
            20                  25                  30

Ser Tyr Met Pro Glu Pro Val Thr Val Thr Trp Asn Ser Gly Ala Leu
        35                  40                  45

Thr Ser Gly Val His Thr Phe Pro Ala Ile Leu Gln Ser Ser Gly Leu
    50                  55                  60

Tyr Ser Leu Ser Ser Val Val Thr Val Pro Ala Ser Thr Ser Gly Ala
65                  70                  75                  80

Gln Thr Phe Ile Cys Asn Val Ala His Pro Ala Ser Ser Ala Lys Val
                85                  90                  95

Asp Lys Arg Val Gly Ile Ser Ser Asp Tyr Ser Lys Cys Ser Lys Pro
            100                 105                 110

Pro Cys Val Ser Arg Pro Ser Val Phe Ile Phe Pro Pro Lys Pro Lys
        115                 120                 125

Asp Ser Leu Met Ile Thr Gly Thr Pro Glu Val Thr Cys Val Val Val
    130                 135                 140
```

Asp Val Gly Gln Gly Asp Pro Glu Val Gln Phe Ser Trp Phe Val Asp
145                 150                 155                 160

Asn Val Glu Val Arg Thr Ala Arg Thr Lys Pro Arg Glu Glu Gln Phe
                165                 170                 175

Asn Ser Thr Phe Arg Val Val Ser Ala Leu Pro Ile Gln His Asp His
            180                 185                 190

Trp Thr Gly Gly Lys Glu Phe Lys Cys Lys Val His Ser Lys Gly Leu
        195                 200                 205

Pro Ala Pro Ile Val Arg Thr Ile Ser Arg Ala Lys Gly Gln Ala Arg
    210                 215                 220

Glu Pro Gln Val Tyr Val Leu Ala Pro Pro Gln Glu Glu Leu Ser Lys
225                 230                 235                 240

Ser Thr Leu Ser Val Thr Cys Leu Val Thr Gly Phe Tyr Pro Asp Tyr
                245                 250                 255

Ile Ala Val Glu Trp Gln Arg Ala Arg Gln Pro Glu Ser Glu Asp Lys
            260                 265                 270

Tyr Gly Thr Thr Thr Ser Gln Leu Asp Ala Asp Gly Ser Tyr Phe Leu
        275                 280                 285

Tyr Ser Arg Leu Arg Val Asp Lys Ser Ser Trp Gln Arg Gly Asp Thr
    290                 295                 300

Tyr Ala Cys Val Val Met His Glu Ala Leu His Asn His Tyr Thr Gln
305                 310                 315                 320

Lys Ser Ile Ser Lys Pro Pro Gly Lys
                325

<210> SEQ ID NO 40
<211> LENGTH: 990
<212> TYPE: DNA
<213> ORGANISM: Ovis aries

<400> SEQUENCE: 40

```
gcctccacca cagccccgaa agtctaccct ctgacttctt gctgcgggga cacgtccagc      60
tccagctcca tcgtgaccct gggctgcctg gtctccagct atatgcccga gccggtgacc     120
gtgacctgga actctggtgc cctgaccagc ggcgtgcaca ccttcccggc catcctgcag     180
tcctccgggc tctactctct cagcagcgtg gtgaccgtgc cggccagcac ctcaggagcc     240
cagaccttca tctgcaacgt agcccacccg gccagcagcg ccaaggtgga caagcgtgtt     300
gggatctcca gtgactactc caagtgttct aaaccgcctt gcgtgagccg accgtctgtc     360
ttcatcttcc ccccgaaacc caaggacagc ctcatgatca caggaacgcc cgaggtcacg     420
tgtgtggtgg tggacgtggg ccagggtgac cccgaggtgc agttcctcctg gttcgtggac   480
aacgtggagg tgcgcacggc caggacaaag ccgagagagg agcagttcaa cagcaccttc     540
cgcgtggtca gcgccctgcc catccagcac gaccactgga ctggaggaaa ggagttcaag     600
tgcaaggtcc acagcaaagg cctcccggcc ccatcgtga ggaccatctc cagggccaaa     660
gggcaggccc gggagccgca ggtgtacgtc ctggccccac cccaggaaga gctcagcaaa     720
agcacgctca gcgtcacctg cctggtcacc ggcttctacc cagactacat cgccgtggag     780
tggcagagag cgcggcagcc tgagtcggag acaagtacg gcacgaccac atcccagctg      840
gacgccgacg gctcctactt cctgtacagc aggctcaggg tggacaagag cagctggcaa     900
agaggagaca cctacgcgtg tgtggtgatg cacgaggctc tgcacaacca ctacacacag     960
aagtcgatct ctaagcctcc gggtaaatga                                      990
```

<210> SEQ ID NO 41
<211> LENGTH: 102
<212> TYPE: PRT
<213> ORGANISM: Ovis aries

<400> SEQUENCE: 41

Pro Ser Val Phe Leu Phe Lys Pro Ser Glu Glu Gln Leu Arg Thr Gly
1               5                   10                  15

Thr Val Ser Val Val Cys Leu Val Asn Asp Phe Tyr Pro Lys Asp Ile
            20                  25                  30

Asn Val Lys Val Lys Val Asp Gly Val Thr Gln Asn Ser Asn Phe Gln
        35                  40                  45

Asn Ser Phe Thr Asp Gln Asp Ser Lys Lys Ser Thr Tyr Ser Leu Ser
    50                  55                  60

Ser Thr Leu Thr Leu Ser Ser Ser Glu Tyr Gln Ser His Asn Ala Tyr
65                  70                  75                  80

Ala Cys Glu Val Ser His Lys Ser Leu Pro Thr Ala Leu Val Lys Ser
                85                  90                  95

Phe Asn Lys Asn Glu Cys
            100

<210> SEQ ID NO 42
<211> LENGTH: 309
<212> TYPE: DNA
<213> ORGANISM: Ovis aries

<400> SEQUENCE: 42
ccatccgtct tcctcttcaa accatctgag gaacagctga ggaccggaac tgtctctgtc      60
gtgtgcttgg tgaatgattt ctaccccaaa gatatcaatg tcaaggtgaa agtggatggg    120
gttacccaga acagcaactt ccagaacagc ttcacagacc aggacagcaa gaaaagcacc    180
tacagcctca gcagcaccct gacactgtcc agctcagagt accagagcca taacgcctat    240
gcgtgtgagg tcagccacaa gagcctgccc accgccctcg tcaagagctt caataagaat    300
gaatgttag                                                            309

<210> SEQ ID NO 43
<211> LENGTH: 106
<212> TYPE: PRT
<213> ORGANISM: Ovis aries

<400> SEQUENCE: 43

Gly Gln Pro Lys Ser Ala Pro Ser Val Thr Leu Phe Pro Pro Ser Thr
1               5                   10                  15

Glu Glu Leu Ser Thr Asn Lys Ala Thr Val Val Cys Leu Ile Asn Asp
            20                  25                  30

Phe Tyr Pro Gly Ser Val Asn Val Val Trp Lys Ala Asp Gly Ser Thr
        35                  40                  45

Ile Asn Gln Asn Val Lys Thr Thr Gln Ala Ser Lys Gln Ser Asn Ser
    50                  55                  60

Lys Tyr Ala Ala Ser Ser Tyr Leu Thr Leu Thr Gly Ser Glu Trp Lys
65                  70                  75                  80

Ser Lys Ser Ser Tyr Thr Cys Glu Val Thr His Glu Gly Ser Thr Val
                85                  90                  95

Thr Lys Thr Val Lys Pro Ser Glu Cys Ser
            100                 105

<210> SEQ ID NO 44

```
<211> LENGTH: 321
<212> TYPE: DNA
<213> ORGANISM: Ovis aries

<400> SEQUENCE: 44
ggtcagccca agtccgcacc ctcggtcacc ctgttcccgc cttccacgga ggagctcagt    60
accaacaagg ccaccgtggt gtgtctcatc aacgacttct acccgggtag cgtgaacgtg   120
gtctggaagg cagatggcag caccatcaat cagaacgtga agaccaccca ggcctccaaa   180
cagagcaaca gcaagtacgc ggccagcagc tacctgaccc tgacgggcag cgagtggaag   240
tctaagagca gttacacctg cgaggtcacg cacgagggga gcaccgtgac gaagacagtg   300
aagccctcag agtgttctta g                                             321

<210> SEQ ID NO 45
<211> LENGTH: 266
<212> TYPE: PRT
<213> ORGANISM: Bubalus bulalis

<400> SEQUENCE: 45
```

Ser Gly Val His Thr Phe Pro Ala Val Leu Gln Ser Ser Gly Leu Tyr
1               5                   10                  15

Ser Leu Ser Ser Thr Val Thr Ala Pro Ala Ser Ala Thr Lys Ser Gln
            20                  25                  30

Thr Phe Thr Cys Asn Val Ala His Pro Ala Ser Ser Thr Lys Val Asp
        35                  40                  45

Lys Ala Val Val Pro Pro Cys Arg Pro Lys Pro Cys Asp Cys Cys Pro
    50                  55                  60

Pro Pro Glu Leu Pro Gly Gly Pro Ser Val Phe Ile Phe Pro Pro Lys
65                  70                  75                  80

Pro Lys Asp Thr Leu Thr Ile Ser Gly Thr Pro Glu Val Thr Cys Val
                85                  90                  95

Val Val Asp Val Gly His Asp Asp Pro Glu Val Lys Phe Ser Trp Phe
            100                 105                 110

Val Asp Asp Val Glu Val Asn Thr Ala Arg Thr Lys Pro Arg Glu Glu
        115                 120                 125

Gln Phe Asn Ser Thr Tyr Arg Val Val Ser Ala Leu Pro Ile Gln His
    130                 135                 140

Asn Asp Trp Thr Gly Gly Lys Glu Phe Lys Cys Lys Val Tyr Asn Glu
145                 150                 155                 160

Gly Leu Pro Ala Pro Ile Val Arg Thr Ile Ser Arg Thr Lys Gly Gln
                165                 170                 175

Ala Arg Glu Pro Gln Val Tyr Val Leu Ala Pro Pro Gln Asp Glu Leu
            180                 185                 190

Ser Lys Ser Thr Val Ser Ile Thr Cys Met Val Thr Gly Phe Tyr Pro
        195                 200                 205

Asp Tyr Ile Ala Val Glu Trp Gln Lys Asp Gly Gln Pro Glu Ser Glu
    210                 215                 220

Asp Lys Tyr Gly Thr Thr Pro Pro Gln Leu Asp Ser Asp Gly Ser Tyr
225                 230                 235                 240

Phe Leu Tyr Ser Arg Leu Arg Val Asn Lys Asn Ser Trp Gln Glu Gly
                245                 250                 255

Gly Ala Tyr Thr Cys Val Val Met His Glu
            260                 265

```
<210> SEQ ID NO 46
```

```
<211> LENGTH: 801
<212> TYPE: DNA
<213> ORGANISM: Bubalus bubalis

<400> SEQUENCE: 46
gagcggcgtg cacaccttcc cggccgtcct tcagtcctcc gggctctact ctctcagcag      60
cacggtgacc gcgcccgcca gcgccacaaa aagccagacc ttcacctgca acgtagccca     120
cccggccagc agcaccaagg tggacaaggc tgttgttccc ccatgcagac cgaaaccctg     180
tgattgctgc ccacccctg agctccccgg aggaccctct gtcttcatct tcccaccaaa     240
acccaaggac accctcacaa tctctggaac tcctgaggtc acgtgtgtgg tggtggacgt     300
gggccacgat gaccccgagg tgaagttctc ctggttcgtg gacgatgtgg aggtaaacac     360
agccaggacg aagccaagag aggagcagtt caacagcacc taccgcgtgg tcagcgccct     420
gcccatccag cacaacgact ggactggagg aaaggagttc aagtgcaagg tctacaatga     480
aggcctccca gcccccatcg tgaggaccat ctccaggacc aaagggcagg cccgggagcc     540
gcaggtgtac gtcctggccc cacccccagga cgagctcagc aaaagcacgg tcagcatcac     600
ttgcatggtc actggcttct acccagacta catcgccgta gagtggcaga agatgggca      660 gcctgagtca gaggacaaat atggcacgac cccgccccag ctggacagcg atggctccta     720
cttcctgtac agcaggctca gggtgaacaa gaacagctgg caagaaggag gcgcctacac     780
gtgtgtagtg atgcatgagg c                                               801
```

```
<210> SEQ ID NO 47
<211> LENGTH: 309
<212> TYPE: PRT
<213> ORGANISM: Bubalus buballis

<400> SEQUENCE: 47

Ala Ser Ile Thr Ala Pro Lys Val Tyr Pro Leu Thr Ser Cys Arg Gly
 1               5                  10                  15

Glu Thr Ser Ser Thr Val Thr Leu Gly Cys Leu Val Ser Ser Tyr
                20                  25                  30

Met Pro Glu Pro Val Thr Val Thr Trp Asn Ser Gly Ala Leu Lys Ser
            35                  40                  45

Gly Val His Thr Phe Pro Ala Val Leu Gln Ser Ser Gly Leu Tyr Ser
        50                  55                  60

Leu Ser Ser Thr Val Thr Ala Pro Ala Ser Ala Thr Lys Ser Gln Thr
65                  70                  75                  80

Phe Thr Cys Asn Val Ala His Pro Ala Ser Ser Thr Lys Val Asp Thr
                85                  90                  95

Ala Val Gly Phe Ser Ser Asp Cys Cys Lys Phe Pro Lys Pro Cys Val
            100                 105                 110

Arg Gly Pro Ser Val Phe Ile Phe Pro Pro Lys Pro Lys Asp Thr Leu
        115                 120                 125

Met Ile Thr Gly Asn Pro Glu Val Thr Cys Val Val Val Asp Val Gly
    130                 135                 140

Arg Asp Asn Pro Glu Val Gln Phe Ser Trp Phe Val Gly Asp Val Glu
145                 150                 155                 160

Val His Thr Gly Arg Ser Lys Pro Arg Glu Glu Gln Phe Asn Ser Thr
                165                 170                 175

Tyr Arg Val Val Ser Thr Leu Pro Ile Gln His Asn Asp Trp Thr Gly
            180                 185                 190

Gly Lys Glu Phe Lys Cys Lys Val Asn Asn Lys Gly Leu Pro Ala Pro
```

```
            195                 200                 205
Ile Val Arg Thr Ile Ser Arg Thr Lys Gly Gln Ala Arg Glu Pro Gln
    210                 215                 220

Val Tyr Val Leu Ala Pro Pro Gln Glu Glu Leu Ser Lys Ser Thr Val
225                 230                 235                 240

Ser Val Thr Cys Met Val Thr Gly Phe Tyr Pro Asp Tyr Ile Ala Val
                245                 250                 255

Glu Trp His Arg Asp Arg Gln Ala Glu Ser Glu Asp Lys Tyr Arg Thr
            260                 265                 270

Thr Pro Pro Gln Leu Asp Ser Asp Gly Ser Tyr Phe Leu Tyr Ser Arg
        275                 280                 285

Leu Lys Val Asn Lys Asn Ser Trp Gln Glu Gly Gly Ala Tyr Thr Cys
    290                 295                 300

Val Val Met His Glu
305

<210> SEQ ID NO 48
<211> LENGTH: 929
<212> TYPE: DNA
<213> ORGANISM: Bubalus bubalis

<400> SEQUENCE: 48
gcctccatca cagccccgaa agtctaccct ctgacttctt gccgcgggga aacgtccagc      60
tccaccgtga ccctgggctg cctggtctcc agctacatgc ccgagccggt gaccgtgacc     120
tggaactcgg gtgccctgaa gagcggcgtg cacaccttcc cggccgtcct tcagtccctc     180
gggctctact ctctcagcag cacggtgacc gcgcccgcca gcgccacaaa aagccagacc     240
ttcacctgca acgtagccca ccggccagc agcaccaagg tggacacggc tgttgggttc     300
tccagtgact gctgcaagtt tcctaagcct tgtgtgaggg gaccatctgt cttcatcttc     360
ccgccgaaac ccaaagacac cctgatgatc acaggaaatc ccgaggtcac atgtgtggtg     420
gtggacgtgg gccgggataa ccccgaggtg cagttctcct ggttcgtggg tgatgtggag     480
gtgcacacgg gcaggtcgaa gccgagagag gagcagttca acagcaccta ccgcgtggtc     540
agcaccctgc ccatccagca caatgactgg actggaggaa aggagttcaa gtgcaaggtc     600
aacaacaaag gcctcccagc ccccatcgtg aggaccatct ccaggaccaa agggcaggcc     660
cgggagccgc aggtgtacgt cctggcccca ccccaggaag agctcagcaa aagcacggtc     720
agcgtcactt gcatggtcac tggcttctac ccagactaca tcgccgtaga gtggcataga     780
gaccggcagg ctgagtcgga ggacaagtac cgcacgaccc cgccccagct ggacagcgat     840
ggctcctact cctgtacag caggctcaag gtgaacaaga acagctggca agaaggaggc     900
gcctacacgt gtgtagtgat gcatgaggc                                       929

<210> SEQ ID NO 49
<211> LENGTH: 352
<212> TYPE: PRT
<213> ORGANISM: Bubalus bubalis

<400> SEQUENCE: 49

Ala Ser Thr Thr Ala Pro Lys Val Tyr Pro Leu Ala Ser Cys Gly
1               5                  10                  15

Asp Thr Ser Ser Ser Thr Val Thr Leu Gly Cys Leu Val Ser Ser Tyr
            20                  25                  30

Met Pro Glu Pro Val Thr Val Thr Trp Asn Ser Gly Ala Leu Lys Asn
        35                  40                  45
```

Gly Val His Thr Phe Pro Ala Val Arg Gln Ser Ser Gly Leu Tyr Ser
    50                  55                  60

Leu Ser Ser Met Val Thr Met Pro Thr Ser Thr Ala Gly Thr Gln Thr
65                  70                  75                  80

Phe Thr Cys Asn Val Ala His Pro Ala Ser Ser Thr Lys Val Asp Thr
                85                  90                  95

Ala Val Thr Ala Arg His Pro Val Pro Lys Thr Pro Glu Thr Pro Ile
            100                 105                 110

His Pro Val Lys Pro Pro Thr Gln Glu Pro Arg Asp Glu Lys Thr Pro
        115                 120                 125

Cys Gln Cys Pro Lys Cys Pro Glu Pro Leu Gly Gly Leu Ser Val Phe
    130                 135                 140

Ile Phe Pro Pro Lys Pro Lys Asp Thr Leu Thr Ile Ser Gly Thr Pro
145                 150                 155                 160

Glu Val Thr Cys Val Val Asp Val Gly Gln Asp Pro Glu Val
                165                 170                 175

Gln Phe Ser Trp Phe Val Asp Asp Val Glu Val His Thr Ala Arg Met
            180                 185                 190

Lys Pro Arg Glu Glu Gln Phe Asn Ser Thr Tyr Arg Val Val Ser Ala
        195                 200                 205

Leu Pro Ile Gln His Gln Asp Trp Leu Arg Glu Lys Glu Phe Lys Cys
    210                 215                 220

Lys Val Asn Asn Lys Gly Leu Pro Ala Pro Ile Val Arg Thr Ile Ser
225                 230                 235                 240

Arg Thr Lys Gly Gln Ala Arg Glu Pro Gln Val Tyr Val Leu Ala Pro
                245                 250                 255

Pro Arg Glu Glu Leu Ser Lys Ser Thr Leu Ser Leu Thr Cys Leu Ile
            260                 265                 270

Thr Gly Phe Tyr Pro Glu Glu Val Asp Val Glu Trp Gln Arg Asn Gly
        275                 280                 285

Gln Pro Glu Ser Glu Asp Lys Tyr His Thr Thr Pro Pro Gln Leu Asp
    290                 295                 300

Ala Asp Gly Ser Tyr Phe Leu Tyr Ser Arg Leu Arg Val Asn Arg Ser
305                 310                 315                 320

Ser Trp Gln Glu Gly Asp His Tyr Thr Cys Ala Val Met His Glu Ala
                325                 330                 335

Leu Arg Asn His Tyr Lys Glu Lys Pro Ile Ser Arg Ser Pro Gly Lys
            340                 345                 350

<210> SEQ ID NO 50
<211> LENGTH: 1059
<212> TYPE: DNA
<213> ORGANISM: Bubalus bubalis

<400> SEQUENCE: 50
gcctccacca cagccccgaa agtctaccct ctggcatcca gctgcgggga cacgtccagc      60
tccaccgtga ccctgggctg cctggtctcc agctacatgc ccgagccggt gaccgtgacc     120
tggaactcgg gtgccctgaa gaacggcgtg cacaccttcc cggccgtccg gcagtcctcc     180
gggctctact ctctcagcag catggtgacc atgcccacca gcaccgcagg aacccagacc     240
ttcacctgca acgtagccca cccggccagc agcaccaagg tggacacggc tgtcactgca     300
aggcatccgg tcccgaagac accagagaca cctatccatc ctgtaaaacc cccaacccag     360
gagcccagag atgaaaagac accctgccag tgtcccaaat gcccagaacc tctgggagga     420

```
ctgtctgtct tcatcttccc accgaaaccc aaggacaccc tcacaatctc tggaacgccc    480
gaggtcacgt gtgtggtggt ggacgtgggc caggatgacc ccgaagtgca gttctcctgg    540
ttcgtggatg acgtggaggt gcacacagcc aggatgaagc caagagagga gcagttcaac    600
agcacctacc gcgtggtcag cgccctgccc atccagcacc aggactggct gcgggaaaag    660
gagttcaagt gcaaggtcaa caacaaaggc ctcccggccc ccatcgtgag gaccatctcc    720
aggaccaaag ggcaggcccg ggagccacag gtgtatgtcc tggccccacc ccgggaagag    780
ctcagcaaaa gcacgctcag cctcacctgc ctaatcaccg gcttctaccc agaagaggta    840
gacgtggagt ggcagagaaa tggcagcct gagtcagagg acaagtacca cacgacccca    900
ccccagctgg acgctgacgg ctcctacttc ctgtacagca ggctcagggt gaacaggagc    960
agctggcagg aaggagacca ctacacgtgt gcagtgatgc atgaagcttt acggaatcac   1020
tacaaagaga agcccatctc gaggtctccg ggtaaatga                          1059
```

<210> SEQ ID NO 51
<211> LENGTH: 105
<212> TYPE: PRT
<213> ORGANISM: Bubalus bubalis

<400> SEQUENCE: 51

```
Gln Pro Lys Ser Ala Pro Ser Val Thr Leu Phe Pro Pro Ser Thr Glu
1               5                   10                  15

Glu Leu Ser Ala Asn Lys Ala Thr Leu Val Cys Leu Ile Ser Asp Phe
            20                  25                  30

Tyr Pro Gly Ser Met Thr Val Ala Arg Lys Ala Asp Gly Ser Thr Ile
        35                  40                  45

Thr Arg Asn Val Glu Thr Thr Arg Ala Ser Lys Gln Ser Asn Ser Lys
    50                  55                  60

Tyr Ala Ala Ser Ser Tyr Leu Ser Leu Thr Gly Ser Glu Trp Lys Ser
65                  70                  75                  80

Lys Gly Ser Tyr Ser Cys Glu Val Thr His Glu Gly Ser Thr Val Thr
                85                  90                  95

Lys Thr Val Lys Pro Ser Glu Cys Ser
            100                 105
```

<210> SEQ ID NO 52
<211> LENGTH: 318
<212> TYPE: DNA
<213> ORGANISM: Bubalus bubalis

<400> SEQUENCE: 52

```
cagcccaagt ccgcaccctc agtcaccctg ttcccaccct ccacggagga gctcagcgcc     60
aacaaggcca ccctggtgtg tctcatcagc gacttctacc cgggtagcat gaccgtggcc    120
aggaaggcag acggcagcac catcacccgg aacgtggaga ccacccgggc ctccaaacag    180
agcaacagca agtacgcggc cagcagctac ctgagcctga cgggcagcga gtggaaatcg    240
aaaggcagtt acagctgcga ggtcacgcac gaggggagca ccgtgacaaa gacagtgaag    300
ccctcagagt gttcttag                                                  318
```

<210> SEQ ID NO 53
<211> LENGTH: 229
<212> TYPE: PRT
<213> ORGANISM: Homo sapiens

<400> SEQUENCE: 53

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
            210                 215                 220

Leu Ser Leu Gly Lys
225

<210> SEQ ID NO 54
<211> LENGTH: 690
<212> TYPE: DNA
<213> ORGANISM: Homo sapiens

<400> SEQUENCE: 54
gagtccaaat atggtccccc atgcccatca tgcccagcac ctgagttcct ggggggacca      60
tcagtcttcc tgttcccccc aaacccaag gacactctca tgatctcccg gacccctgag     120
gtcacgtgcg tggtggtgga cgtgagccag gaagacccg aggtccagtt caactggtac     180
gtggatggcg tggaggtgca taatgccaag acaaagccgc gggaggagca gttcaacagc     240
acgtaccgtg tggtcagcgt cctcaccgtc ctgcaccagg actggctgaa cggcaaggag     300
tacaagtgca aggtctccaa caaaggcctc ccgtcctcca tcgagaaaac catctccaaa     360
gccaaagggc agccccgaga gccacaggtg tacaccctgc ccccatccca ggaggagatg     420
accaagaacc aggtcagcct gacctgcctg gtcaaaggct tctacccag cgacatcgcc     480 gtggagtggg agagcaatgg gcagccggag aacaactaca agaccacgcc tcccgtgctg     540
gactccgacg gctccttctt cctctacagc aggctaaccg tggacaagag caggtggcag     600
gaggggaatg tcttctcatg ctccgtgatg catgaggctc tgcacaacca ctacacacag     660
aagagcctct ccctgtctct gggtaaatga                                      690
```

<210> SEQ ID NO 55
<211> LENGTH: 229
<212> TYPE: PRT
<213> ORGANISM: Homo sapiens

<400> SEQUENCE: 55

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 56
<211> LENGTH: 690
<212> TYPE: DNA
<213> ORGANISM: Homo sapiens

<400> SEQUENCE: 56
gagtccaaat atggtccccc gtgcccatca tgcccagcac ctgagttcct ggggggacca      60
tcagtcttcc tgttcccccc aaaacccaag gacactctca tgatctcccg gacccctgag    120
gtcacgtgcg tggtggtgga cgtgagccag gaagacccg aggtccagtt caactggtac     180
gtggatggcg tggaggtgca taatgccaag acaaagccgc gggaggagca gttcaacagc    240
acgtaccgtg tggtcagcgt cctcaccgtc gtgcaccagg actggctgaa cggcaaggag    300
tacaagtgca aggtctccaa caaaggcctc ccgtcctcca tcgagaaaac catctccaaa    360
gccaaagggc agccccgaga gccacaggtg tacaccctgc ccccatccca ggaggagatg    420
accaagaacc aggtcagcct gacctgcctg gtcaaaggct tctacccag cgacatcgcc     480 gtggagtggg agagcaatgg gcagccggag aacaactaca agaccacgcc tcccgtgctg    540
gactccgacg gctccttctt cctctacagc aggctaaccg tggacaagag caggtggcag    600
gaggggaatg tcttctcatg ctccgtgatg catgaggctc tgcacaacca ctacacgcag    660
aagagcctct ccctgtctct gggtaaatga    690

<210> SEQ ID NO 57
<211> LENGTH: 217
<212> TYPE: PRT
<213> ORGANISM: Homo sapiens

<400> SEQUENCE: 57

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 58
<211> LENGTH: 654
<212> TYPE: DNA
<213> ORGANISM: Homo sapiens

<400> SEQUENCE: 58
gcacctgagt tcctgggggg accatcagtc ttcctgttcc ccccaaaacc caaggacact    60
ctcatgatct cccggacccc tgaggtcacg tgcgtggtgg tggacgtgag ccaggaagac    120
cccgaggtcc agttcaactg gtacgtggat ggcgtggagg tgcataatgc caagacaaag    180
ccgcgggagg agcagttcaa cagcacgtac cgtgtggtca gcgtcctcac cgtcctgcac    240
caggactggc tgaacggcaa ggagtacaag tgcaaggtct ccaacaaagg cctcccgtcc    300
tccatcgaga aaaccatctc caaagccaaa gggcagcccc gagagccaca ggtgtacacc    360
ctgcccccat cccaggagga gatgaccaag aaccaggtca gcctgacctg cctggtcaaa    420
ggcttctacc ccagcgacat cgccgtggag tgggagagca atgggcagcc ggagaacaac    480

```
tacaagacca cgcctcccgt gctggactcc gacggctcct tcttcctcta cagcaagctc    540
accgtggaca agagcaggtg gcaggagggg aacgtcttct catgctccgt gatgcatgag    600
gctctgcaca accactacac gcagaagagc ctctccctgt ctctgggtaa atga          654
```

<210> SEQ ID NO 59
<211> LENGTH: 106
<212> TYPE: PRT
<213> ORGANISM: Homo sapiens

<400> SEQUENCE: 59

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 60
<211> LENGTH: 321
<212> TYPE: DNA
<213> ORGANISM: Homo sapiens

<400> SEQUENCE: 60

```
actgtggctg caccatctgt cttcatcttc ccgccatctg atgagcagtt gaaatctgga    60
actgcctctg ttgtgtgcct gctgaataac ttctatccca gagaggccaa agtacagtgg    120
aaggtggata acgcccTcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gctcgcccgt cacaaagagc    300
ttcaacaggg gagagtgtta g                                              321
```

<210> SEQ ID NO 61
<211> LENGTH: 29
<212> TYPE: DNA
<213> ORGANISM: Artificial Sequence
<220> FEATURE:
<223> OTHER INFORMATION: primer

<400> SEQUENCE: 61

```
gaaagatcta tgctgtggga ggcttggtt                                       29
```

<210> SEQ ID NO 62
<211> LENGTH: 29
<212> TYPE: DNA
<213> ORGANISM: Artificial Sequence
<220> FEATURE:
<223> OTHER INFORMATION: primer

<400> SEQUENCE: 62

```
ccggaattcg ggttgctctg gctgcagct                                       29
```

```
<210> SEQ ID NO 63
<211> LENGTH: 37
<212> TYPE: DNA
<213> ORGANISM: Artificial Sequence
<220> FEATURE:
<223> OTHER INFORMATION: primer

<400> SEQUENCE: 63
ctagctagcc gcccaccatg ctgtgggagg cttggtt                    37

<210> SEQ ID NO 64
<211> LENGTH: 29
<212> TYPE: DNA
<213> ORGANISM: Artificial Sequence
<220> FEATURE:
<223> OTHER INFORMATION: primer

<400> SEQUENCE: 64
tgcatgcatc agaacagcta ggttgtacg                             29

<210> SEQ ID NO 65
<211> LENGTH: 21
<212> TYPE: DNA
<213> ORGANISM: Artificial Sequence
<220> FEATURE:
<223> OTHER INFORMATION: primer

<400> SEQUENCE: 65
atgctgtggg aggcttggtt c                                     21

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
tcagggatgc tctggctgca                                       20

<210> SEQ ID NO 67
<211> LENGTH: 25
<212> TYPE: DNA
<213> ORGANISM: Artificial Sequence
<220> FEATURE:
<223> OTHER INFORMATION: primer

<400> SEQUENCE: 67
atgctgtggg aggctcagtt ccagg                                 25

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
tcagggttgc tccggctgca                                       20

<210> SEQ ID NO 69
<211> LENGTH: 29
<212> TYPE: DNA
<213> ORGANISM: Artificial Sequence
<220> FEATURE:
<223> OTHER INFORMATION: primer
```

<400> SEQUENCE: 69
attgagctca tgctgtggga ggcttggtt                                             29

<210> SEQ ID NO 70
<211> LENGTH: 28
<212> TYPE: DNA
<213> ORGANISM: Artificial Sequence
<220> FEATURE:
<223> OTHER INFORMATION: primer

<400> SEQUENCE: 70
aatgaattcg ggatgctctg gctgcagc                                              28

<210> SEQ ID NO 71
<211> LENGTH: 516
<212> TYPE: PRT
<213> ORGANISM: Bos taurus

<400> SEQUENCE: 71

Met Leu Trp Glu Ala Trp Phe Gln Val Trp Leu Phe Leu Gln Leu Leu
1               5                   10                  15

Trp Ala Ala Ala Val Glu Ala Pro Glu Pro Gly Ala Glu Val Pro Val
            20                  25                  30

Val Trp Ala Gln Glu Gly Ala Pro Ala Gln Leu Pro Cys Ser Pro Thr
        35                  40                  45

Ile Pro Leu Gln Asp Leu Ser Leu Pro Arg Thr Arg Gln Val Thr Trp
    50                  55                  60

Gln His Val Pro Glu Ser Gly Ser Ala Ala Pro Thr Pro Arg Gly Pro
65                  70                  75                  80

Gly Pro Arg Arg Tyr Thr Val Leu Arg Leu Ala Pro Gly Gly Leu Arg
                85                  90                  95

Ile Gly Lys Leu Pro Leu Gln Pro Arg Val Gln Leu Glu Glu Met Gly
            100                 105                 110

Leu Gln Arg Gly Asp Phe Ser Leu Trp Leu Arg Pro Ala Arg Arg Ala
        115                 120                 125

Asp Ala Gly Glu Tyr His Ala Ala Val Arg Phe Gly Asn Arg Ala Leu
    130                 135                 140

Ala Cys Arg Leu Arg Leu Arg Val Gly Gln Ala Ala Val Thr Ala Ser
145                 150                 155                 160

Pro Pro Gly Pro Leu Trp Thr Ser Ser Trp Val Val Leu Asn Cys Ser
                165                 170                 175

Phe Ser Arg Pro Asp Leu Pro Ala Ser Val His Trp Phe Arg Gly Pro
            180                 185                 190

Gly Arg Val Pro Val Gln Glu Ser Pro His His Leu Val Gly Asn
        195                 200                 205

Phe Leu Phe Leu Pro Gln Val Ser Ser Leu Asp Ser Gly Thr Trp Gly
    210                 215                 220

Cys Ser Leu Thr Tyr Arg Asp Gly Phe Asn Val Ser Ile Thr Tyr Asn
225                 230                 235                 240

Leu Ala Val Leu Gly Leu Glu Pro Arg Ala Thr Leu Thr Val Tyr Ala
                245                 250                 255

Gly Ala Gly Ser Lys Val Glu Leu Pro Cys Arg Leu Pro Pro Gly Val
            260                 265                 270

Gly Ile Gln Ser Ser Leu Thr Ala Met Trp Thr Pro Pro Gly Glu Gly
        275                 280                 285

```
Pro Asp Leu Leu Val Ala Gly Asp Arg Asn Asn Phe Thr Leu Arg Leu
    290                 295                 300
Glu Ala Val Gly Gln Ala Gln Ala Gly Thr Tyr Thr Cys Arg Val His
305                 310                 315                 320
Leu Gln Gly Arg Gln Leu Ser Ala Thr Val Thr Leu Ala Val Ile Thr
                325                 330                 335
Val Thr Pro Lys Pro Tyr Gly Ser Ser Gly Ser Leu Arg Lys Pro Phe
            340                 345                 350
Cys Glu Val Thr Pro Ala Ser Gly Gln Glu Arg Phe Val Trp Ser Pro
        355                 360                 365
Leu Asp Lys Arg Ser Gln Arg Arg Ser Pro Gly Pro Trp Leu Leu Thr
    370                 375                 380
Pro Asp Ala Arg Pro Leu Ser Gln Pro Trp Gln Cys His Leu Tyr Gln
385                 390                 395                 400
Gly Glu Arg Leu Leu Gly Thr Ala Val Tyr Leu Thr Glu Leu Ser His
                405                 410                 415
Pro Gly Ala Gln Arg Ser Gly Arg Ala Leu Gly Ala Gly Arg Thr Ala
            420                 425                 430
His Leu Pro Leu Leu Ile Leu Gly Leu Leu Phe Leu Leu Leu Leu Val
        435                 440                 445
Thr Gly Ala Ser Ser Phe His Leu Trp Arg Arg Gln Trp Arg Pro Arg
    450                 455                 460
Arg Phe Ser Ala Leu Glu His Gly Thr His Pro Ser Gln Ala Ser Ser
465                 470                 475                 480
Lys Thr Gly Glu Leu Glu Pro Glu Leu Glu Pro Glu Pro Asp Pro Glu
                485                 490                 495
Val Glu Pro Glu Pro Glu Pro Glu Pro Glu Ser Gln Pro Gln Leu Gln
            500                 505                 510
Pro Glu Gln Pro
        515

<210> SEQ ID NO 72
<211> LENGTH: 29
<212> TYPE: PRT
<213> ORGANISM: Bos taurus

<400> SEQUENCE: 72

Gly Ser Ala Ala Pro Thr Pro Arg Gly Pro Gly Pro Arg Tyr Thr
1               5                   10                  15

Val Leu Arg Leu Ala Pro Gly Gly Leu Arg Ile Gly Lys
            20                  25
```

ANTI-LAG-3 ANTIBODY

PRIORITY APPLICATIONS

This application is a U.S. National Stage Filing under 35 U.S.C. 371 from International Application No. PCT/JP2017/029057, filed on Aug. 10, 2017, and published as WO2018/034227 on Feb. 22, 2018, which claims the benefit of priority to Japanese Application No. 2016-159091, filed on Aug. 15, 2016; the benefit of priority of each of which is hereby claimed herein, and which applications and publication are hereby incorporated herein by reference in their entirety.

TECHNICAL FIELD

The present invention relates to an anti-LAG-3 antibody. More specifically, the present invention relates to an anti-LAG-3 antibody comprising a variable region containing complementarity-determining regions (CDR) of a rat anti-bovine LAG-3 antibody and a constant region of an antibody of an animal other than rat.

BACKGROUND ART

Lymphocyte activation gene 3 (LAG-3), an immunoinhibitory receptor, was identified as a molecule closely related to CD4 (Non-Patent Document No. 1: Triebel F, Jitsukawa S, Baixeras E, Roman-Roman S. Genevee C, Viegas-Pequignot E, Hercend T. J. Exp. Med., 171(5):1393-1405; May 1, 1990). Recently, it has been elucidated that this molecule is involved in immunosuppression in chronic infections and tumors (Non-Patent Document No. 2: Blackburn S D, Shin H, Haining W N, Zou T, Workman C J, Polley A, Betts M R, Freeman G J, Vignali D A, Wherry E J. Nat. Immunol., 10(1):29-37; Nov. 30, 2008; Non-Patent Document No. 3 Woo S-R, Turnis M E, Goldberg M V., Bankoti J, Selby M, Nirschl C J, Bettini M L, Gravano D M, Vogel P, Liu C L, Tangsombatvisit S, Grosso J F, Netto G, Smeltzer M P, Chaux A, Utz P J, Workman C J, Pardoll D M, Korman A J. Drake C G, Vignali D A A. Cancer Res., 72(4):917-927; Feb. 15, 2012). In the field of human medical care, an antibody drug that inhibits the effect of LAG-3 has been developed as an immunotherapeutic drug for tumors and its phase I clinical trial is under progress (name of the antibody: BMS-986016; Bristle-Myers Squibb and Ono Pharmaceutical Co., Ltd.)

To date, the present inventors have been developing an immunotherapy for animal refractory diseases targeting LAG-3, and have revealed that this novel immunotherapy is applicable to multiple-diseases and multiple-animals. (Non-Patent Document No. 4: Shirai T, Konnai S. Ikebuchi R, Okagawa T, Suzuki S, Sunden Y. Onuma M, Murata S, Ohashi K. Vet. Immunol. Immunopathol., 144(3-4):462-467; Dec. 15, 2011; Non-Patent Document No. 5: Konnai S, Suzuki S, Shirai T, Ikebuchi R, Okagawa T, Sunden Y, Mingala C N, Onuma M. Murata S, Ohashi K. Comp. Immunol. Microbiol. Infect. Dis., 36(1):63-69; January 2013; Non-Patent Document No. 6: Okagawa T, Konnai S, Nishimori A. Ikebuchi R. Mizorogi S, Nagata R, Kawaji S, Tanaka S, Kagawa Y. Murata S, Mori Y, Ohashi K. Infect. Immun. 84(1):77-89; Oct. 19, 2015.)

However, the antibodies which the present inventors have prepared to date are rat antibodies, and therefore it is impossible to administer those antibodies repeatedly to animals other than rat.

PRIOR ART LITERATURE

Non-Patent Documents

Non-Patent Document No. 1: Triebel F. Jitsukawa S, Baixeras E, Roman-Roman S, Genevee C, Viegas-Pequignot E. Hercend T. J. Exp. Med., 171(5):1393-1405; May 1, 1990.

Non-Patent Document No. 2: Blackburn S D, Shin H. Haining W N, Zou T. Workman C J, Polley A, Betts M R, Freeman G J, Vignali D A, Wherry E J. Nat. Immunol., 10(1):29-37; Nov. 30, 2008.

Non-Patent Document No. 3: Woo S-R, Turnis M E, Goldberg M V., Bankoti J. Selby M, Nirschl C J, Bettini M L, Gravano D M, Vogel P. Liu C L, Tangsombatvisit S, Grosso J F, Netto G, Smeltzer M P, Chaux A. Utz P J, Workman C J, Pardoll D M, Korman A J, Drake C G, Vignali D A A. Cancer Res., 72(4):917-927; Feb. 15, 2012.

Non-Patent Document No. 4: Shirai T, Konnai S. Ikebuchi R. Okagawa T, Suzuki S. Sunden Y, Onuma M, Murata S, Ohashi K. Vet. Immunol. Immunopathol., 144(3-4):462-467; Dec. 15, 2011.

Non-Patent Document No. 5: Konnai S. Suzuki S, Shirai T. Ikebuchi R, Okagawa T, Sunden Y. Mingala C N, Onuma M. Murata S, Ohashi K. Comp. Immunol. Microbiol. Infect. Dis., 36(1):63-69; January 2013.

Non-Patent Document No. 6: Okagawa T, Konnai S, Nishimori A. Ikebuchi R, Mizorogi S, Nagata R, Kawaji S, Tanaka S. Kagawa Y. Murata S, Mori Y, Ohashi K. Infect. Immun. 84(1):77-89; Oct. 19, 2015.

DISCLOSURE OF THE INVENTION

Problem for Solution by the Invention

It is an object of the present invention to provide an anti-LAG-3 antibody capable of repeated administration even to animals other than rat.

Means to Solve the Problem

The present inventors have determined the variable regions of a rat anti-bovine LAG-3 monoclonal antibody (2D8) binding to bovine LAG-3 expressing Cos-7 cells, and then combined genes encoding the resultant variable regions with genes encoding the constant regions of a bovine immunoglobulin (bovine IgG1, with mutations having been introduced into the putative binding sites of Fcγ receptors in CH2 domain in order to inhibit ADCC activity; see FIG. 1 for amino acid numbers and mutations: 247 E→P, 248 L→V, 249 P→A, 250 G→deletion, 344 A→S, 345 P→S; Ikebuchi R, Konnai S, Okagawa T, Yokoyama K, Nakajima C, Suzuki Y, Murata S, Ohashi K. Immunology 2014 August; 142(4): 551-561) to thereby obtain a chimeric antibody gene. This gene was introduced into Chinese hamster ovary cells (CHO cells). By culturing/proliferating the resultant cells, the present inventors have succeeded in preparing a rat-bovine chimeric anti-bovine LAG-3 antibody. Further, the present inventors have determined the CDRs of the variable regions of rat anti-bovine LAG-3 monoclonal antibody (2D8). The present invention has been achieved based on these findings.

A summary of the present invention is as described below.

(1) An anti-LAG-3 antibody comprising (a) a light chain comprising a light chain variable region containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region of an antibody of an animal other than rat; and (b) a heavy chain comprising a heavy chain variable region containing CDR1 having the amino acid sequence of GFDFDTYP (SEQ ID NO: 18), CDR2 having the amino acid sequence of ITIKTHNYAT (SEQ ID NO: 19) and CDR3 having the amino acid sequence of NREDFDY (SEQ ID NO: 20) and the heavy chain constant region of an antibody of an animal other than rat.

(2) The antibody of (1) above, wherein the light chain variable region and the heavy chain variable region are derived from rat.

(3) The antibody of (2) above, wherein the light chain variable region is the light chain variable region of a rat anti-bovine LAG-3 antibody and the heavy chain variable region is the heavy chain variable region of a rat anti-bovine LAG-3 antibody.

(4) The antibody of (3) above, wherein the light chain variable region has the amino acid sequence as shown in SEQ ID NO. 1 and the heavy chain variable region has the amino acid sequence as shown in SEQ ID NO: 2.

(5) The antibody of any one of (1) to (4) above, wherein the light chain constant region of an antibody of an animal other than rat has the amino acid sequence of the constant region of lambda chain or kappa chain.

(6) The antibody of any one of (1) to (5) above, wherein the heavy chain constant region of an antibody of an animal other than rat has the amino acid sequence of the constant region of an immunoglobulin equivalent to human IgG4 or said amino acid sequence having mutations introduced thereinto that reduce ADCC activity and/or CDC activity.

(7) The antibody of (6) above, wherein the animal other than rat is bovine; the light chain constant region of the bovine antibody has the amino acid sequence of the constant region of lambda chain; and the heavy chain constant region of the bovine antibody has mutations introduced thereinto that reduce ADCC activity and/or CDC activity.

(8) The antibody of (7) above, wherein the light chain constant region of the bovine antibody has the amino acid sequence as shown in SEQ ID NO: 3 and the heavy chain constant region of the bovine antibody has the amino acid sequence as shown in SEQ ID NO: 4.

(9) The antibody of any one of (1) to (8) above which has a four-chain structure comprising two light chains and two heavy chains.

(10) A pharmaceutical composition comprising the antibody of any one of (1) to (9) above as an active ingredient.

(11) The composition of (10) above for prevention and/or treatment of cancers and/or infections.

(12) The composition of (11) above, wherein the cancers and/or infections are selected from the group consisting of neoplastic diseases, leukemia, Johne's disease, anaplasmosis, bacterial mastitis, mycotic mastitis, mycoplasma infections (such as mycoplasma mastitis, mycoplasma pneumonia or the like), tuberculosis, *Theileria orientalis* infection, cryptosporidiosis, coccidiosis, trypanosomiasis and leishmaniasis.

(13) An artificial genetic DNA comprising (a') a DNA encoding a light chain comprising a light chain variable region containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region of an antibody of an animal other than rat; and (b') a DNA encoding a heavy chain comprising a heavy chain variable region containing CDR1 having the amino acid sequence of GFDFDTYP (SEQ ID NO: 18). CDR2 having the amino acid sequence of ITIKTHNYAT (SEQ ID NO: 19) and CDR3 having the amino acid sequence of NREDFDY (SEQ ID NO: 20) and the heavy chain constant region of an antibody of an animal other than rat.

(14) A vector comprising the artificial genetic DNA of (13) above.

(15) A host cell transformed with the vector of (14) above.

(16) A method of preparing an antibody, comprising culturing the host cell of (15) above and collecting an anti-LAG-3 antibody from the resultant culture.

(17) A DNA encoding a light chain comprising a light chain variable region containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region of an antibody of an animal other than rat.

(18) A DNA encoding a heavy chain comprising a heavy chain variable region containing CDR1 having the amino acid sequence of GFDFDTYP (SEQ ID NO: 18), CDR2 having the amino acid sequence of ITIKTHNYAT (SEQ ID NO: 19) and CDR3 having the amino acid sequence of NREDFDY (SEQ ID NO: 20) and the heavy chain constant region of an antibody of an animal other than rat.

The present specification encompasses the contents disclosed in the specifications and/or drawings of Japanese Patent Application No. 2016-159091 based on which the present patent application claims priority.

Effect of the Invention

According to the present invention, a novel anti-LAG-3 antibody has been obtained. This antibody is applicable even to those animals other than rat.

BRIEF DESCRIPTION OF THE DRAWINGS

FIG. 1 The amino acid sequence of rat-bovine chimeric anti-bovine LAG-3 antibody ch2D8. CDR1, CDR2 and CDR3 regions in the light chain variable region and the heavy chain variable region of rat anti-bovine LAG-3 antibody 2D8 are shown. Further, amino acids introduced as mutations to bovine IgG1 (CH2 domain) are also shown (amino acid numbers and mutations: 247 E→P, 248 L→V, 249 P→A, 250 G→deletion, 344 A→S, 345 P→S).

BEST MODES FOR CARRYING OUT THE INVENTION

Figure 2:
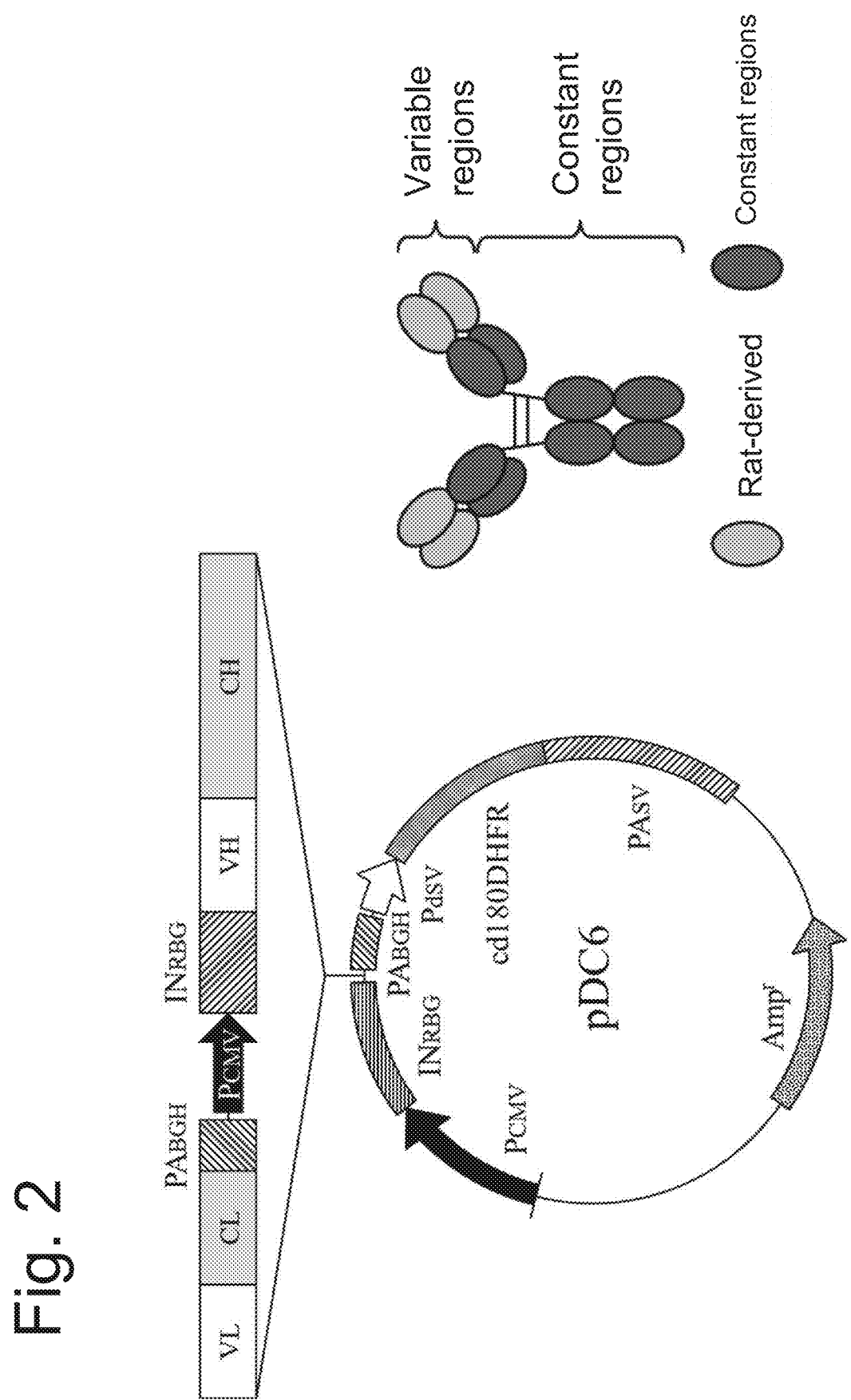
FIG. 2 Schematic drawings of pDC6 vector and rat-bovine chimeric anti-bovine LAG-3 antibody ch2D8.

Hereinbelow, the present invention will be described in detail.

The present invention provides an anti-LAG-3 antibody comprising (a) a light chain comprising a light chain variable region containing CDR1 having the amino acid sequence of QSLLDSDGNTY (SEQ ID NO: 16). CDR2 having the amino acid sequence of SVS and CDR3 having the amino acid sequence of MQATHVPFT (SEQ ID NO: 17) and the light chain constant region of an antibody of an animal other than rat; and (b) a heavy chain comprising a heavy chain variable region containing CDR1 having the amino acid sequence of GFDFDTYP (SEQ ID NO: 18), CDR2 having the amino acid sequence of ITIKTHNYAT (SEQ ID NO: 19) and CDR3 having the amino acid sequence of NREDFDY (SEQ ID NO: 20) and the heavy chain constant region of an antibody of an animal other than rat.

CDR1, CDR2 and CDR3 in the light chain variable region (VL) of rat anti-bovine LAG-3 antibody 2D8 are a region consisting of the amino acid sequence of QSLLDSDGNTY (SEQ ID NO: 16), a region consisting of the amino acid sequence of SVS and a region consisting of the amino acid sequence of MQATHVPFT (SEQ ID NO: 17), respectively (see FIG. 1).

Further, CDR1, CDR2 and CDR3 in the heavy chain variable region (VH) of rat anti-bovine LAG-3 antibody 2D8 are a region consisting of the amino acid sequence of GFDFDTYP (SEQ ID NO: 18), a region consisting of the amino acid sequence of ITIKTHNYAT (SEQ ID NO: 19) and a region consisting of the amino acid sequence of NREDFDY (SEQ ID NO: 20), respectively (see FIG. 1).

In the amino acid sequences of QSLLDSDGNTY (SEQ ID NO: 16), SVS and MQATHVPFT (SEQ ID NO: 17), as well as the amino acid sequences of GFDFDTYP (SEQ ID NO: 18). ITIKTHNYAT (SEQ ID NO: 19) and NREDFDY (SEQ ID NO: 20), one, two, three, four or five amino acids may be deleted, substituted or added. Even when such mutations have been introduced, the resulting amino acid sequences are capable of having the function as a CDR of VL or a CDR of VH of the LAG-3 antibody.

As used herein, the term "antibody" is a concept encompassing not only full-length antibodies but also antibodies of smaller molecular sizes such as Fab, F(ab)'$_2$, ScFv, Diabody, $V_H$, $V_L$, Sc(Fv)$_2$. Bispecific sc(Fv)$_2$, Minibody, scFv-Fc monomer and scFv-Fc dimer.

In the anti-LAG-3 antibody of the present invention, VL and VH thereof may be derived from rat. For example, VL thereof may be the VL of a rat anti-bovine LAG-3 antibody, and VH thereof may be the VH of the rat anti-bovine LAG-3 antibody.

The amino acid sequence of the VL and the amino acid sequence of the VH of the rat anti-bovine LAG-3 antibody are shown in SEQ ID NOS: 1 and 2, respectively. The amino acid sequences as shown in SEQ ID NOS: 1 and 2 may have deletion(s), substitution(s) or addition(s) of one or several (e.g., up to five, about 10 at the most) amino acids. Even when such mutations have been introduced, the resulting amino acid sequences are capable of having the function as VL or VH of the LAG-3 antibody.

There are two types of immunoglobulin light chain, which are called Kappa chain (K) and Lambda chain (λ). In the anti-LAG-3 antibody of the present invention, the light chain constant region (CL) of an antibody of an animal other than rat may have the amino acid sequence of the constant region of either Kappa chain or Lambda chain. However, the relative abundance of Lambda chain is higher in bovine, ovine, feline, canine and equine, and that of Kappa chain is higher in mouse, rat, human and porcine. Since a chain with a higher relative abundance is considered to be preferable, a bovine, ovine, feline, canine or equine antibody preferably has the amino acid sequence of the constant region of Lambda chain whereas a mouse, rat, human or porcine antibody preferably has the amino acid sequence of the constant region of Kappa chain (κ).

The heavy chain constant region (CH) of an antibody of an animal other than rat may have the amino acid sequence of the constant region of an immunoglobulin equivalent to human IgG4. Immunoglobulin heavy chain is classified into γ chain, μ chain, α chain, δ chain and ε chain depending on the difference in constant region. According to the type of heavy chain present, five classes (isotypes) of immunoglobulin are formed; they are IgG, IgM, IgA, IgD and IgE.

Immunoglobulin G (IgG) accounts for 70-75% of human immunoglobulins and is the most abundantly found monomeric antibody in plasma. IgG has a four-chain structure consisting of two light chains and two heavy chains. Human IgG1, IgG2 and IgG4 have molecular weights of about 146,000, whereas human IgG3 has a long hinge region that connects Fab region and Fc region and has a larger molecular weight of 170,000. Human IgG1 accounts for about 65%, human IgG2 about 25%, human IgG3 about 7%, and human IgG4 about 3% of human IgG. They are uniformly distributed inside and outside of blood vessels. Having a strong affinity for Fc receptors and complement factors on effector cell surfaces, human IgG1 induces antibody-dependent cell cytotoxicity (ADCC) and also activates complements to induce complement-dependent cell cytotoxicity (CDC). Human IgG2 and IgG4 are low at ADCC and CDC activities because their affinity for Fc receptors and complement factors is low.

Immunoglobulin M (IgM), which accounts for about 10% of human immunoglobulins, is a pentameric antibody consisting of five basic four-chain structures joined together. It has a molecular weight of 970.000. Usually occurring only in blood, IgM is produced against infectious microorganisms and takes charge of early stage immunity.

Immunoglobulin A (IgA) accounts for 10-15% of human immunoglobulins. It has a molecular weight of 160,000. Secreted IgA is a dimeric antibody consisting of two IgA molecules joined together. IgA1 is found in serum, nasal discharge, saliva and breast milk. In intestinal juice, IgA2 is found abundantly.

Immunoglobulin D (IgD) is a monomeric antibody accounting for no more than 1% of human immunoglobulins. IgD is found on B cell surfaces and involved in induction of antibody production.

Immunoglobulin E (IgE) is a monomeric antibody that occurs in an extremely small amount, accounting for only 0.001% or less of human immunoglobulins. Immunoglobulin E is considered to be involved in immune response to parasites but in advanced countries where parasites are rare, IgE is largely involved in bronchial asthma and allergy among other things.

With respect to canine, sequences of IgG-A (equivalent to human IgG2), IgG-B (equivalent to human IgG1), IgG-C (equivalent to human IgG3) and IgG-D (equivalent to human IgG4) have been identified as the heavy chain of IgG. In the antibody of the present invention, an IgG's heavy chain constant region with neither ADCC activity nor CDC activity is preferable (IgG4 in human). In the case where the constant region of an immunoglobulin equivalent to human IgG4 has not been identified, one may use a constant region that has lost both ADCC activity and CDC activity as a result of introducing mutations into the relevant region of an immunoglobulin equivalent to human IgG4.

With respect to bovine, sequences of IgG1, IgG2 and IgG3 have been identified as the heavy chain of IgG. In the antibody of the present invention, an IgG's heavy chain constant region with neither ADCC activity nor CDC activity is preferable (IgG4 in human). Although the constant region of wild-type human IgG1 has ADCC activity and CDC activity, it is known that these activities can be reduced by introducing amino acid substitutions or deletions into specific sites. In bovine, the constant region of an immunoglobulin equivalent to human IgG4 has not been identified, so mutations may be added at the relevant region of an immunoglobulin equivalent to human IgG1 and the resultant constant region then used. As one example, the amino acid sequence of the CH of a bovine antibody (IgG1 chain. GenBank: X62916) having mutations introduced into CH2 domain and a nucleotide sequence for such amino acid sequence (after codon optimization) are shown in SEQ ID NOS: 4 and 8, respectively.

When an animal other than rat is canine, an anti-LAG-3 antibody is more preferable in which (i) the CL of a canine antibody has the amino acid sequence of the constant region of Lambda chain and (ii) the CH of the canine antibody has the amino acid sequence of the constant region of an immunoglobulin equivalent to human IgG4.

When an animal other than rat is bovine, an anti-LAG-3 antibody is more preferable in which (i) the CL of a bovine antibody has the amino acid sequence of the constant region of Lambda chain and (ii) the CH of the bovine antibody has mutations introduced thereinto that reduce ADCC activity and/or CDC activity.

The anti-LAG-3 antibody of the present invention encompasses rat-bovine chimeric antibodies, bovinized antibodies and complete bovine-type antibodies. However, animals are not limited to bovine and may be exemplified by human, canine, porcine, simian, mouse, feline, equine, goat, sheep, water buffalo, rabbit, hamster, guinea pig and the like.

For example, the anti-LAG-3 antibody of the present invention may be an anti-LAG-3 antibody in which the CL of a bovine antibody has the amino acid sequence as shown in SEQ ID NO: 3 and the CH of the bovine antibody has the amino acid sequence as shown in SEQ ID NO: 4.

The amino acid sequences as shown in SEQ ID NOS: 3 and 4 may have deletion(s), substitution(s) or addition(s) of one or several (e.g., up to five, about 10 at the most) amino acids. Even when such mutations have been introduced, the resulting amino acid sequences are capable of having the function as CL or CH of the LAG-3 antibody.

The anti-LAG-3 antibody of the present invention may have a four-chain structure comprising two light chains and two heavy chains.

The anti-LAG-3 antibody of the present invention may be prepared as described below. Briefly, an artificial gene is synthesized which comprises (i) the identified variable region sequences of a rat anti-bovine LAG-3 antibody and (ii) the constant region sequences of an antibody of an animal other than rat (e.g., bovine) (preferably, an immunoglobulin equivalent to human IgG1, in which mutations have been introduced into the relevant region to reduce ADCC activity and/or CDC activity). The resultant gene is inserted into a vector (e.g., plasmid), which is then introduced into a host cell (e.g., mammal cell such as CHO cell). The host cell is cultured, and the antibody of interest is collected from the resultant culture.

The amino acid sequence and the nucleotide sequence of the VL of the rat anti-bovine LAG-3 antibody identified by the present inventors are shown in SEQ ID NOS: 1 and 5, respectively. Further, the nucleotide sequence after codon optimization is shown in SEQ ID NO: 11.

The amino acid sequence and the nucleotide sequence of the VH of the rat anti-bovine LAG-3 antibody identified by the present inventors are shown in SEQ ID NOS: 2 and 6, respectively. Further, the nucleotide sequence after codon optimization is shown in SEQ ID NO: 12.

The amino acid sequence and the nucleotide sequence of the CL (Lambda chain, GenBank: X62917) of a bovine antibody are shown in SEQ ID NOS: 3 and 7, respectively. Further, the nucleotide sequence after codon optimization is shown in SEQ ID NO: 13.

The amino acid sequence and the nucleotide sequence (after codon optimization) of the CH (IgG1 chain, modified from GenBank: X62916) of the bovine antibody are shown in SEQ ID NOS: 4 and 8, respectively.

Further. SEQ ID NO: 9 shows the amino acid sequence of a chimeric light chain consisting of the VL of the rat anti-bovine LAG-3 antibody and the CL (Lambda chain, GenBank: X62917) of the bovine antibody. The nucleotide sequence (after codon optimization) of the chimeric light chain consisting of the VL of the rat anti-bovine LAG-3 antibody and the CL (Lambda chain, GenBank: X62917) of the bovine antibody is shown in SEQ ID NO: 14.

SEQ ID NO: 10 shows the amino acid sequence of a chimeric heavy chain consisting of the VH of the rat anti-bovine LAG-3 antibody and the CH (IgG1 chain, modified from GenBank: X62916) of the bovine antibody. The nucleotide sequence (after codon optimization) of the chimeric heavy chain consisting of the VH of the rat anti-bovine LAG-3 antibody and the CH (IgG1 chain, modified from GenBank: X62916) of the bovine antibody is shown in SEQ ID NO: 15.

Amino acid sequences and nucleotide sequences of CLs and CHs for various animals other than rat may be obtained from known databases for use in the present invention.

Amino acid sequences and nucleotide sequences of bovine CLs and CHs are summarized in the table below. Table.

TABLE

| Species | Ig Domain | | Nucleotide Sequence | Amino Acid Sequence | GenBank Accession No. | IMGT Database | Reference |
|---|---|---|---|---|---|---|---|
| Bovine (Scientific Name Bos taurus) | Bovine Ig heavy chain constant region CH1–CH3 | IgG1 variant 1 | GCCTCCACCACCAGCCCGAAAGTCTACCCTCTGAGTTC TTGCTGCGGGACAAGTCCAGTCTCCACCGTGACCCTGG GCTGCCTGGTCTCCAGCTACATGCCCGAGCCGGTGACC GTGACCTGGAACTCGGGTGCCCTGAGCAGCGGCGTGCA CACCTTCCCGGCTGTCCTTCAGTCCTCCGGGCTGTACT CTCTCCAGCAGCATGGTGACCGTGCCCAGCAGCACTCA GGACAGACCTTCACCTGCAACGTAGCCCACCCCGGCCAG CAGCACCAAGGTGGACAAGGCTGTTGATCCCACCATGCA AACCATCACCCTGTGACTGTTGCCCACCCCTGAGTC CCGGAGCACCCCTGTCTGTCTTCATCTTCCCACCAAACC CAAGGACACCCTCACAATCTGGGAACGCCCCGAGGTCA CGTGTGTGTGGTGACGTGGGCCACGATGACCCCGAG GTGAAGTTCTCCTGGTTCGTGGACGGTGAAGGTAAA CACAGCCACGAGGCAGCAGGACCAGTTCAACA GCACCTACCGCGTGGTCAGCGCCCTGCGCATCAGCAC CAGGACTGGACTGGAGGAAAGGAGTTCAAGTGCAAGGT CCACAACGAAGGCCCCGGCCCCAGGCCCCGAGGACCA TCTCCAGGACCAAAGGGCCCTGGCCCCAGCAGCTCAGCGAA GTATGTCTCTGGCCCAGGAGACTCAGCAGTC GCAGGGTCAGCCTGCATGGTCACCAGCTTCTAC CCAGACTACATCGCCGTGGAGTGGCAGAGAAGGGCA GCCTGAGTCGGAGGACAAGTACCTACTTCCTGTACAGCAA GCTCAGGGTCGACGCCGACAGCTCCACTTCCTGTACAGCAA ACTACACCGTGTGTGATGCAGAAGGCCCTGCACCA TCACTACACGCAGAAGTCCACCTCTAAGTCTGCGGTA AATGA (SEQ ID NO: 29) | ASTTAPKVYPLSSCCGDKSSSTVTLGC LVSSYMPEPVTVTWNSGALKSGVHTFP AVLQSSGLYSLSSMVTVPGSTSGQTFT CNVAHPASSTKVDKAVDPTCKPSPCD CCPPPELPGGPSVFIFPPKPKDTLIISG TPEVTCVVVDVGHDDPEVKFSWFVDD VEVNTATTKPREEQFNSTYRVVSALRI QHQDWTGGKEFKCKVHNEGLPAPTVRT ISRTKGPAREPQVYVLAPPQEELSKST VSLTCMVTSFYPDYIAVEWQRNGQPES EDKYGTTPPQLDADSSYFLYSKLRVDR NSWQEGDTYTCVVMHEALHNHYTQKS TSKSAGK* (SEQ ID NO: 21) | X62916 | http://www. imgt.org/ IMGT repertoire/ index.php? section= LocusGenes& repertoire= genetable& species= bovine&group= IGHC | Symons DB et al., J Immogenet, 14, 273-283 (1987) PMID: 3141517 Symons DB et al., Mol Immunol., 841-850 (1989). PMID: 2513487 Kacskovica L. and Butler JE., Mol. Immunol., 33, 189-195 (1996). PMID: 3649440 Rabbani H. et al., Immuno-genetics, 46, 326-331 (1997). PMID: 9218535 Saini S.S. et al., Scand J. Immunol. 65, 32-8 (2007). PMID: 17212764 |
| | | IgG1 variant 2 | GCCTCCACCACCAGCCCGAAAGTCTACCCTCTGAGTTC TTGCTGCGGGACAAGTCCAGTCTCCACCGTGACCCTGG GCTGCCTGGTCTCCAGCTACATGCCCGAGCCGGTGACC GTGACCTGGAACTCGGGTGCCCTGAGCAGCGGCGTGCA CACCTTCCCGGCCGTCCTTCAGTCCTCCGGGCTGTACT CCTCCAGCAGCATGGTGACCGTGCCCAGCAGCACCTCA GGACAGACCTTCACCTGCAACGTAGCCCACCCCACCTCA CAGCACCAAGGTGGACAAGGCTGTTGATCCCACCATGCA AACCATCACCCTGTGACTGTTGCCTCATCTTCCCACCAAACC CCGGAGCACCCCTGTCTGTCTTCATCTTCCCACCAAACC CAAGGACACCCTCACAATCTGGGAACGCCCCGAGGTCA CGTGTGTGTGGTGACGTGGGCCACGATGACCCCGAG GTGAAGTTCTCCTGGTTCGTGGACGGTGAAGGTTCAACA GCACCTACCGCGTGGTCAGCGCCCTGCGCATCAGCAC CAGGACTGGACTGGAGGAAAGGAGTTCAAGTGCAAGGT CCACAACGAAGGCCCCGGCCCCAGGCCCCGAGGACCA TCTCCAGGACCAAAGGGCCCTGGCCCCAGCAGCTCAGCGAA GTATGTCTCTGGCCCAGGAGAAGCTCAGCAGTCA (SEQ ID NO: 22) | ASTTAPKVYPLSSCCGDKSSSTVTLGC LVSSYMPEPVTVTWNSGALKSGVHTFP AVLQSSGLYSLSSMVTVPGSTSGQTFT CNVAHPASSTKVDKAVDPTCKPSPCD CCPPPELPGGPSVFIFPPKPKDTLIISG TPEVTCVVVDVGHDDPEVKFSWFVDD VEVNTATTKPREEQFNSTYRVVSALRI QHQDWTGGKEFKCKVHNEGLPAPIVRT ISRTKGPAREPQVYVLAPPQEELSKST VSLTCMVTSFYPDYIAVEWQRNGQPES EDKYGTTPPQLDADSSYFLYSKLRVDR NSWQEGDTYTCVVMHEALHNHYTQKS TSKSAGK* (SEQ ID NO: 22) | X16701 (M25278) | | |

| Species | Ig Domain | Nucleotide Sequence | Amino Acid Sequence | GenBank Accession No. | IMGT Database Reference |
|---|---|---|---|---|---|
| | | GCACGGTCAGCTTCACCTGATGGTCACCAGCTTCTAC CCAGACTACATCGCCCTGAGGTGGCAGAGAAACGGGCA GCCTGAGTCGGAGGACAAGTACGGCAGACCCGCCC CAGCTGGACGCCCGACAGCTCCTACTTCCTGACAGCAA GCTCAGGGTGGACAGGAACAGCTGGCAGGAGGAGAC ACTTACACGTGTGTGATGCACGAGGCCCTGCACAA TCACTACACGCAGAAGTCCACCTCTAAGTCTGCGGGTA AATGA (SEQ ID NO: 30) | | | |
| | IgG1 variant 3 | GCCTCCACCACAGCCCCCGAAAGTCTACCCTCTGAGTTC TTGCTGCCAAGTGCGAGTCACTGCACCGAACCGTGG GCTGCCTGGTCTCCAGCTACATGCCCGAGCCGGTGACC GTGACCTGGAACTCGGGTGCCCTGAAGAGCGGCGTGCA CACCTTCCCGGCCGTCCTTCAGTCCTCCGGGCTCTACT CTCTCAGCAGCAGTGTGACCGTGCCACAGCTTCA GGAACCCAGACCTTCACCTGCAACGTAGCCCACCCGGC CAGCAGCACCAAGGTGGACAAGGCTGTTGATCCCAGAT GCAAAACAACTGTGACTGTTGCCCACCGCCTGAGCTC CCTGGAGGACCCCTCTGTCTTCATCTTCCCACCGAAACC CAAGGACACCCTCACAATCTCGGAACGCCCCGAGGTCA CGTGTGTGGTGGTGGACGTGGGCCACGATGAGGATCCCAG GTGAAGTTCTCCTGGTTCGTGACAGACGTGGAAGGTAAA CACAGCACGACGAAGCCGACGAGAGACAGTTCAACA GCACCTACCGCGTGGTCAGCGTGCTCGCCATCCAGCAC CAGGACTGGACTGGAGGAAAGGAGTTCAAGTGCAAGGT CCACAACGAAGCCTCCAGCCCCATCGTGAGGACCA TCTCCAGGACCAAAAGGCCGGCCGGAGCCCAGT GTATGTCTGGCCCACCCCAGGAAGCCTCAGCAAAA GCACGGTCAGCCTCACCTGCATGGTGGCAGCTTCTAC CCAGACTACATCGCCGTGAGTGGCAGAGAAATGGGCA GCCTGAGTCAGAGGACAAGTACGGCACGACCCTCCC AGCTGGACGCCCGACGGCTCCTACTTCCTGTACGACAGG CTCAGGGTGGACAGGAACAGCTGGCAGGAAGGAGACA CCTACACGTGTGGTGATGCACGAGGCCCTGCACAAT CACTACACGCAGAAGTCCACCTCTAAGTCTGCGGGTAA ATGA (SEQ ID NO: 31) | ASTTAPKVYPLSSCCGDKSSSTVTLGC LVSSYMPEPVTVTWNSGALKSGVHTFP AVLQSSGLYSLSSMVTVPGSTSGTQF TCNVAHPASSTKVDKAVDPRCKTTCD CCPPPELPGGPSVFIFPPKPKDTLTISG TPEVTCVVVDVGHDDPEVKFSWFVDD VEVNTATTKPREEQFNSTYRVVSALRI QHQDWTGGKEFKCKVHNEGLPAPIVRT ISRTKGPAREPQVYVLAPPQEELSKST VSLTCMWTSFYPDYIAVEWQRNGQPES EDKYGTTPPQLDADGSYFLYSRLRVDR NSWQEGDTYTCVVMHEALHNHYTQKS TSKSAGK* (SEQ ID NO: 23) | 582409 | |
| | IgG2 variant 1 | | ASTTAPKVYPLASSCGDTSSSTVTLGC LVSSYMPEPVTVTWNSGALKSGVHTFP AVLQSSGLYSLSSMVTVPASSSGQTFT CNVAHPASSTKVDKAVGVSIDCSKCHN QPCVREPSVFIFPPKPKDTLMITGTPEV TCVVVNGHDNPEVQFSWFVDDVEVH TARSKPREEQFNSTYRVVSALPIQHQD WTGGKEFKCKVNNKGLSAPIVRISRSK GPAREPQVYVLDPPKEELSKSTLSVTC MVTGFYPEDVAVEWQNRQTESEDKY RTTPPQLDTDRSYFLYSKLRVDRNSWQ EGDAYTCVVMHEALHNHYMQKSTSKS | 582407 | |

TABLE-continued

| Species | Ig Domain | Nucleotide Sequence | Amino Acid Sequence | GenBank Accession No. | IMGT Database Reference |
|---|---|---|---|---|---|
| | | TCCTGGTTCTGTGATGACGTGGAGGTGCACACGGCCAG GTCGAAGCCAAGAGAGGAGCAGTTCAACAGCACGTACC GCGTGGTCAGCGCCCTGCCCATCGAAGTGCAAGGACTGG ACTGAGGAGGAAAGGAGTTCAAGTGCAAGGTCAACAACAA AGGCCTCTGGGCCCCCATCGTGAGGATCATCTCCAGA GCAAAGGGCCGGCTCGGGAGCCGCAGGTGTATGTCCT GGACCCACCCCAAGGAAGACTCAGCAAAAGCACGCTCA GCGTCACCTGCATGGTCACCGGCTTCTACCCAGAAGAT GTAGCCGTGGAGTGGCAGAGAAACCGGCAGACTGAGTC GGAGGACAAGTACCGCACGACCCCGCCCAGCTGAC ACCGACGCTCCTACTTCCGTACAGCAGCTCAGGGT GGACAGGAACAGCTGGCACGAGGAGGACGCCTACACG TGTGTGGTGATGCACGAGGCCCTGCACAATCACTACAT GCAGAAGTCCACCTCTAAGTCTGCGGGTAAATGA (SEQ ID NO: 32) | AGK*<br>(SEQ ID NO: 24) | | |
| | IgG2 variant 3 | GCCTCCACCACAGCCCCACCGAAAGTCTACCCTCTGAGTTC TTGCTGCGGGACAAGTCCAGTCTGGGGGTGACCCTGG GCTGCCTGGTCTTCAGCTACATGCCCGAGCCGGTGACC GTGACCTGGAACTCGGGTGCCCTGAAGAGCGGCGTGCA CACCTTCCCGGCCGTCTCCTTCAGTCTCCTCGGGCTCTACT CTCTCAGCAGCAGCTTCACCTGACCGTGCCCCAGCAGCTCA GGAACCCCAGACCACCTTCACCTGGAACTAGCCCACCCGGC CAGCAGCAGCACCACAAGGTGTTGGGTCTCCA GTGACTGCTCCAAGCCTAATAACCAGCATTGCGTGAGG GAACCATCGTCTTCATCTTCCACCGAAACCCCAAAGA CACCCTGATGATCACAGGAAGCCCCGAGGTCACGTGTG TGGTGAACGTGGGCCACGATAACCCCGAGGTGCAG TTCTCCTGGTTCGTGGACGACGTGGAGGTGCACAACCGC CAGGACGAAGCCGAGAGAGGAGCAGTTCAACAGCACCGT ACCGCGTGGTCAGCGCCCTGCCCATCCAGCACCAGGAC TGGAGCTGGAAGAAAGGAGTTCAAGTGCAAGGTCAACAT CAAAGGCCTCTCGCCTCCATCGTGAGGATCATCTCCA GGAGCAAAGGGCCGGCCCGGGAGCCCAGTGTATGT CCTGGACCCACCCCAAGGAAGAGCTCAGCAAAGCACGG TCAGCCTCACCTGCATGGTCATCGGCTTCTACCCAGAA GATGTAGACGTGGAGTGGCAGAGGACCGCAGACTGA GTCGGAGGACAAGTACCGCACCACCCCGCCCAGCTG GACGCGACCGCTCCTACTTCCTGTACAGCAAGCTAC GGTGGACAAGAGCAGGTGGCAGAGGAGAACCACTAC ACGTGTGTGGTGATGCACGAGGCCCTGCACAATCACTA CATGCAGAAGTCCACCTCTAAGTCTGCGGGTAAATGA (SEQ ID NO: 34) | ASTTAPKVYPLSSCCGDKSSSGVTLGC<br>LVSSYPEPVTVTWNSGALKSGVHTFP<br>AVLQSSGLYSLSSMVTVPASSSGTQTF<br>TCNVHAPASSTKVDKAVGVSSDCSKP<br>NNQHCVREPSVFIFPPKPKDTLMITGTP<br>EVTCVVVNGHDNPEVQFSWFVDDVE<br>VHTARTKPREEQFNSTYRVVSALPIQH<br>QDWTGKEFKCKVNIKGLSASIVRIISRS<br>KGPAREPQVVVLDPPKEELSKSTVSLT<br>CMVIGFYPEDVDVEWQRDRQTESEDKY<br>RTTPPQLDADRSYFLYSKLRVDRNSWQ<br>RGDTYTCVVMHEALHNHYMQKSTSKS<br>AGK*<br>(SEQ ID NO: 26) | X16702<br>(M25279) | |
| | IgG3 variant 1 | GCTTCCACCACAGCCCCTACCCTCTGGCATC CAGCTGCGGACACATCCAGCTCCACCGTGACCCTGG GCTGCCTGGTCTTCAGCTACATGCCCGAGCCGGTGACC GTGACCTGGAACTCGGGTGCCCTGAAGAGCGGCGTGCA CACCTTCCCGGCCGTGTCCGTCAGTCTCTGGGCTGTACT CTCTCAGCAGCATGGTGACTGTGCCCCAGCAGCTCA GAAACCCCAGACCTTCACCTGCAACGTAGCCCACCCGGC | ASTTAPKVYPLASSCGDTSSSTVTLGC<br>LVSSYMPEPVTVTWNSGALKSGVHTFP<br>AVRQSSGLYSLSSMVTVPASSSETQTF<br>TCNVAHPASSTKVDKAVTARRPVPTTP<br>KTTIPPGKPTPKSEVEKTPCQCSKCP<br>EPLGGLSVFIFPPKPKDTLTISGTPEVT<br>CVVVDVGQDDPEVQFSWFVDDVEVHT | U63638 | |

| Species | Ig Domain | Nucleotide Sequence | Amino Acid Sequence | GenBank Accession No. | IMGT Database Reference |
|---|---|---|---|---|---|
| | | CAGCAGCACCAAGGTGGACAAGGCTGTCACTGCAAGGC GTCCAGTCCCCAGCACGCCAAAGACAACTATCCCTCCT GGAAAACCACACCCCAGTGTTCAAGTTGAAGACC ACCCTGCCAGTGTTCCAAATGCCCAGAACCTCTGGGAG GACTGTCTGTCTTCATCTTCCCACCGAAACCCAAGGAC ACCCTCACAATCTCGGAACGCCCGAGGTCAGTGTGT GGTGGTGGACGTGGGCCAGGATGACCCCGAGGTGCAG TTCTCCTGGTTCGTGGACGACGTGGAGGTGCACAGCACCT CAGGACGAAGCCGAGAGAGGAGCAGTTCAACAGCAACT ACCGCGTGGTCAGCGCCCTGCCCATCCAGCACCAGGA CTGGCTGCAGGGCAAAGAGTTCAAGTGCAAGGTCAACA ACAAAGCCCTCCCGGCCCCCATTGTGAGGACCATCTCC AGGACCAAAGGCAGGCCCACCCGGGAGCCGAGTGTATG TCCTGCCCCACCCCGGGAAGAGTCAGCAAAGCACG CTCAGCCTCACCTGCCTGATCACCGGTTTCTACCCAGA AGAGATAGACGTGGAGTGGCAGAGAAATGGGCAGCCT GAGTCGGAGGACAAGTACCACACGACCGCACCCCAGCTG GATGCTGACGGCTCCTACTTCGTGTACAGCAAGCTCAG GGTGAACAAGACAGCTGGCAGAGGAGAGACCACTACA CGTGTGCAGTGATGACGAAGCTTTACGAGTCTCCGGGTAAATGA (SEQ ID NO: 35) | ARTKPREEQFNSTYRVVSALRIQHQDW LQGKEFKCKVNNKGLPAPIVRTISRTKG QAREPQVYVLAPPREELSKSTSLLTCLI TGFYPEEIDVEWQRNGQPESEDKYHTT APQLDADGSYFLYSKLRVNKSSWQEG DHYTCAVMHEALRNHYKEKSISRSPGK* (SEQ ID NO: 27) | | |
| | IgG3 variant 2 | GCCTCCACCACGGCCCCGAAAGTCTACCCTCTGGCATC CCGTCGGGAGACACATCCAGTCCACCGTGACCCTGG GCTGCCTGGTCTCCAGCTACATGCCCGAGCCGGTGACC GTGACCTGGAACTCGGGCTGCCCTGACCTGGCAGTGCA CACCTTCCCGGCCGTCCTTCAGTCGACCGTGCCCTCCAGCAACGTCCC CTCTCAGCAGCATGGTACCGCTGCCCCCCACCGACCTCA GAAACCCAGACCCTTCACCTGCAACGTAGCCCACCCGGC CAGCAGCACCAAGGTGGACAAGGCTGTCACTGCAAGGC GTCCAGTCCCGACGACGCCAAAGACAACTATCCCTCCT GGAAAACCACACCCCAGTGTTCAAATGCCCAGAACCTCTGGGAG GACTGTCTGTCTTGATCTTCCGGGAACGCCCGAGGTCAGTGTGT GGTGGTGGACGTGGGCCAGGATGACCCCGAGGTGCAG TTCTCCTGGTTCGTGGACGACGTGGAGGTGCACAGCACCT CAGGACGAAGCCGAGAGAGGAGCAGTTCAACAGCAACT ACCGCGTGGTCAGCGCCCTGCCCATCCAGCACCAGGA CTGGCTGCAGGGCAAAGAGTTCAAGTGCAAGGTCAACA ACAAAGCCCTCCCGGCCCCCATTGTGAGGACCATCTCC AGGACCAAAGGCAGGCCCACCCGGGAGCCGAGTGTATG TCCTGCCCCACCCCGGGAAGAGTCAGCAAAGACG CTCAGCCTCACCTGCCTGATCACCGGTTTCTACCCAGA AGAGATAGACGTGGAGTGGCAGAGAAATGGGCAGCCT GAGTCGGAGGACAAGTACCACACGACCGCACCCCAGCTG GATGCTGACGGCTCCTACTTCGTGTACAGCAGGCTCAG GGTGAACAAGACAGCTGGCAGAGGAGAGACCACTACA CGTGTGCAGTGATGACGAAGCTTTACGAGTCACTAC | ASTTAPKVYPLASRCGDTSSSTVTLGC LVSSYMPEPVTVTWNSGALKSGVHTFP AVLQSSGLYSLSSMVTVPASTSETQTF TCNVAHPASSTKVDKAVTARRPVPTTP KTTIPPGKPTTQESEVEKTPCQCSKCP EPLGGLSVFIFPPKPKDTLTISGTPEVT CVVVDVGQDDPEVQFSWFVDDVEVHT ARTKPREEQFNSTYRVVSALRIQHQDW LQGKEFKCKVNNKGLPAPIVRTISRTKG QAREPQVYVLAPPPREELSKSTLSLTCLI TGFYPEEIDVEWQRNGQPESEDKYHTT APQLDADGSYFLYSKLRVNKSSWQEG DYYTCAVMHEALRNHYKEKSISRSPGK* (SEQ ID NO: 28) | U63639 | |

TABLE-continued

| Species | Ig Domain | Nucleotide Sequence | Amino Acid Sequence | GenBank Accession No. | IMGT Database | Reference |
|---|---|---|---|---|---|---|
| Bovine | Ig light chain constant region (CL) | Ig lambda CAGCCCAAGTCCCACCCTCCGTCACCCTGTTCCCGCC CTCCACGGAGAGCTCAACGGCAACAAGGCCACCCTG GTGTGTCTCATCAGCGACTTCTACCCGGGTAGCGTGAC CGTGGTCTGGAAGGCAGACGGCAGCACCATCACCCGCA ACGTGGAGACCACCCGGGCCTCAACAGAGCAACAG CAAGTACGCGGCCAGCAGCTACCTGAGCCTGACGAGCA GCGACTGGAAATCGAAAGGCAGTTACAGCTGCGAGTC ACGCACGAGGGGAGCACCGTGACGAAGACAGTGAAGC CCTCAGAGTGTTCTTAG (SEQ ID NO: 7) AAAGAGAAGTCCATCTCGAGGTCTCCGGGTAAATGA (SEQ ID NO: 36) | QPKSPPSVTLFPPSTEELNGNKATLVC LISDFYPGSVTVWKADGSTITRNVETT RASKQSNSKYAASSYLSLTSSDWKSKG SYSCEVTHEGSTVTKTVKPSECS* (SEQ ID NO: 3) | X62917 | Not registered | Chen L. et al., Vet. Immunol. Immuno-pathol. 124, 284-294 (2008). PMID: 18538861 |

TABLE

| Species | Ig Domain | | Nucleotide Sequence | Amino Acid Sequence | GenBank Accession No. | IMGT Database | Reference |
|---|---|---|---|---|---|---|---|
| Ovine (Scientific Name: *Ovis aries*) | Ovine Ig heavy chain constant region (CH1~CH3) | IgG1 | GCCTCAACAACACCCC CGAAAGTCTACCCTCT GACTTCTTGCTGCGGG GACACGTCCAGCTCCA TCGTGACCCTGGGCTG CCTGGTCTCCAGCTATA TGCCCGAGCCGGTGAC CGTGACCTGGAACTCT GGTGCCCTGACCAGCG GCGTGCACACCTTCCC GGCCATCCTGCAGTCC TCCGGGCTCTACTCTC TCAGCAGCGTGGTGAC CGTGCCGGCCAGCACC TCAGGAGCCCAGACCT TCATCTGCAACGTAGC CCACCCGGCCAGCAGC ACCAAGGTGGACAAG CGTGTTGAGCCCGGAT GCCCGGACCCATGCAA ACATTGCCGATGCCCA CCCCCTGAGCTCCCCG GAGGACCGTCTGTCTT CATCTTCCCACCGAAA CCCAAGGACACCCTTA CAATCTCTGGAACGCC CGAGGTCACGTGTGTG GTGGTGGACGTGGGCC AGGATGACCCCGAGGT GCAGTTCTCCTGGTTC GTGGACAACGTGGAG GTGCGCACGGCCAGG ACAAAGCCGAGAGAG GAGCAGTTCAACAGC ACCTTCCGCGTGGTCA GCGCCCTGCCCATCCA GCACCAAGACTGGACT GGAGGAAAGGAGTTC AAGTGCAAGGTCCAC AACGAAGCCCTCCCGG CCCCCATCGTGAGGAC CATCTCCAGGACCAAA GGGCAGGCCCGGGAG CCGCAGGTGTACGTCC TGGCCCCACCCCAGGA AGAGCTCAGCAAAAG CACGCTCAGCGTCACC TGCCTGGTCACCGGCT TCTACCCAGACTACAT CGCCGTGGAGTGGCA GAAAAATGGGCAGCCT GAGTCGGAGGACAAG TACGGCACGACCACAT CCCAGCTGGACGCCGA CGGCTCCTACTTCCTGT ACAGCAGGCTCAGGG TGGACAAGAACAGCT GGCAAGAAGGAGACA CCTACGCGTGTGTGGT GATGCACGAGGCTCTG CACAACCACTACACAC AGAAGTCGATCTCTAA GCCTCCGGGTAAATGA (SEQ ID NO: 38) | ASTTPPKVYPLTSCC GDTSSSIVTLGCLVSS YMPEPVTVTWNSGA LTSGVHTFPAILQSSG LYSLSSVVTVPASTSG AQTFICNVAHPASST KVDKRVEPGCPDPC KHCRCPPPELPGGPS VFIFPPKPKDTLTISGT PEVTCVVVDVGQDD PEVQFSWFVDNVEV RTARTKPREEQFNSTF RVVSALPIQHQDWT GGKEFKCKVHNEAL PAPIVRTISRTKGQAR EPQVYVLAPPQEELS KSTLSVTCLVTGFYP DYIAVEWQKNGQPE SEDKYGTTTSQLDAD GSYFLYSRLRVDKNS WQEGDTYACVVMH EALHNHYTQKSISKP PGK* (SEQ ID NO: 37) | X69797 | http:// www.imgt.org/ IMGTrepertoire/ index.php? section= LocusGenes& repertoire= genetable& species= sheep&group= IGHC | Dufour V. et al., J. Immunol., 156, 2163-2170 (1996). PMID: 8690905 |
| | | IgG2 | GCCTCCACCACAGCCC CGAAAGTCTACCCTCT GACTTCTTGCTGCGGG GACACGTCCAGCTCCA GCTCCATCGTGACCCT GGGCTGCCTGGTCTCC AGCTATATGCCCGAGC CGGTGACCGTGACCTG GAACTCTGGTGCCCTG ACCAGCGGCGTGCAC ACCTTCCCGGCCATCC TGCAGTCCTCCGGGCT | ASTTAPKVYPLTSCC GDTSSSSIVTLGCLV SSYMPEPVTVTWNS GALTSGVHTFPAILQS SGLYSLSSVVTVPAST SGAQTFICNVAHPASS AKVDKRVGISSDYSK CSKPPCVSRPSVFIFP PKPKDSLMITGTPEV TCVVVDVGQGDPEV QFSWFVDNVEVRTA RTKPREEQFNSTFRV | X70983 | | Clarkson C. A. et al., Mol. Immunol., 30, 1195-1204 (1993). PMID: 8413324 |

TABLE-continued

| Species | Ig Domain | Nucleotide Sequence | Amino Acid Sequence | GenBank Accession No. | IMGT Database | Reference |
|---|---|---|---|---|---|---|
| | | CTACTCTCTCAGCAGC GTGGTGACCGTGCCGG CCAGCACCTCAGGAGC CCAGACCTTCATCTGC AACGTAGCCCACCCGG CCAGCAGCGCCAAGG TGGACAAGCGTGTTGG GATCTCCAGTGACTAC TCCAAGTGTTCTAAAC CGCCTTGCGTGAGCCG ACCGTCTGTCTTCATCT TCCCCCCGAAACCCAA GGACAGCCTCATGATC ACAGGAACGCCCGAG GTCACGTGTGTGGTGG TGGACGTGGGCCAGG GTGACCCCGAGGTGCA GTTCTCCTGGTTCGTG GACAACGTGGAGGTG CGCACGGCCAGGACA AAGCCGAGAGGAGGAG CAGTTCAACAGCACCT TCCGCGTGGTCAGCGC CCTGCCCATCCAGCAC GACCACTGGACTGGA GGAAAGGAGTTCAAG TGCAAGGTCCACAGCA AAGGCCTCCCGGCCCC CATCGTGAGGACCATC TCCAGGGCCAAAGGG CAGGCCCGGGAGCCG CAGGTGTACGTCCTGG CCCCACCCCAGGAAG AGCTCAGCAAAAGCA CGCTCAGCGTCACCTG CCTGGTCACCGGCTTC TACCCAGACTACATCG CCGTGGAGTGGCAGA GAGCGCGGCAGCCTG AGTCGGAGGACAAGT ACGGCACGACCACATC CCAGCTGGACGCCGAC GGCTCCTACTTCCTGT ACAGCAGGCTCAGGG TGGACAAGAGCAGCT GGCAAAGAGGAGACA CCTACGCGTGTGTGGT GATGCACGAGGCTCTG CACAACCACTACACAC AGAAGTCGATCTCTAA GCCTCCGGGTAAATGA (SEQ ID NO: 40) | VSALPIQHDHWTGG KEFKCKVHSKGLPAP IVRTISRAKGQAREP QVYVLAPPQEELSKS TLSVTCLVTGFYPDYI AVEWQRARQPESED KYGTTTSQLDADGS YFLYSRLRVDKSSWQ RGDTYACVVMHEAL HNHYTQKSISKPPGK* (SEQ ID NO: 39) | | | |
| Ovine Ig light chain constant region | Ig kappa (CK) | CCATCCGTCTTCCTCTT CAAACCATCTGAGGAA CAGCTGAGGACCGGA ACTGTCTCTGTCGTGT GCTTGGTGAATGATTT CTACCCCAAAGATATC AATGTCAAGGTGAAAG TGGATGGGGTTACCCA GAACAGCAACTTCCAG AACAGCTTCACAGACC AGGACAGCAAGAAAA GCACCTACAGCCTCAG CAGCACCCTGACACTG TCCAGCTCAGAGTACC AGAGCCATAACGCCTA TGCGTGTGAGGTCAGC CACAAGAGCCTGCCCA CCGCCCTCGTCAAGAG CTTCAATAAGAATGAA TGTTAG (SEQ ID NO: 42) | PSVFLFKPSEEQLRTG TVSVVCLVNDFYPKD INVKVKVDGVTQNS NFQNSFTDQDSKKST YSLSSTLTLSSSEYQS HNAYACEVSHKSLPT ALVKSFNKNEC* (SEQ ID NO: 41) | X54110 | Not registered | Jenne C. N. et al., Dev. Comp. Immunol. 30(1-2), 165-174 (2006). PMID: 16083958 |
| | Ig lambda (CL) | GGTCAGCCCAAGTCCG CACCCCTCGGTCACCCT GTTCCCGCCCTTCCACG | GQPKSAPSVTLFPPST EELSTNKATVVCLIN DFYPGSVNVVWKAD | AY734681 | | |

TABLE-continued

| Species | Ig Domain | Nucleotide Sequence | Amino Acid Sequence | GenBank Accession No. | IMGT Database | Reference |
|---|---|---|---|---|---|---|
| | | GAGGAGCTCAGTACCA ACAAGGCCACCGTGGT GTGTCTCATCAACGAC TTCTACCCGGGTAGCG TGAACGTGGTCTGGAA GGCAGATGGCAGCACC ATCAATCAGAACGTGA AGACCACCCAGGCCTC CAAACAGAGCAACAG CAAGTACGCGGCCAGC AGCTACCTGACCCTGA CGGGCAGCGAGTGGA AGTCTAAGAGCAGTTA CACCTGCGAGGTCACG CACGAGGGGAGCACC GTGACGAAGACAGTG AAGCCCTCAGAGTGTT CTTAG (SEQ ID NO: 44) | GSTINQNVKTTQASK QSNSKYAASSYLTLT GSEWKSKSSYTCEVT HEGSTVTKTVKPSEC S* (SEQ ID NO: 43) | | | |

TABLE

| Species | Ig Domain | Nucleotide Sequence | Amino Acid Sequence | GenBank Accession No. | IMGT Database | Reference |
|---|---|---|---|---|---|---|
| Ovine (Scientific Name: Ovis aries) | Ovine Ig IgG1 heavy chain constant region (CH1~CH3) | GCCTCAACAACACCCC CGAAAGTCTACCCTCT GACTTCTTGCTGCGGG GACACGTCCAGCTCCA TCGTGACCCTGGGCTG CCTGGTCTCCAGCTATA TGCCCGAGCCGGTGAC CGTGACCTGGAACTCT GGTGCCTGACCAGCG GCGTGCACACCTTCCC GGCCATCCTGCAGTCC TCCGGGCTCTACTCTC TCAGCAGCGTGGTGAC CGTGCCGGCCAGCACC TCAGGAGCCCAGACCT TCATCTGCAACGTAGC CCACCCGGCCAGCAGC ACCAAGGTGGACAAG CGTGTTGAGCCCGGAT GCCCGGACCCATGCAA ACATTGCCGATGCCCA CCCCCTGAGCTCCCCG GAGGACCGTCTGTCTT CATCTTCCCACCGAAA CCCAAGGACACCCTTA CAATCTCTGGAACGCC CGAGGTCACGTGTGTG GTGGTGGACGTGGGCC AGGATGACCCCGAGGT GCAGTTCTCCTGGTTC GTGGACAACGTGGAG GTGCGCACGGCCAGG ACAAAGCCGAGAGAG GAGCAGTTCAACAGC ACCTTCCGCGTGGTCA GCGCCCTGCCCATCCA GCACCAAGACTGGACT GGAGGAAAGGAGTTC AAGTGCAAGGTCCAC AACGAAGCCCTCCCGG CCCCCATCGTGAGGAC CATCTCCAGGACCAAA GGGCAGGCCCGGGAG CCGCAGGTGTACGTCC TGGCCCCACCCCAGGA AGAGCTCAGCAAAAG CACGCTCAGCGTCACC | ASTTPPKVYPLTSCC GDTSSSIVTLGCLVSS YMPEPVTVTWNSGA LTSGVHTFPAILQSSG LYSLSSVVTVPASTSG AQTFICNVAHPASST KVDKRVEPGCPDPC KHCRCPPPELPGGPS VFIFPPKPKDTLTISGT PEVTCVVVDVGQDD PEVQFSWFVDNVEV RTARTKPREEQFNSTF RVVSALPIQHQDWT GGKEFKCKVHNEAL PAPIVRTISRTKGQAR EPQVYVLAPPQEELS KSTLSVTCLVTGFYP DYIAVEWQKNGQPE SEDKYGTTTSQLDAD GSYFLYSRLRVDKNS WQEGDTYACVVMH EALHNHYTQKSISKP PGK* (SEQ ID NO: 37) | X69797 | http:// www.imgt.org/ IMGTreper- toire/ index.php? section= LocusGenes& repertoire= genetable& species= sheep&group= IGHC | Dufour V. et al., J. Immunol., 156, 2163-2170 (1996). PMID: 8690905 |

| Species | Ig Domain | Nucleotide Sequence | Amino Acid Sequence | GenBank Accession No. | IMGT Database | Reference |
|---|---|---|---|---|---|---|
| | | TGCCTGGTCACCGGCT TCTACCCAGACTACAT CGCCGTGGAGTGGCA GAAAAATGGGCAGCCT GAGTCGGAGGACAAG TACGGCACGACCACAT CCCAGCTGGACGCCGA CGGCTCCTACTTCCTGT ACAGCAGGCTCAGGG TGGACAAGAACAGCT GGCAAGAAGGAGACA CCTACGCGTGTGTGGT GATGCACGAGGCTCTG CACAACCACTACACAC AGAAGTCGATCTCTAA GCCTCCGGGTAAATGA (SEQ ID NO: 38) | | | | |
| | IgG2 | GCCTCCACCACAGCCC CGAAAGTCTACCCTCT GACTTCTTGCTGCGGG GACACGTCCAGCTCCA GCTCCATCGTGACCCT GGGCTGCCTGGTCTCC AGCTATATGCCCGAGC CGGTGACCGTGACCTG GAACTCTGGTGCCCTG ACCAGCGGCGTGCAC ACCTTCCCGGCCATCC TGCAGTCCTCCGGGCT CTACTCTCTCAGCAGC GTGGTGACCGTGCCGG CCAGCACCTCAGGAGC CCAGACCTTCATCTGC AACGTAGCCCACCCGG CCAGCAGCGCCAAGG TGGACAAGCGTGTTGG GATCTCCAGTGACTAC TCCAAGTGTTCTAAAC CGCCTTGCGTGAGCCG ACCGTCTGTCTTCATCT TCCCCCCGAAACCCAA GGACAGCCTCATGATC ACAGGAACGCCCGAG GTCACGTGTGTGGTGG TGGACGTGGGCCAGG GTGACCCCGAGGTGCA GTTCTCCTGGTTCGTG GACAACGTGGAGGTG CGCACGGCCAGGACA AAGCCGAGAGAGGAG CAGTTCAACAGCACCT TCCGCGTGGTCAGCGC CCTGCCCATCCAGCAC GACCACTGGACTGGA GGAAAGGAGTTCAAG TGCAAGGTCCACAGCA AAGGCCTCCCGGCCCC CATCGTGAGGACCATC TCCAGGGCCAAAGGG CAGGCCCGGGAGCCG CAGGTGTACGTCCTGG CCCCACCCCAGGAAG AGCTCAGCAAAAGCA CGCTCAGCGTCACCTG CCTGGTCACCGGCTTC TACCCAGACTACATCG CCGTGGAGTGGCAGA GAGCGCGGCAGCCTG AGTCGGAGGACAAGT ACGGCACGACCACATC CCAGCTGGACGCCGAC GGCTCCTACTTCCTGT ACAGCAGGCTCAGGG TGGACAAGAGCAGCT GGCAAAGAGGAGACA CCTACGCGTGTGTGGT | ASTTAPKVYPLTSCC GDTSSSSSIVTLGCLV SSYMPEPVTVTWNS GALTSGVHTFPAILQS SGLYSLSSVVTVPAST SGAQTFICNVAHPASS AKVDKRVGISSDYSK CSKPPCVSRPSVFIFP PKPKDSLMITGTPEV TCVVVDVGQGDPEV QFSWFVDNVEVRTA RTKPREEQFNSTFRV VSALPIQHDHWTGG KEFKCKVHSKGLPAP IVRTISRAKGQAREP QVYVLAPPQEELSKS TLSVTCLVTGFYPDYI AVEWQRARQPESED KYGTTTSQLDADGS YFLYSRLRVDKSSWQ RGDTYACVVMHEAL HNHYTQKSISKPPGK* (SEQ ID NO: 39) | X70983 | | Clarkson C. A. et al., Mol. Immunol., 30, 1195-1204 (1993). PMID: 8413324 |

TABLE-continued

| Species | Ig Domain | Nucleotide Sequence | Amino Acid Sequence | GenBank Accession No. | IMGT Database | Reference |
|---|---|---|---|---|---|---|
| Ovine Ig light chain constant region | Ig kappa (CK) | GATGCACGAGGCTCTG CACAACCACTACACAC AGAAGTCGATCTCTAA GCCTCCGGGTAAATGA (SEQ ID NO: 40) CCATCCGTCTTCCTCTT CAAACCATCTGAGGAA CAGCTGAGGACCGGA ACTGTCTCTGTCGTGT GCTTGGTGAATGATTT CTACCCCAAAGATATC AATGTCAAGGTGAAAG TGGATGGGGTTACCCA GAACAGCAACTTCCAG AACAGCTTCACAGACC AGGACAGCAAGAAAA GCACCTACAGCCTCAG CAGCACCCTGACACTG TCCAGCTCAGAGTACC AGAGCCATAACGCCTA TGCGTGTGAGGTCAGC CACAAGAGCCTGCCCA CCGCCCTCGTCAAGAG CTTCAATAAGAATGAA TGTTAG (SEQ ID NO: 42) | PSVFLFKPSEEQLRTG TVSVVCLVNDFYPKD INVKVKVDGVTQNS NFQNSFTDQDSKKST YSLSSTLTLSSSEYQS HNAYACEVSHKSLPT ALVKSFNKNEC* (SEQ ID NO: 41) | X54110 | Not registered | Jenne C. N. et al., Dev. Comp. Immunol. 30 (1-2), 165-174 (2006). PMID: 16083958 |
| | Ig lambda (CL) | GGTCAGCCCAAGTCCG CACCCTCGGTCACCCT GTTCCCGCCTTCCACG GAGGAGCTCAGTACCA ACAAGGCCACCGTGGT GTGTCTCATCAACGAC TTCTACCCGGGTAGCG TGAACGTGGTCTGGAA GGCAGATGGCAGCACC ATCAATCAGAACGTGA AGACCACCCAGGCCTC CAAACAGAGCAACAG CAAGTACGCGGCCAGC AGCTACCTGACCCTGA CGGGCAGCGAGTGGA AGTCTAAGAGCAGTTA CACCTGCGAGGTCACG CACGAGGGAGCACC GTGACGAAGACAGTG AAGCCCTCAGAGTGTT CTTAG (SEQ ID NO: 44) | GQPKSAPSVTLFPPST EELSTNKATVVCLIN DFYPGSVNVVWKAD GSTINQNVKTTQASK QSNSKYAASSYLTLT GSEWKSKSSYTCEVT HEGSTVTKTVKPSEC S* (SEQ ID NO: 43) | AY734681 | | |

TABLE

| Species | Ig Domain | Nucleotide Sequence | Amino Acid Sequence | GenBank Accession No. | IMGT Database | Reference |
|---|---|---|---|---|---|---|
| Ovine (Scientific Name: Ovis aries) | Ovine Ig heavy chain constant region (CH1-CH3) IgG1 | GCCTCAACAACACCCC CGAAAGTCTACCCTCT GACTTCTTGCTGCGGG GACACGTCCAGCTCCA TCGTGACCCTGGGCTG CCTGGTCTCCAGCTATA TGCCCGAGCCGGTGAC CGTGACCTGGAACTCT GGTGTCCTGACCAGCG GCGTGCACACCTTCCC GGCCATCCTGCAGTCC TCCGGGCTCTACTCTC TCAGCAGCGTGGTGAC CGTGCCGGCCAGCACC CGTCAGGAGCCCAGACCT TCATCTGCAACGTAGC CCACCCGGCCAGCAGC ACCAAGGTGGACAAG | ASTTPPKVYPLTSCC GDTSSSIVTLGCLVSS YMPEPVTVTWNSGA LTSGVHTFPAILQSSG LYSLSSVVTVPASTG AQTFICNVAHPASST KVDKRVEPGCPDPC KHCRCPPPELPGGPS VFIFPPKPKDTLTISGT PEVTCVVVDVGQDD PEVQFSWFVDNVEV RTARTKPREEQFNSTF RVVSALPIQHQDWT GGKEFKCKVHNEAL PAPIVRTISRTKGQAR EPQVYVLAPPQEELS KSTLSVTCLVTGFYP DYIAVEWQKNGQPE | X69797 | http:// www.imgt.org/ IMGTreper- toire/ index.php? section= LocusGenes& repertoire= genetable& species= sheep&group= IGHC | Dufour V. et al., J. Immunol., 156, 2163-2170 (1996). PMID: 8690905 |

| Species | Ig Domain | Nucleotide Sequence | Amino Acid Sequence | GenBank Accession No. | IMGT Database | Reference |
|---|---|---|---|---|---|---|
| | | CGTGTTGAGCCCGGAT GCCCGGACCCATGCAA ACATTGCCGATGCCCA CCCCCTGAGCTCCCCG GAGGACCGTCTGTCTT CATCTTCCCACCGAAA CCCAGGACACCCTTA CAATCTCTGGAACGCC CGAGGTCACGTGTGTG GTGGTGGACGTGGGCC AGGATGACCCCGAGGT GCAGTTCTCCTGGTTC GTGGACAACGTGGAG GTGCGCACGGCCAGG ACAAAGCCGAGAGAG GAGCAGTTCAACAGC GAGCAGTTCAACAGC ACCTTCCGCGTGGTCA GCGCCCTGCCCATCCA GCACCAAGACTGGACT GGAGGAAAGGAGTTC AAGTGCAAGGTCCAC AACGAAGCCCTCCGG CCCCCATCGTGAGGAC CATCTCCAGGACCAAA GGGCAGGCCCGGGAG CCGCAGGTGTACGTCC TGGCCCCACCCCAGGA AGAGCTCAGCAAAAG CACGCTCAGCGTCACC TGCCTGGTCACCGGCT TCTACCCAGACTACAT CGCCGTGGAGTGGCA GAAAAATGGGCAGCCT GAGTCGGAGGACAAG TACGGCACGACCACAT CCCAGCTGGACGCCGA CGGCTCCTACTTCCTGT ACAGCAGGCTCAGGG TGGACAAGAACAGCT GGCAAGAAGGAGACA CCTACGCGTGTGTGGT GATGCACGAGGCTCTG CACAACCACTACACAC AGAAGTCGATCTCTAA GCCTCCGGGTAATGA (SEQ ID NO: 38) | SEDKYGTTTSQLDAD GSYFLYSRLRVDKNS WQEGDTYACVVMH EALHNHYTQKSISKP PGK* (SEQ ID NO: 37) | | | |
| | IgG2 | GCCTCCACCACAGCCC CGAAAGTCTACCCTCT GACTTCTTGCTGCGGG GACACGTCCAGCTCCA GCTCCATCGTGACCCT GGGCTGCCTGGTCTCC AGCTATATGCCCGAGC CGGTGACCGTGACCTG GAACTCTGGTGCCCTG ACCAGCGGCGTGCAC ACCTTCCCGGCCATCC TGCAGTCCTCCGGGCT CTACTCTCTCAGCAGC GTGGTGACCGTGCCGG CCAGCACCTCAGGAGC CCAGACCTTCATCTGC AACGTAGCCCACCCGG CCAGCAGCGCCAAGG TGGACAAGCGTGTTGG GATCTCCAGTGACTAC TCCAAGTGTTCTAAAC CGCCTTGCGTGAGCCG ACCGTCTGTCTTCATCT TCCCCCCGAAACCCAA GGACAGCCTCATGATC ACAGGAACGCCCGAG GTCACGTGTGTGGTGG TGGACGTGGGCCAGG GTGACCCCGAGGTGCA | ASTTAPKVYPLTSCC GDTSSSSIVTLGCLV SSYMPEPVTVTWNS GALTSGVHTFPAILQS SGLYSLSSVVTVPAST SGAQTFICNVAHPASS AKVDKRVGISSDYSK CSKPPCVSRPSVFIFP PKPKDSLMITGTPEV TCVVVDVGQGDPEV QFSWFVDNVEVRTA RTPREEQFNSTFRV VSALPIQHDHWTGG KEFKCKVHSKGLPAP IVRTISRAKGQAREP QVYVLAPPQEELSKS TLSVTCLVTGFYPDYI AVEWQRARQPESED KYGTTTSQLDADGS YFLYSRLRVDKSSWQ RGDTYACVVMHEAL HNHYTQKSISKPPGK* (SEQ ID NO: 39) | X70983 | | Clarkson C. A. et al., Mol. Immunol., 30, 1195-1204 (1993). PMID: 8413324 |

| Species | Ig Domain | Nucleotide Sequence | Amino Acid Sequence | GenBank Accession No. | IMGT Database | Reference |
|---|---|---|---|---|---|---|
| | | GTTCTCCTGTTCGTG GACAACGTGGAGGTG CGCACGGCCAGGACA AAGCCGAGAGAGGAG CAGTTCAACAGCACCT TCCGCGTGGTCAGCGC CCTGCCCATCCAGCAC GACCACTGGACTGGA GGAAAGGAGTTCAAG TGCAAGGTCCACAGCA AAGGCCTCCCGGCCCC CATCGTGAGGACCATC TCCAGGGCCAAAGGG CAGGCCCGGGAGCCG CAGGTGTACGTCCTGG CCCCACCCCAGGAAG AGCTCAGCAAAAGCA CGCTCAGCGTCACCTG CCTGGTCACCGGCTTC TACCCAGACTACATCG CCGTGGAGTGGCAGA GAGCGCGGCAGCCTG AGTCGGAGGACAAGT ACGGCACGACCACATC CCAGCTGGACGCCGAC GGCTCCTACTTCCTGT ACAGCAGGCTCAGGG TGGACAAGAGCAGCT GGCAAAGAGGAGACA CCTACGCGTGTGTGGT GATGCACGAGGCTCTG CACAACCACTACACAC AGAAGTCGATCTCTAA GCCTCCGGGTAAATGA (SEQ ID NO: 40) | | | | |
| Ovine Ig light chain constant region | Ig kappa (CK) | CCATCGTCTTCCTCTT CAAACCATCTGAGGAA CAGCTGAGGACCGGA ACTGTCTCTGTCGTGT GCTTGGTGAATGATTT CTACCCCAAAGATATC AATGTCAAGGTGAAAG TGGATGGGGTTACCCA GAACAGCAACTTCCAG AACAGCTTCACAGACC AGGACAGCAAGAAAA GCACCTACAGCCTCAG CAGCACCCTGACACTG TCCAGCTCAGAGTACC AGAGCCATAACGCCTA TGCGTGTGAGGTCAGC CACAAGAGCCTGCCCA CCGCCCTCGTCAAGAG CTTCAATAAGAATGAA TGTTAG (SEQ ID NO: 42) | PSVFLFKPSEEQLRTG TVSVVCLVNDFYPKD INVKVKVDGVTQNS NFQNSFTDQDSKKST YSLSSTLTLSSSEYQS HNAYACEVSHKSLPT ALVKSFNKNEC* (SEQ ID NO: 41) | X54110 | Not registered | Jenne C. N. et al., Immunol. 30 (1-2), 165-174 (2006). PMID: 16083958 |
| | Ig lambda (CL) | GGTCAGCCCAAGTCCG CACCCTCGGTCACCCT GTTCCCGCCTTCCACG GAGGAGCTCAGTACCA ACAAGGCCACCGTGGT GTGTCTCATCAACGAC TTCTACCCGGGTAGCG TGAACGTGGTCTGGAA GGCAGATGGCAGCACC ATCAATCAGAACGTGA AGACCACCCAGGCCTC CAAACAGAGCAACAG CAAGTACGCGGCCAGC AGCTACCTGACCCTGA CGGGCAGCGAGTGGA AGTCTAAGAGCAGTTA | GQPKSAPSVTLFPPST EELSTNKATVVCLIN DFYPGSVNVVWKAD GSTINQNVKTTQASK QSNSKYAASSYLTLT GSEWKSKSSYTCEVT HEGSTVTKTVKPSEC S* (SEQ ID NO: 43) | AY734681 | | |

TABLE-continued

| Species | Ig Domain | Nucleotide Sequence | Amino Acid Sequence | GenBank Accession No. | IMGT Database | Reference |
|---|---|---|---|---|---|---|
| | | CACCTGCGAGGTCACG CACGAGGGGAGCACC GTGACGAAGACAGTG AAGCCCTCAGAGTGTT CTTAG (SEQ ID NO: 44) | | | | |

TABLE

| Species | Ig Domain | | Nucleotide Sequence | Amino Acid Sequence | GenBank Accession No. | IMGT Database | Reference |
|---|---|---|---|---|---|---|---|
| Human (Scientific Name: Homo sapiens) | Human Ig heavy chain constant region (CH1-CH3) | IgG4 variant 1 | GAGTCCAAATATGGTC CCCCATGCCCATCATG CCCAGCACCTGAGTTC CTGGGGGGACCATCAG TCTTCCTGTTCCCCCC AAAACCCAAGGACAC TCTCATGATCTCCCGG ACCCCTGAGGTCACGT GCGTGGTGGTGGACGT GAGCCAGGAAGACCC CGAGGTCCAGTTCAAC TGGTACGTGGATGGCG TGGAGGTGCATAATGC CAAGACAAAGCCGCG GGAGGAGCAGTTCAA CAGCACGTACCGTGTG GTCAGCGTCCTCACCG TCCTGCACCAGGACTG GCTGAACGGCAAGGA GTACAAGTGCAAGGTC TCCAACAAAGGCCTCC CGTCCTCCATCGAGAA AACCATCTCCAAAGCC AAAGGGCAGCCCCGA GAGCCACAGGTGTACA CCCTGCCCCCATCCCA GGAGGAGATGACCAA GAACCAGGTCAGCCTG ACCTGCCTGGTCAAAG GCTTCTACCCCAGCGA CATCGCCGTGGAGTGG GAGAGCAATGGGCAG CCGGAGAACAACTACA AGACCACGCCTCCCGT GCTGGACTCCGACGGC TCCTTCTTCCTCTACAG CAGGCTAACCGTGGAC AAGAGCAGGTGGCAG GAGGGGAATGTCTTCT CATGCTCCGTGATGCA TGAGGCTCTGCACAAC CACTACACACAGAAGA GCCTCTCCCTGTCTCT GGGTAAATGA (SEQ ID NO: 54) | ESKYGPPCPSCPAPEF LGGPSVFLFPPKPKD TLMISRTPEVTCVVV DVSQEDPEVQFNWY VDGVEVHNAKTKPR EEQFNSTYRVVSVLT VLHQDWLNGKEYKC KVSNKGLPSSIEKTIS KAKGQPREPQVYTLP PSQEEMTKNQVSLTC LVKGFYPSDIAVEWE SNGQPENNYKTTPPV LDSDGSFFLYSRLTV DKSRWQEGNVFSCS VMHEALHNHYTQKS LSLSLGK* (SEQ ID NO: 53) | K01316 | http:// www.imgt.org/ IMGTreper- toire/ index.php? section= LocusGenes& repertoire= genetable& species= human&group= IGHC | Ellison J. et al., DNA, 1, 11-18 (1981). PMID: 6299662 |
| | | IgG4 variant 2 | GAGTCCAAATATGGTC CCCCGTGCCCATCATG CCCAGCACCTGAGTTC CTGGGGGGACCATCAG TCTTCCTGTTCCCCCC AAAACCCAAGGACAC TCTCATGATCTCCCGG ACCCCTGAGGTCACGT GCGTGGTGGTGGACGT GAGCCAGGAAGACCC CGAGGTCCAGTTCAAC TGGTACGTGGATGGCG TGGAGGTGCATAATGC CAAGACAAAGCCGCG | ESKYGPPCPSCPAPEF LGGPSVFLFPPKPKD TLMISRTPEVTCVVV DVSQEDPEVQFNWY VDGVEVHNAKTKPR EEQFNSTYRVVSVLT VVHQDWLNGKEYK CKVSNKGLPSSIEKTI SKAKGQPREPQVYTL PPSQEEMTKNQVSLT CLVKGFYPSDIAVEW ESNGQPENNYKTTPP VLDSDGSFFLYSRLT VDKSRWQEGNVFSC | AJ001563 | | Brusco A. et al., Eur. J. Immunogenet., 25, 349-355 (1998). PMID: 9805657 |

TABLE-continued

| Species | Ig Domain | Nucleotide Sequence | Amino Acid Sequence | GenBank Accession No. | IMGT Database | Reference |
|---------|-----------|---------------------|---------------------|-----------------------|---------------|-----------|
| | | GGAGGAGCAGTTCAA CAGCACGTACCGTGTG GTCAGCGTCCTCACCG TCGTGCACCAGGACTG GCTGAACGGCAAGGA GTACAAGTGCAAGGTC TCCAACAAAGGCCTCC CGTCCTCCATCGAGAA AACCATCTCCAAAGCC AAAGGGCAGCCCCGA GAGCCACAGGTGTACA CCCTGCCCCCATCCCA GGAGGAGATGACCAA GAACCAGGTCAGCCTG ACCTGCCTGGTCAAAG GCTTCTACCCCAGCGA CATCGCCGTGGAGTGG GAGAGCAATGGGCAG CCGGAGAACAACTACA AGACCACGCCTCCCGT GCTGGACTCCGACGGC TCCTTCTTCCTCTACAG CAGGCTAACCGTGGAC AAGAGCAGGTGGCAG GAGGGGAATGTCTTCT CATGCTCCGTGATGCA TGAGGCTCTGCACAAC CACTACACGCAGAAGA GCCTCTCCCTGTCTCT GGGTAAATGA (SEQ ID NO: 56) | SVMHEALHNHYTQK SLSLSLGK* (SEQ ID NO: 55) | | | |
| | IgG4 variant 3 | GCACCTGAGTTCCTGG GGGGACCATCAGTCTT CCTGTTCCCCCCAAAA CCCAAGGACACTCTCA TGATCTCCCGGACCCC TGAGGTCACGTGCGTG GTGGTGGACGTGAGCC AGGAAGACCCCGAGG TCCAGTTCAACTGGTA CGTGGATGGCGTGGAG GTGCATAATGCCAAGA CAAAGCCGCGGGAGG AGCAGTTCAACAGCAC GTACCGTGTGGTCAGC GTCCTCACCGTCCTGC ACCAGGACTGGCTGA ACGGCAAGGAGTACA AGTGCAAGGTCTCCAA CAAAGGCCTCCCGTCC TCCATCGAGAAAACCA TCTCCAAAGCCAAAGG GCAGCCCCGAGAGCC ACAGGTGTACACCCTG CCCCCATCCCAGGAGG AGATGACCAAGAACC AGGTCAGCCTGACCTG CCTGGTCAAAGGCTTC TACCCCAGCGACATCG CCGTGGAGTGGGAGA GCAATGGGCAGCCGG AGAACAACTACAAGA CCACGCCTCCCGTGCT GGACTCCGACGGCTCC TTCTTCCTCTACAGCA AGCTCACCGTGGACAA GAGCAGGTGGCAGGA GGGGAACGTCTTCTCA TGCTCCGTGATGCATG AGGCTCTGCACAACCA CTACACGCAGAAGAGC CTCTCCCTGTCTCTGG GTAAATGA (SEQ ID NO: 58) | APEFLGGPSVFLFPPK PKDTLMISRTPEVTC VVVDVSQEDPEVQF NWYVDGVEVHNAK TKPREEQFNSTYRVV SVLTVLHQDWLNGK EYKCKVSNKGLPSSI EKTISKAKGQPREPQ VYTLPPSQEEMTKNQ VSLTCLVKGFYPSDIA VEWESNGQPENNYK TTPPVLDSDGSFFLYS KLTVDKSRWQEGNV FSCSVMHEALHNHY TQKSLSLSLGK* (SEQ ID NO: 57) | AJ001564 | | |

TABLE-continued

| Species | Ig Domain | Nucleotide Sequence | Amino Acid Sequence | GenBank Accession No. | IMGT Database | Reference |
|---------|-----------|---------------------|---------------------|----------------------|---------------|-----------|
| Human Ig light chain constant region | Ig kappa (CK) | ACTGTGGCTGCACCAT CTGTCTTCATCTTCCCG CCATCTGATGAGCAGT TGAAATCTGGAACTGC CTCTGTTGTGTGCCTG CTGAATAACTTCTATCC CAGAGAGGCCAAAGT ACAGTGGAAGGTGGAT AACGCCCTCCAATCGG GTAACTCCCAGGAGAG TGTCACAGAGCAGGA CAGCAAGGACAGCAC CTACAGCCTCAGCAGC ACCCTGACGCTGAGCA AAGCAGACTACGAGA AACACAAAGTCTACGC CTGCGAAGTCACCCAT CAGGGCCTGAGCTCGC CCGTCACAAAGAGCTT CAACAGGGGAGAGTG TTAG (SEQ ID NO: 60) | TVAAPSVFIFPPSDEQ LKSGTASVVCLLNNF YPREAKVQWKVDN ALQSGNSQESVTEQD SKDSTYSLSSTLTLSK ADYEKHKVYACEVT HQGLSSPVTKSFNRG EC* (SEQ ID NO: 59) | X96754 | http://www.imgt.org/IMGTrepertoire/index.php?section=LocusGenes&repertoire=genetable&species=human&group=IGKC | None |

The amino acid sequences as shown in SEQ ID NOS: 3, 21-28, 37, 39, 41, 43, 45, 47, 49, 51, 53, 55, 57 and 59 may have deletion(s), substitution(s) or addition(s) of one or several (e.g., up to five, about 10 at the most) amino acids. Even when such mutations have been introduced, the resulting amino acid sequences are capable of having the function as the constant region of Ig heavy chain or light chain.

Although the constant region of wild-type human IgG1 has ADCC activity and CDC activity, it is known that these activities can be reduced by introducing amino acid substitutions and deletions into specific sites. In the case of animals other than human where the constant region of an immunoglobulin equivalent to human IgG4 has not been identified, mutations may be introduced into the relevant region of an immunoglobulin equivalent to human IgG1 so that the resultant constant region with reduced ADCC activity and CDC activity can be used.

The present invention provides an artificial genetic DNA comprising (a') a DNA encoding a light chain comprising a light chain variable region (VL) containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region (CL) of an antibody of an animal other than rat: and (b') a DNA encoding a heavy chain comprising a heavy chain variable region (VH) containing CDR1 having the amino acid sequence of GFDFDTYP (SEQ ID NO: 18). CDR2 having the amino acid sequence of ITIKTHNYAT (SEQ ID NO: 19) and CDR3 having the amino acid sequence of NREDFDY (SEQ ID NO: 20) and the heavy chain constant region (CH) of an antibody of an animal other than rat. The present invention also provides a DNA encoding a light chain comprising a VL containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the CL of an antibody of an animal other than rat. Further, the present invention also provides a DNA encoding a heavy chain comprising a VH containing CDR1 having the amino acid sequence of GFDFDTYP (SEQ ID NO: 18), CDR2 having the amino acid sequence of ITIKTHNYAT (SEQ ID NO: 19) and CDR3 having the amino acid sequence of NREDFDY (SEQ ID NO: 20) and the CH of an antibody of an animal other than rat.

For (a) a light chain comprising a light chain variable region containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region of an antibody of an animal other than rat; and (b) a heavy chain comprising a heavy chain variable region containing CDR1 having the amino acid sequence of GFDFDTYP (SEQ ID NO: 18), CDR2 having the amino acid sequence of ITIKTHNYAT (SEQ ID NO: 19) and CDR3 having the amino acid sequence of NREDFDY (SEQ ID NO: 20) and the heavy chain constant region of an antibody of an animal other than rat, reference should be had to the foregoing description. The DNA of (a') is a DNA (gene) encoding the light chain of (a); and the DNA of (b') is a DNA (gene) encoding the heavy chain of (b). An artificial genetic DNA comprising the DNA of (a') and the DNA of ('b) may be synthesized on commercial synthesizer. Restriction enzyme recognition sites. KOZAK sequences, poly-A addition signal sequences, promoter sequences, intron sequences or the like may be added to the artificial genetic DNA.

The present invention also provides a vector comprising the above-mentioned artificial genetic DNA.

As the vector, *Escherichia coli*-derived plasmids (e.g., pBR322, pBR325, pUC12 or pUC13); *Bacillus subtilis*-derived plasmids (e.g., pUB110, pTP5 or pC194), yeast-derived plasmids (e.g., pSH19 or pSH15); bacteriophages such as λ phage; animal viruses such as retrovirus or vaccinia virus, or insect pathogen viruses such as baculovirus may be used. In the Examples described later. pDC6 (Japanese Patent No. 5704753, U.S. Pat. No. 9,096,878, EU Patent 2385115, Hong Kong (China) patent HK1163739 and Australia Patent 2009331326) was used.

The vector may also comprise promoters, enhancers, splicing signals, poly-A addition signals, intron sequences, selection markers, SV40 replication origins, and so forth.

The present invention also provides a host cell transformed by the above vector. It is possible to prepare the anti-LAG-3 antibody of the invention by culturing the host cell and collecting the antibody of interest from the resultant culture. Therefore, the present invention also provides a method of preparing an antibody, comprising culturing the above-described host cell and collecting the anti-LAG-3 antibody of the invention from the culture. In the method of the present invention for preparing an antibody, a vector incorporating an artificial genetic DNA comprising a DNA encoding the light chain and a DNA encoding the heavy chain may be transfected into a host cell. Alternatively, a vector incorporating a DNA encoding the light chain and a vector incorporating a DNA encoding the heavy chain may be co-transfected into a host cell.

Examples of the host cell include, but are not limited to, bacterial cells (such as Escherichia bacteria. Bacillus bacteria or Bacillus subtilis), fungal cells (such as yeast or Aspergillus), insect cells (such as S2 cells or Sf cells), animal cells (such as CHO cells, COS cells, HeLa cells. C127 cells, 3T3 cells, BHK cells or HEK 293 cells) and plant cells. Among these. CHO-DG44 cell (CHO-DG44 (dfhr$^{-/-}$)) which is a dihydrofolate reductase deficient cell is preferable.

Introduction of a recombinant vector into a host cell may be performed by the methods disclosed in Molecular Cloning 2nd Edition, J. Sambrook et al., Cold Spring Harbor Lab. Press, 1989 (e.g., the calcium phosphate method, the DEAE-dextran method, transfection, microinjection, lipofection, electroporation, transduction, scrape loading, the shotgun method, etc.) or by infection.

The resultant transformant may be cultured in a medium, followed by collection of the anti-LAG-3 antibody of the present invention from the culture. When the antibody is secreted into the medium, the medium may be recovered, followed by isolation and purification of the antibody from the medium. When the antibody is produced within the transformed cells, the cells may be lysed, followed by isolation and purification of the antibody from the cell lysate.

Examples of the medium include, but are not limited to. OptiCHO medium. Dynamis medium, CD CHO medium, ActiCHO medium, FortiCHO medium, Ex-Cell CD CHO medium, BalanCD CHO medium, ProCHO 5 medium and Cellvento CHO-100 medium.

The pH of the medium varies depending on the cell to be cultured. Generally, a pH range from 6.8 to 7.6 is used; mostly, a pH range from 7.0 to 7.4 is appropriate.

When the cell to be cultured is CHO cells, culture may be performed by methods known to those skilled in the art. For example, it is usually possible to perform culturing in a gas-phase atmosphere having a $CO_2$ concentration of 0-40%, preferably 2-10%, at 30-39° C., preferably around 37° C.

The appropriate period of culture is usually from one day to three months, preferably from one day to three weeks.

Isolation and purification of the antibody may be performed by known methods. Known isolation/purification methods which may be used in the present invention include, but are not limited to, methods using difference in solubility (such as salting-out or solvent precipitation); methods using difference in molecular weight (such as dialysis, ultrafiltration, gel filtration or SDS-polyacrylamide gel electrophoresis); methods using difference in electric charge (such as ion exchange chromatography); methods using specific affinity (such as affinity chromatography); methods using difference in hydrophobicity (such as reversed phase high performance liquid chromatography); and methods using difference in isoelectric point (such as isoelectric focusing).

The anti-LAG-3 antibody of the present invention may be used as an antibody drug for animals or human. Therefore, the present invention provides a pharmaceutical composition comprising the above-described anti-LAG-3 antibody as an active ingredient.

The pharmaceutical composition of the present invention may be used for prevention and/or treatment of cancers and/or infections. Examples of cancers and/or infections include, but are not limited to, neoplastic diseases (e.g., malignant melanoma, lung cancer, gastric cancer, renal cancer, breast cancer, bladder cancer, esophageal cancer, ovarian cancer and the like), leukemia, Johne's disease, anaplasmosis, bacterial mastitis, mycotic mastitis, mycoplasma infections (such as mycoplasma mastitis, mycoplasma pneumonia or the like), tuberculosis, Theileria orientalis infection, cryptosporidiosis, coccidiosis, trypanosomiasis and leishmaniasis.

The anti-LAG-3 antibody of the present invention may be dissolved in buffers such as PBS, physiological saline or sterile water, optionally filter-sterilized with a filter or the like, and then administered to animal subjects (including human) by injection. To the solution of this antibody, additives (such as coloring agents, emulsifiers, suspending agents, surfactants, solubilizers, stabilizers, preservatives, antioxidants, buffers, isotonizing agents, pH adjusters and the like) may be added. As routes of administration, intravenous, intramuscular, intraperitoneal, subcutaneous or intradermal administration and the like may be selected. Transnasal or oral administration may also be used.

The dose and the number of times and frequency of administration of the anti-LAG-3 antibody of the present invention may vary depending on the symptoms, age and body weight of the animal subject, the method of administration, the dosage form and so on. For example, 0.1-100 mg/kg body weight, preferably 1-10 mg/kg body weight, per adult animal may usually be administered at least once at such a frequency that enables confirmation of the desired effect.

While the pharmaceutical composition of the present invention may be used alone, it may be used in combination with surgical operations, radiation therapies, other immunotherapies such as cancer vaccine, or molecular target drugs. Synergistic effect can be expected from such combinations.

EXAMPLES

Hereinbelow, the present invention will be described in more detail with reference to the following Examples. However, the present invention is not limited to these Examples.

[Example 1] Establishment of Rat-Bovine Chimeric Anti-Bovine LAG-3 Antibody

1. Introduction

Lymphocyte activation gene 3 (LAG-3), an immunoinhibitory receptor, was identified as a molecule closely related to CD4. Recently, it has been elucidated that LAG-3 is involved in immunosuppression in chronic infections and tumors. In the subject Example, for the purpose of establishing a novel therapy for bovine infections, the present inventors have prepared a chimeric antibody gene by linking the variable region genes of rat anti-bovine LAG-3 monoclonal antibody 2D8 capable of inhibiting the binding of bovine LAG-3 and MHC class II to the constant region genes of bovine immunoglobulins (bovine IgG1 and Igλ; however, mutations have been introduced into the putative binding sites for Fcγ receptors in CH2 domain of bovine IgG1 to inhibit ADCC activity; see FIG. 1 for amino acid numbers and mutations: 247 E→P, 248 L→V, 249 P→A, 250 G→deletion, 344 A→S, 345 P→S; Ikebuchi R, Konnai S, Okagawa T, Yokoyama K, Nakajima C, Suzuki Y. Murata S, Ohashi K. Immunology, 142(4):551-561; August 2014). This chimeric antibody gene was introduced into Chinese hamster ovary cells (CHO cells). By culturing/proliferating the resultant cells, the present inventors have obtained a rat-bovine chimeric anti-bovine LAG-3 antibody ch2D8 and confirmed its binding inhibitory activity and biological activities.

2. Materials, Methods and Experimental Results 2.1. Construction of Bovine LAG-3 Expressing Cells The nucleotide sequence of the full length cDNA molecule of bovine LAG-3 gene (GenBank accession number AB608099; Shirai T, Konnai S, Ikebuchi R, Okagawa T, Sunden Y, Onuma M, Murata S. Ohashi K. Vet. Immunol. Immunopathol, 144(3-4):462-467, Dec. 15, 2011) was determined. Based on the resultant genetic information, bovine LAG-3 expressing cells were prepared. First, for preparing a bovine LAG-3 expressing plasmid, PCR was performed using a synthesized bovine peripheral blood mononuclear cell (PBMC)-derived cDNA as a template and designed primers having BglII and EcoRI recognition sites on the 5' side (boLAG-3-EGFP F and R). The PCR products were digested with BglII (Takara) and EcoRI (Takara), purified with FastGene Gel/PCR Extraction Kit (NIPPON Genetics) and cloned into pEGFP-N2 vector (Clontech) treated with restriction enzymes in the same manner. The resultant expression plasmid of interest was extracted with QIAGEN Plasmid Midi kit (Qiagen) and stored at −30° C. until use in experiments. Hereinafter, the thus prepared expression plasmid is designated as pEGFP-N2-boLAG-3.

```
Primer (boLAG-3-EGFP F):
                                    (SEQ ID NO: 61)
GAAAGATCTATGCTGTGGGAGGCTTGGTT Primer (boLAG-3-EGFP R):
                                    (SEQ ID NO: 62)
CCGGAATTCGGGTTGCTCTGGCTGCAGCT
```

Bovine LAG-3 expressing cells were prepared by the procedures described below. First, COS-7 cells at a density of $5\times10^4$ cells/$cm^2$ were subcultured in 6-well plates, and then cultured overnight in RPMI 1640 medium (Sigma-Aldrich) containing 10% inactivated fetal bovine serum (Cell Culture Technologies), penicillin 200 U/ml, streptomycin 200 μg/ml and 0.01% L-glutamine (Life Technologies) at 37° C. in the presence of 5% $CO_2$. Subsequently, the pEGFP-N2-boLAG-3 or pEGFP-N2 (negative control) was introduced into COS-7 cells at 0.4 μg/$cm^2$ using Lipofectamine 2000 (Invitrogen). The cells were cultured for 48 hours (bovine LAG-3-EGFP expressing cells). In order to confirm the expression of bovine LAG-3 in the thus prepared expressing cells, intracellular localization of EGFP was visualized with an inverted confocal laser microscope LSM700 (ZEISS).

2.2. Construction of Soluble Bovine LAG-3

Bovine LAG-3-Ig expressing plasmid was constructed by the procedures described below. In order to amplify the signal peptide and the extracellular region of bovine LAG-3 (GenBank accession number AB608099), primers were designed that had NheI and NsiI recognition sites added on the 5' side (boLAG-3-Ig F and R). PCR was performed using a synthesized bovine PBMC-derived cDNA as a template. The PCR products were digested with NheI (Takara) and NsiI (Takara), purified with FastGene Gel/PCR Extraction Kit (NIPPON Genetics) and cloned into pCXN2.1-Rabbit IgG1 Fc vector (Niwa H, Yamamura K, Miyazaki J. Gene, 108(2):193-199; Dec. 15, 1991; kindly provided by Dr. T Yokomizo, Juntendo University Graduate School of Medicine, and modified in the inventors' laboratory) treated with restriction enzymes in the same manner. The expression plasmid was purified with FastGene Xpress Plasmid PLUS Kit (NIPPON Genetics) and stored at −30° C. until use in experiments. Hereinafter, the thus prepared expression plasmid is designated as pCXN2.1-boLAG-3-Ig.

```
Primer (boLAG-3-EGFP F):
                                    (SEQ ID NO: 63)
CTAGCTAGCCGCCCACCATGCTGTGGGAGGCTTGGTT Primer (boLAG-3-EGFP R):
                                    (SEQ ID NO: 64)
TGCATGCATCAGAACAGCTAGGTTGTACG
```

Soluble bovine LAG-3-Ig expressing cells were prepared by the procedures described below. Briefly, 30 μg of pCXN2.1-boLAG-3-Ig was introduced into $7.5\times10^7$ Expi293F cells (Life Technologies) using Expifectamine (Life Technologies). After 7-day culture under shaking, the culture supernatant was collected. The recombinant protein was purified from the supernatant using Ab-Capcher Extra (ProteNova). After purification, the buffer was exchanged with PBS (pH 7.4) using PD MiniTrap G-25 (GE Healthcare). The resultant protein was stored at −30° C. until use in experiments (bovine LAG-3-Ig). The concentration of the purified bovine LAG-3-Ig was measured using Rabbit IgG ELISA Quantitation Set (Bethyl). For each washing operation in ELISA, Auto Plate Washer BIO WASHER 50 (DS Pharma Biomedical) was used. Absorbance was measured with Microplate Reader MTP-650FA (Corona Electric).

2.3. Preparation of Rat Anti-Bovine LAG-3 Monoclonal Antibody Producing Cells

A peptide chain was synthesized from a part of the extracellular region of bovine LAG-3 (amino acid numbers 71 to 99; amino acid sequence: GSAAPTPRGPGPRRYTVLRLAPGGLRIGK (SEQ ID NO: 72)) by adding a cysteine residue to the $NH_2$ terminus, and was linked to keyhole limpet hemocyanin (a carrier protein). An emulsion of this peptide chain and TiterMax Gold Adjuvant (Sigma-Aldrich) was prepared. Rat was immunized in the footpad with the resulting emulsion. Subsequently, hybridomas were established by the iliac lymph node method to thereby obtain rat anti-bovine LAG-3 monoclonal antibody producing hybridoma 2D8. With respect to the method of establishment of rat anti-bovine LAG-3 monoclonal antibody, details are disclosed in the following non-patent document (Okagawa T, Konnai S, Nishimori A. Ikebuchi R. Mizorogi S, Nagata R, Kawaji S. Tanaka S, Kagawa Y, Murata S, Mori Y. Ohashi K. Infect. Immun., 84(1):77-89; Oct. 19, 2015).

2.4. Preparation of Rat-Bovine Chimeric Anti-Bovine LAG-3 Antibody Expressing Vector Rat-bovine chimeric anti-bovine LAG-3 antibody ch2D8 was established by fusing the antibody constant regions of bovine IgG1 and Igλ with rat anti-bovine LAG-3 antibody 2D8 being used as an antibody variable region.

First, the genes of heavy chain and light chain variable regions were identified by RACE from a hybridoma that would produce rat anti-bovine LAG-3 antibody 2D8. Subsequently, a gene sequence was prepared in which the heavy chain and the light chain variable regions of rat anti-bovine LAG-3 antibody 2D8 were linked to known constant regions of bovine IgG1 (heavy chain; modified from GenBank Accession number X62916) and bovine Ig. (light chain; GenBank Accession number X62917), respectively, and codon optimization was carried out [SEQ ID NOS: 9 and 10 (amino acid sequences). SEQ ID NOS: 14 and 15 (nucleotide sequences after codon optimization)]. It should be noted that in order to suppress the ADCC activity of bovine IgG1, mutations were added to the putative binding sites of Fcγ receptors in CH2 domain (See FIG. 1 for amino acid numbers and mutations: 247 E→P, 248 L→V, 249 P→A, 250 G→deletion, 344 A→S, 345 P→S; Ikebuchi R, Konnai S. Okagawa T. Yokoyama K, Nakajima C. Suzuki Y, Murata S, Ohashi K. Immunology, 142(4):551-561; August 2014). Then, the gene was artificially synthesized in such a manner that NotI recognition sequence, KOZAK sequence, chimeric antibody light chain sequence, poly-A addition signal sequence (PABGH), promoter sequence (PCMV), SacI recognition sequence, intron sequence (INRBG), KOZAK sequence, chimeric antibody heavy chain sequence and XbaI recognition sequence would be located in this order. The synthesized gene strand was digested with NotI (Takara) and XbaI (Takara), purified with FastGene Gel/PCR Extraction Kit (NIPPON Genetics) and cloned into the cloning site (NoII and XbaI restriction enzyme recognition sequences downstream of PCMV and between INRBG and PABGH) of expression plasmid pDC6 (kindly provided by Prof. S. Suzuki, Hokkaido University Research Center for Zoonosis Control) treated with restriction enzymes in the same manner (FIG. 2). The resultant plasmid was extracted with QIAGEN Plasmid Midi kit (Qiagen) and stored at −30° C. until use in experiments. Hereinafter, the thus prepared expression plasmid is designated as pDC6-boLAG-3ch2D8.

2.5. Expression of Rat-Bovine Chimeric Anti-Bovine LAG-3 Antibody

The pDC6-boLAG-3ch2D8 prepared above was transfected into CHO-DG44 cells (CHO-DG44 (dfhr$^{-/-}$)) which are a dihydrofolate reductase deficient cell. Forty-eight hours later, the medium was exchanged with CD OptiCHO medium (Life Technologies) containing 20 mM GlutaMAX supplement (Life Technologies). After cultured for 3 weeks, the cells were subjected to selection and cloning by limiting dilution. Subsequently, the concentrations of the chimeric antibody in the culture supernatants were measured by dot blotting and ELISA using anti-bovine IgG F(c) rabbit polyclonal antibody (Rockland) to thereby select high expression clones. The thus established cell clone stably expressing rat-bovine chimeric anti-bovine LAG-3 antibody was transferred into CD OptiCHO medium and cultured under shaking for 14 days (125 rpm, 37° C., 5% $CO_2$). Chimeric antibody production in the culture supernatant was measured by ELISA using anti-bovine IgG F(c) rabbit polyclonal antibody (Rockland). For each washing operation in ELISA, Auto Plate Washer BIO WASHER 50 (DS Pharma Biomedical) was used. Absorbance was measured with Microplate Reader MTP-650FA (Corona Electric). The culture supernatant at day 14 was centrifuged at 10,000 g for 10 min to remove cells, and the centrifugal supernatant was passed through a Steritop-GP 0.22 μm filter (Millipore) for sterilization and then stored at 4° C. until it was subjected to purification.

2.6. Purification of Rat-Bovine Chimeric Anti-Bovine LAG-3 Antibody

From the culture supernatant prepared as described above, each chimeric antibody was purified using Ab Capcher Extra (ProteNova). An open column method was used for binding to resin; PBS pH 7.4 was used as an equilibration buffer and a wash buffer. As an elution buffer, 0.1 M Glycine-HCl (pH 2.8) was used. As a neutralization buffer, 1M Tris (pH 9.0) was used. The purified antibody was subjected to buffer exchange with PBS (pH 7.4) using PD-10 Desalting Column (GE Healthcare) and concentrated using Amicon Ultra-15 (50 kDa, Millipore). The thus purified chimeric antibody was passed through a 0.22 μm syringe filter (Millipore) for sterilization and stored at 4° C. until use in experiments.

2.7. Confirmation of the Purity of Purified Rat-Bovine Chimeric Anti-Bovine LAG-3 Antibody (FIG. 3)

In order to confirm the purity of purified rat-bovine chimeric anti-bovine LAG-3 antibody, antibody proteins were detected by SDS-PAGE and CBB staining. The purified rat-bovine chimeric anti-bovine LAG-3 antibody ch2D8 was suspended in Laemmli Sample Buffer (Bio-Rad) and denatured at 95° C. for 5 min under reducing conditions (reduced with 2-mercaptoethaanol; Sigma-Aldrich) or under non-reducing conditions. Using 10% acrylamide gel, the prepared samples were electrophoresed. As a molecular weight marker, Precision Plus Protein All Blue Standards (Bio-Rad) was used. After electrophoresis, the gels were stained with Quick-CBB (Wako) and decolored in distilled water.

Figure 3:
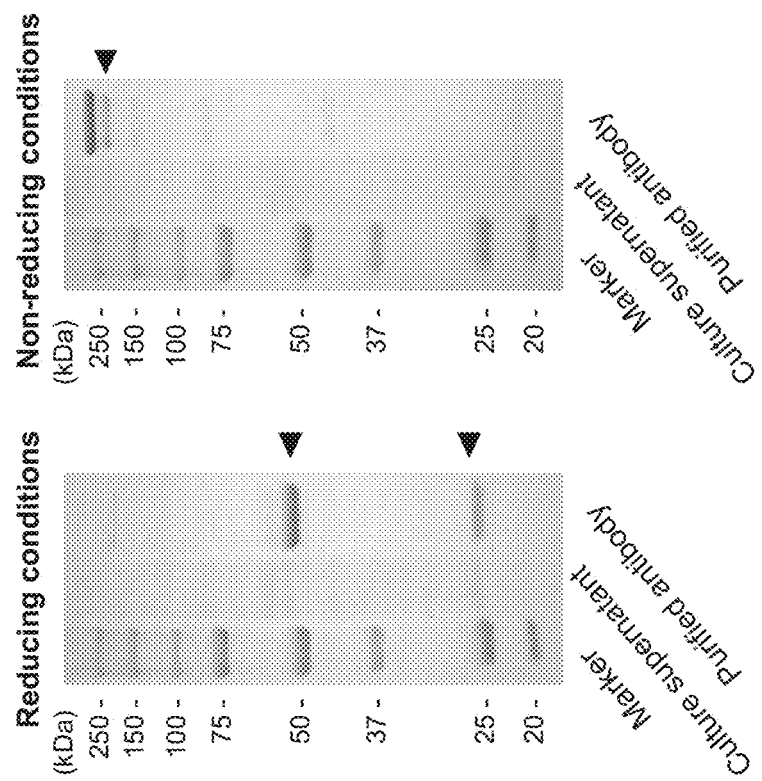
FIG. 3 The purity of purified rat-bovine chimeric anti-bovine LAG-3 antibody ch2D8.

The results are shown in FIG. 3. Bands of rat-bovine chimeric anti-bovine LAG-3 antibody were observed at predicted positions, that is, at 25 kDa (light chain) and 50 kDa (heavy chain) under reducing conditions and at 150-250 kDa under non-reducing conditions.

2.8. Binding Specificity of Rat-Bovine Chimeric Anti-Bovine LAG-3 Antibody (FIG. 4)

It was confirmed by flow cytometry that the rat-bovine chimeric anti-bovine LAG-3 antibody specifically binds to the bovine LAG-3 expressing cells (described above). First, rat anti-bovine LAG-3 antibody 2D8 or rat-bovine chimeric anti-bovine LAG-3 antibody ch2D8 was reacted with bovine LAG-3 expressing cells at room temperature for 30 min. After washing, Allophycocyanine (APC)-labeled anti-rat Ig goat antibody (Southern Biotech) or Alexa Fluor 647-labeled anti-bovine IgG (H+L) goat F(ab')2 (Jackson ImmunoResearch) was reacted at room temperature for 30 min. As negative control antibody, rat IgG2a (K) isotype control (BD Biosciences) or bovine IgG1 antibody (Bethyl) was used. After washing, each rat antibody or rat-bovine chimeric antibody bound to cell surfaces was detected by FACS Verse (BD Biosciences). For every washing operation and dilution of antibodies, PBS supplemented with 1% bovine serum albumin (Sigma-Aldrich) was used.

Figure 4:
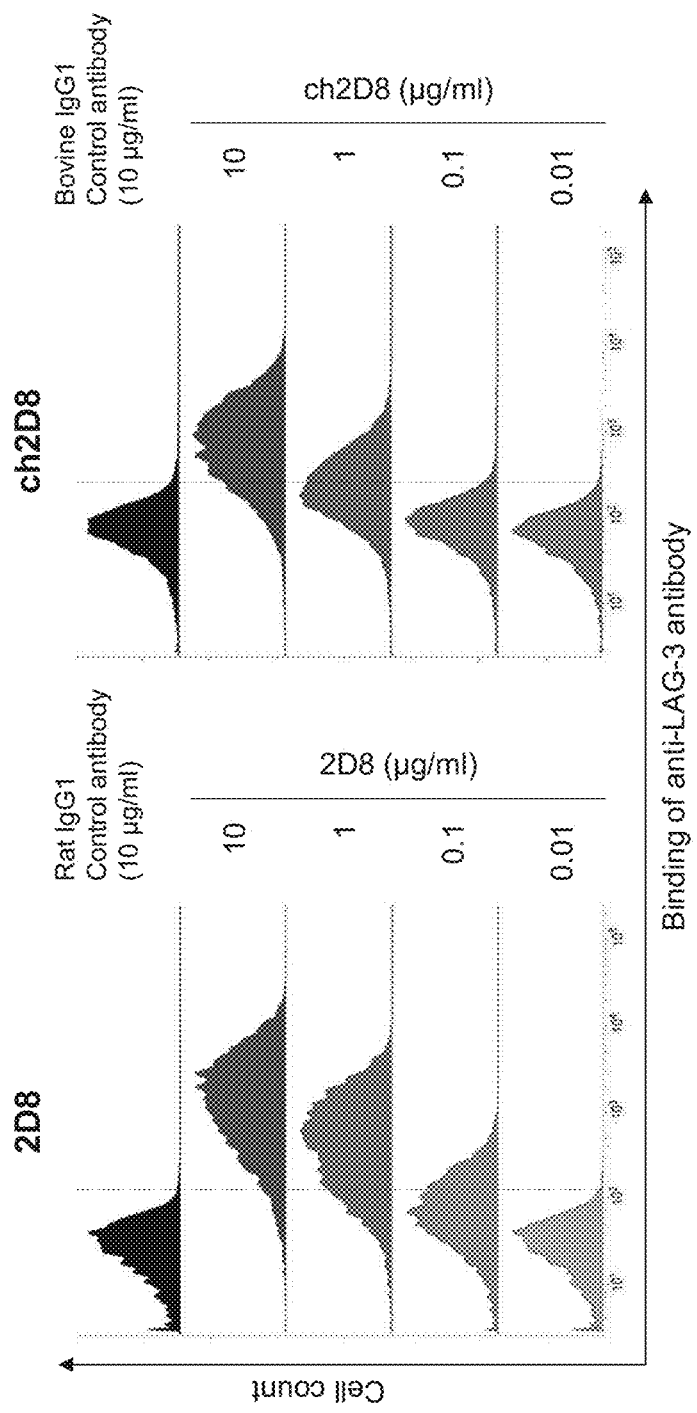
FIG. 4 Binding specificity of rat-bovine chimeric anti-bovine LAG-3 antibody ch2D8.

The experimental results are shown in FIG. 4. It was revealed that rat-bovine chimeric anti-bovine LAG-3 antibody ch2D8 binds to bovine LAG-3 expressing cells in the same manner as rat anti-bovine LAG-3 antibody 2D8.

2.9. Inhibitory Activity of Rat-Bovine Chimeric Anti-Bovine LAG-3 Antibody against Bovine LAG-3/MHC class II Binding (FIG. 5)

Using BL3.1 cell clone (bovine B-cell lymphoma-derived cell clone which highly expresses MHC class II) and bovine LAG-3-Ig (described above), bovine LAG-3/MHC class II binding inhibition by anti-LAG-3 antibodies was tested. First, rat anti-bovine LAG-3 antibody 2D8 or rat-bovine chimeric anti-bovine LAG-3 antibody ch2D8 at a final concentration of 0, 1.56, 3.12, 6.25, 12.5 or 25 μg/ml and bovine LAG-3-Ig at a final concentration of 3.3 μg/ml were mixed in 96-well plates, where they were reacted at 37° C. for 30 min. Subsequently, BL3.1 cell clone ($1 \times 10^5$ cells) was blocked with 10% inactivated goat serum (Life Technologies)-supplemented PBS at room temperature for 15 min, and reacted with the above reaction mixture at room temperature for 30 min. As negative control antibody, rat IgG1 (κ) isotype control (BD Biosciences) or bovine IgG1 antibody (Bethyl) was used. After washing, Alexa Fluor 647-labeled anti-rabbit IgG (H+L) goat F(ab')$_2$ (Life Technologies) which had been subjected to absorption treatment (37° C. 30 min) in advance with rat serum-derived IgG (Sigma-Aldrich) and bovine serum-derived IgG (Sigma-Aldrich) was reacted at room temperature for 30 min to thereby detect bovine LAG-3-Ig bound to cell surfaces. For analysis, FACS Verse (BD Biosciences) was used. For every washing operation and dilution of antibodies, PBS supplemented with 1% bovine serum albumin (Sigma-Aldrich) was used. Taking the proportion of LAG-3-Ig bound cells without antibody addition as 100%, the proportion of LAG-3-Ig bound cells at each antibody concentration was shown as relative value.

Figure 5:
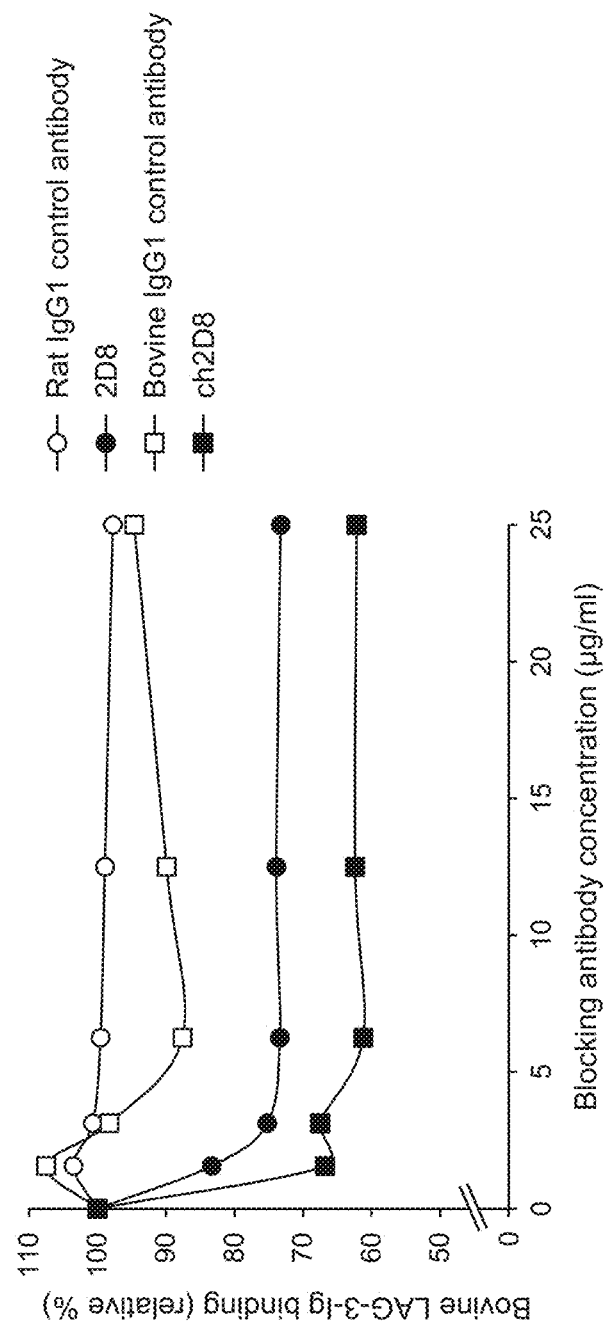
FIG. 5 Inhibitory activity of rat-bovine chimeric anti-bovine LAG-3 antibody ch2D8 against bovine LAG-3/MHC II binding FIG. 6 Changes in IFN-γ response due to rat-bovine chimeric anti-bovine LAG-3 antibody ch2D8.

The experimental results are shown in FIG. 5. It was revealed that rat-bovine chimeric anti-bovine LAG-3 antibody ch2D8 inhibited the binding of LAG-3-Ig to LAG-3 expressing cells by a comparable level to rat anti-bovine LAG-3 antibody 2D8, 2.10. Biological Activity Test Using Rat-Bovine Chimeric Anti-Bovine LAG-3 Antibody (FIG. 6)

In order to confirm that bovine LAG-3/MHC class 11 binding inhibition by rat-bovine chimeric anti-bovine LAG-3 antibody activates lymphocytes, a biological activity test was performed using IFN-γ production as an indicator. Briefly, PBMCs isolated from bovine peripheral blood were suspended in RPMI 1640 medium (Sigma-Aldrich) containing 10% inactivated fetal bovine serum (Cell Culture Technologies), penicillin 200 U/ml, streptomycin 200 μg/ml and 0.01% L-glutamine (Life Technologies) to give a concentration of $2 \times 10^6$ cells/ml. To the PBMCs, 10 μg/ml of rat anti-bovine LAG-3 antibody 2D8 or rat-bovine chimeric anti-bovine LAG-3 antibody ch2D8 was added. Culturing was then performed at 37° C. under 5% $CO_2$ for 2 days. As control antibodies, rat serum-derived IgG (Sigma-Aldrich) and bovine serum-derived IgG (Sigma-Aldrich) were used. Two days later, a culture supernatant was collected, and IFN-γ production was measured with Bovine IFN-γ ELISA Kit (BETYL). For each washing operation in ELISA, Auto Plate Washer BIO WASHER 50 (DS Pharma Biomedical) was used. Absorbance was measured with Microplate Reader MTP-650FA (Corona Electric).

Figure 6:
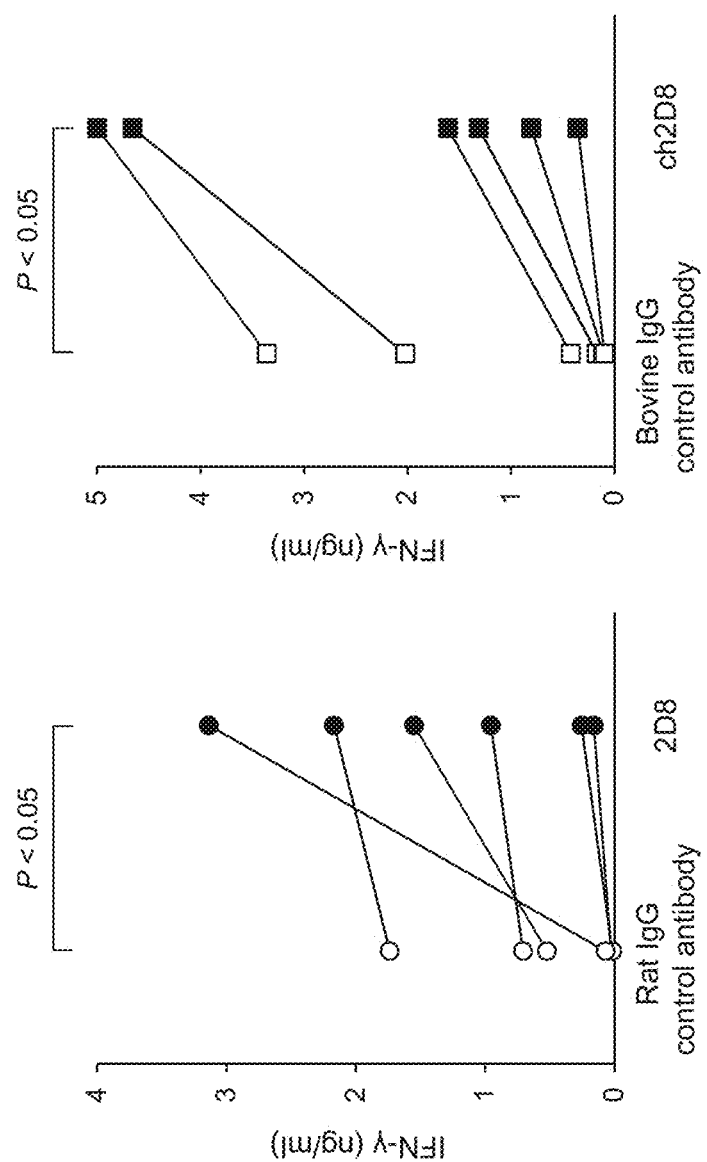

The experimental results are shown in FIG. 6. It was revealed that rat-bovine chimeric anti-bovine LAG-3 antibody ch2D8 increased bovine PBMCs' IFN-γ response in the same manner as rat anti-bovine LAG-3 antibody 2D8.

2.11. CDR Analysis of Rat Anti-Bovine LAG-3 Antibody

The complementarity-determining regions (CDRs) of rat anti-bovine LAG-3 antibody 2D8 were determined using NCBI IGBLAST (http://www.ncbi.nlm.nih.gov/igblast/). The results are shown in FIG. 1.

[Example 2] Application of Anti-LAG-3 Antibody to Other Animal Species

1. Materials, Methods and Experimental Results 1.1. Identification of Ovine and Water Buffalo LAG-3 Genes In order to determine the full-lengths of the coding sequences (CDSs) of water buffalo (*Bubalus bubalis*: Asian water buffalo) and ovine LAG-3 cDNAs, primers for amplifying the full lengths of CDSs from the nucleotide sequences of water buffalo and ovine LAG-3 genes (GenBank accession number AB608099 and XM_012129455) were first designed (buLAG-3 CDS F and R, ovLAG-3 CDS F and R), and then PCR was performed using a synthesized water buffalo or ovine PBMC-derived cDNA as a template. For the resultant amplified products, nucleotide sequences were determined with a capillary sequencer according to conventional methods.

```
Primer (buLAG-3 CDS F):
                                (SEQ ID NO: 65)
ATGCTGTGGGAGGCTTGGTTC Primer (buLAG-3 CDS R):
                                (SEQ ID NO: 66)
TCAGGGATGCTCTGGCTGCA Primer (ovLAG-3 CDS F):
                                (SEQ ID NO: 67)
ATGCTGTGGGAGGCTCAGTTCCAGG Primer (ovLAG-3 CDS R):
                                (SEQ ID NO: 68)
TCAGGGTTGCTCCGGCTGCA
```

1.2. Construction of Water Buffalo LAG-3 Expressing COS-7 Cells

In order to prepare a water buffalo LAG-3 expressing plasmid, PCR was performed using a synthesized water buffalo PBMC-derived cDNA as a template and primers designed by adding Sac and EcoRI recognition sites on the 5' side (buLAG-3-EGFP F and R). The resultant PCR products were digested with SacI (Takara) and EcoRI (Takara), then purified with FastGene Gel/PCR Extraction Kit (NIPPON Genetics) and cloned into pEGFP-N2 vector (Clontech) treated with restriction enzymes in the same manner. The expression plasmid of interest was extracted using FastGene Xpress Plasmid PLUS Kit (NIPPON Genetics) and stored at −30° C. until use in experiments. Hereinafter, the thus prepared plasmid is designated as pEGFP-N2-buLAG-3.

```
Primer (buLAG-3-EGFP F):
                                (SEQ ID NO: 69)
ATTGAGCTCATGCTGTGGGAGGCTTGGTT Primer (buLAG-3-EGFP R):
                                (SEQ ID NO: 70)
AATGAATTCGGGATGCTCTGGCTGCAGC
```

COS-7 cells at a density of $5 \times 10^4$ cells/cm$^2$ were subcultured in 6-well plates, and then cultured overnight in RPMI 1640 medium containing 10% inactivated fetal bovine serum (Invitrogen) and 0.01% L-glutamine (Life Technologies) at 37° C. in the presence of 5% $CO_2$. The pEGFP-N2-buLAG-3 or pEGFP-N2 (negative control) was introduced into COS-7 cells at 0.4 μg/cm$^2$ using Lipofectamine 2000 (Invitrogen). The cells were cultured for 48 hours (buLAG-3-EGFP expressing cells). In order to confirm the expression of water buffalo LAG-3 in the thus prepared expressing cells, intracellular localization of EGFP was visualized with an all-in-one fluorescence microscope BZ-9000 (KEYENCE).

1.3. Reactivity of Rat Anti-Bovine LAG-3 Antibody 2D8 with Water Buffalo LAG-3 (FIG. 7)

It was confirmed by flow cytometry that rat anti-bovine LAG-3 monoclonal antibody cross-reacts with water buffalo LAG-3. Water buffalo LAG-3-EGFP expressing COS cells were blocked with 10% inactivated goat serum (Invitrogen) supplemented PBS at room temperature for 15 min and reacted with 10 μg/ml of rat anti-bovine LAG-3 antibody 2D8 at room temperature for 30 min. After washing, the cells were reacted with APC-labeled anti-rat Ig goat antibody (Beckman Coulter) at room temperature for 30 min. As a negative control antibody, rat IgG1 (κ) isotype control (BD Bioscience) was used. For analysis. FACS Verse (BD Bioscience) was used. For every washing operation and dilution of antibodies, 1% bovine serum albumin (Sigma-Aldrich) supplemented PBS was used.

Figure 7:
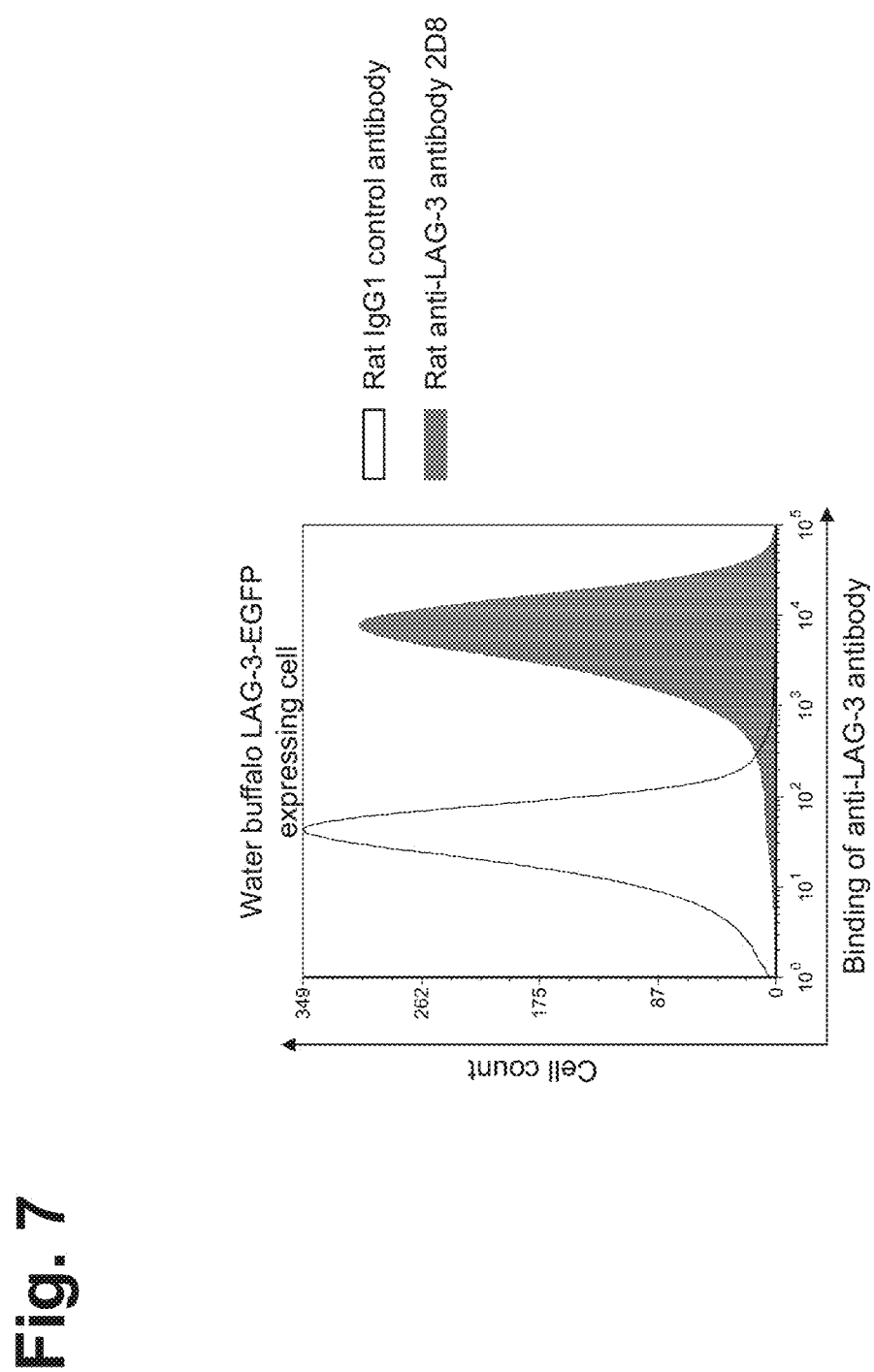
FIG. 7 Cross-reactivity of rat anti-bovine LAG-3 antibody 2D8 with water buffalo LAG-3

Experimental results are shown in FIG. 7. It was confirmed that rat anti-bovine LAG-3 antibody 2D8 binds to water buffalo LAG-3 expressing cells.

1.4. Reactivity of Rat Anti-Bovine LAG-3 Antibody 2D8 with Ovine Lymphocytes (FIG. 8)

Peripheral blood mononuclear cells (PBMCs) were isolated from ovine peripheral blood by density gradient centrifugation using Percoll (GE Healthcare). The isolated ovine PBMCs were suspended in RPMI 1640 medium (Sigma-Aldrich) containing 10% inactivated fetal calf serum (Invitrogen), penicillin 200 U/ml, streptomycin 200 µg/ml and 0.01% L-glutamine (Life Technologies). Cell density was adjusted to $2 \times 10^6$ cells/ml. To these PBMCs, phorbol 12-myristate acetate (PMA) 20 ng/ml and ionomycin 1 µg/ml (Sigma-Aldrich) were added, followed by culturing overnight at 37° C. under 5% $CO_2$. Cultured PBMCs were harvested and blocked with 10% inactivated goat serum (Invitrogen) supplemented PBS at room temperature for 15 min. Then, rat anti-bovine LAG-3 antibody 2D8 was reacted at room temperature for 30 min. As a negative control, rat serum-derived IgG (Sigma-Aldrich) was used. After washing, labeling was performed using APC-labeled goat anti-rat Ig antibody (Beckman Coulter) at room temperature for 30 min. Subsequently, a reaction was performed with mouse anti-ovine CD8 antibody (38.65, AbD Serotec) at room temperature for 30 min. After washing, labeling was performed using PerCP/Cy5.5-labeled goat anti-mouse IgG2a antibody (Santa Cruz) at room temperature for 30 min. After further washing, a reaction was performed with Alexa Flour 488-labled anti-ovine CD21 mouse antibody (GB25A, VMRD) at room temperature for 30 min. For the labeling of GB25A, Zenon Labeling Kit (Life Technologies) was used. For analysis, FACS Verse (BD Biosciences) was used. Every washing operation and dilution of antibodies, 1% bovine serum albumin (Sigma-Aldrich) supplemented PBS was used.

Figure 8:
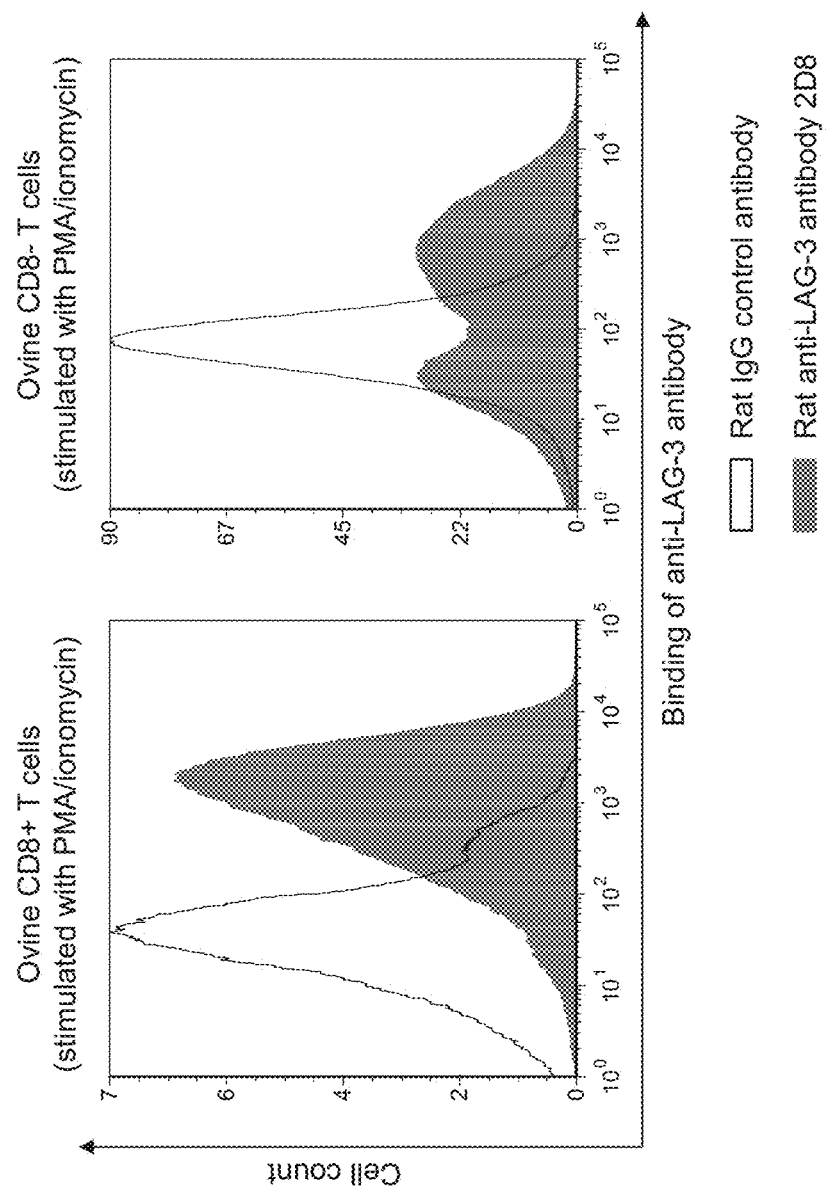
FIG. 8 Cross-reactivity of rat anti-bovine LAG-3 antibody 2D8 with ovine T cells

The experimental results are shown in FIG. 8. Rat anti-bovine LAG-3 antibody 2D8 strongly bound to ovine $CD8^+$ T cells ($CD21^-$ $CD8^+$ cells) and $CD8^-$ T cells ($CD21^-$ $CD8^-$ cells; i.e., a cell population containing $CD4^+$ T cells and γ δ T cells), both activated by PMA/ionomycin stimulation.

All publications, patents and patent applications cited herein are incorporated herein by reference in their entirety.

INDUSTRIAL APPLICABILITY

The anti-LAG-3 antibody of the present invention is applicable to prevention and/or treatment of cancers and infections in animals.

SEQUENCE LISTING FREE TEXT

<SEQ ID NO: 1>
SEQ ID NO: 1 shows the amino acid sequence of the light chain variable region (VL) of rat anti-bovine LAG-3 antibody. Underlined parts: CDR1, CDR2 and CDR3 in this order from the NH2 terminus.

MMSPVQSLFLLLLWILGTNGDVVLTQTPPTLSATIGQSVSISCRSSQSLL
DSDGNTYLNWLLQRPGQSPQLLIYSVSNLESGVPNRFSGSGSETDFTLKI
SGVEAEDLGVYYCMQATHVPFTFGSGTKLEIK

<SEQ ID NO: 2>
SEQ ID NO: 2 shows the amino acid sequence of the heavy chain variable region (VH) of rat anti-bovine LAG-3 antibody. Underlined parts: CDR1, CDR2 and CDR3 in this order from the NH2 terminus.

MVLLELVSVIALFQGVHCEVQLVESGGGLVQPKGSLRLSCAASGFDFDTY
PMSWVRQAPGKGLDWVASITIKTHNYATLYAASVKERFTISRDDSQSMVY
LQMNNLKTEDTALYYCNREDFDYWGQGVMVTVSS

<SEQ ID NO: 3>
SEQ ID NO: 3 shows the amino acid sequence of the light chain constant region (CL) of a bovine antibody (bovine Ig lambda, GenBank: X62917).

QPKSPPSVTLFPPSTEELNGNKATLVCLISDFYPGSVTVVWKADGSTITR
NVETTRASKQSNSKYAASSYLSLTSSDWKSKGSYSCEVTHEGSTVTKTVK
PSECS

<SEQ ID NO: 4>
SEQ ID NO: 4 shows the amino acid sequence of the heavy chain constant region (CH) of a bovine antibody (bovine IgG1, modified from GenBank: X62916). Mutated sites are underlined. Amino acid sequences and mutations: 119 E→P, 120 L→V, 121 P→A, 122 G→deletion, 216 A→S, 217 P→S

ASTTAPKVYPLSSCCGDKSSSTVTLGCLVSSYMPEPVTVTWNSGALKSGV

HTFPAVLQSSGLYSLSSMVTVPGSTSGQTFTCNVAHPASSTKVDKAVDPT

CKPSPCDCCPPPPVAGPSVFIFPPKPKDTLTISGTPEVTCVVVDVGHDDP

EVKFSWFVDDVEVNTATTKPREEQFNSTYRVVSALRIQHQDWTGGKEFKC

KVHNEGLPSSIVRTISRTKGPAREPQVYVLAPPQEELSKSTVSLTCMVTS

FYPDYIAVEWQRNGQPESEDKYGTTPPQLDADSSYFLYSKLRVDRNSWQE

GDTYTCVVMHEALHNHYTQKSTSKSAGK

<SEQ ID NO: 5>
SEQ ID NO: 5 shows the nucleotide sequence of the VL of rat anti-bovine LAG-3 antibody-.

ATGATGAGTCCTGTCCAATCCCTGTTTTTGTTATTGCTTTGGATTCTGGG

AACCAATGGTGATGTTGTGCTGACCCAGACTCCACCCACTTTATCGGCTA

CCATTGGACAATCGGTCTCCATCTCTTGCAGGTCAAGTCAGAGTCTCTTA

GATAGTGATGGAAATACCTATTTAAATTGGTTGCTACAGAGGCCAGGCCA

ATCTCCACAGCTTCTAATTTATTCGGTATCCAACCTGGAATCTGGGGTCC

CCAACAGGTTCAGTGGCAGTGGGTCAGAAACAGATTTCACACTCAAATC

AGTGGAGTGGAGGCTGAAGATTTGGGAGTTTATTACTGCATGCAAGCTAC

CCATGTTCCATTCACGTTCGGCTCAGGGACGAAGTTGGAAATAAAA

The nucleotide sequence of SEQ ID NO: 5 after codon optimization is shown in <SEQ ID NO: 11>.

ATGATGTCTCCCGTCCAAAGCTTGTTCCTGCTTCTCCTCTGGATTCTGGG

CACAAACGGAGATGTGGTTCTCACCCAGACCCCCCCTACTCTGTCTGCCA

CCATCGGCCAGAGCGTGTCCATATCCTGTCGCAGCTCCCAAAGCCTGCTG

GACTCCGATGGGAATACTTACCTGAATTGGCTGTTGCAGCGGCCTGGCCA

-continued
GTCCCCCCAGCTGTTGATCTACAGCGTTAGCAATCTGGAAAGCGGGGTCC

CCAACCGATTCTCCGGAAGCGGCTCCGAGACCGATTTTACCCTCAAGATC

TCCGGCGTGGAAGCCGAGGACCTGGGAGTGTATTATTGCATGCAGGCCAC

CCATGTGCCCTTCACCTTCGGTAGCGGTACCAAGTTGGAGATCAAG

<SEQ ID NO: 6>
SEQ ID NO: 6 shows the nucleotide sequence of the VH of rat anti-bovine LAG-3 antibody.

ATGGTTCTCCTGGAGTTGGTTTCCGTGATTGCTCTTTTTCAAGGCGTGCA

TTGTGAGGTGCAGCTTGTTGAGTCTGGTGGAGGGCTGGTGCAGCCTAAGG

GGTCATTGAGACTCTCATGTGCAGCCTCTGGATTTGACTTCGATACTTAT

CCCATGAGCTGGGTCCGCCAGGCTCCAGGAAAGGGTCTGGATTGGGTTGC

TAGTATAACCATTAAGACTCATAATTATGCAACACTTTATGCTGCTTCAG

TGAAAGAGAGATTCACCATCTCCAGAGATGACTCACAAAGCATGGTTTAC

TTGCAAATGAACAACTTGAAAACTGAGGACACAGCCTTGTATTACTGTAA

CAGGGAGGACTTTGATTACTGGGGCCAAGGAGTCATGGTCACAGTCTCCT

CA

The nucleotide sequence of SEQ ID NO: 6 after codon optimization is shown in <SEQ ID NO: 12>.

ATGGTGCTTCTCGAGCTGGTCAGCGTGATTGCTCTGTTTCAGGGCGTGCA

CTGCGAAGTGCAGCTGGTGGAGAGTGGTGGTGGGCTCGTGCAACCAAAAG

GCAGTCTCAGGCTGAGTTGTGCCGCCTCCGGATTCGATTTCGACACCTAC

CCAATGAGCTGGGTCAGGCAAGCCCCAGGGAAAGGACTCGATTGGGTGGC

AAGCATTACCATCAAGACACACAATTATGCTACCCTGTATGCCGCAAGCG

TAAAGGAACGCTTTACCATCTCCCGCGATGATAGCCAGTCCATGGTATAT

TTGCAAATGAATAATTTGAAGACAGAAGATACCGCTTTGTATTATTGCAA

CAGAGAAGATTTTGATTATTGGGGCAGGGGTGATGGTAACCGTGTCCA

GC

<SEQ ID NO: 7>
SEQ ID NO: 7 shows the nucleotide sequence of the CL of a bovine antibody (bovine Ig lambda, GenBank: X62917).

CAGCCCAAGTCCCCACCCTCGGTCACCCTGTTCCCGCCCTCCACGGAGGA

GCTCAACGGCAACAAGGCCACCCTGGTGTGTCTCATCAGCGACTTCTACC

CGGGTAGCGTGACCGTGGTCTGGAAGGCAGACGGCAGCACCATCACCCGC

AACGTGGAGACCACCCGGGCCTCCAAACAGAGCAACAGCAAGTACGCGGC

CAGCAGCTACCTGAGCCTGACGAGCAGCGACTGGAAATCGAAAGGCAGTT

ACAGCTGCGAGGTCACGCACGAGGGGAGCACCGTGACGAAGACAGTGAAG

CCCTCAGAGTGTTCTTAG

The nucleotide sequence of SEQ ID NO: 7 after codon optimization is shown in <SEQ ID NO: 13>.

CAGCCTAAGTCCCCTCCTTCAGTCACCCTGTITTCCACCATCTACCGAAGA

ACTCAACGGGAATAAAGCAACACTGGTGTGCCTTATTTCTGATTTTTACC

CAGGGTCTGTGACAGTGGTTTGGAAAGCTGACGGTTCAACAATTACAAGA

AACGTGGAGACAACAAGGGCTTCTAAGCAGTCAAACTCTAAGTATGCTGC

AAGTTCTTACCTTTCTCTTACAAGTAGTGACTGGAAAAGTAAGGGCAGTT

ATTCATGCGAGGTCACTCACGAGGGAAGTACTGTAACTAAAACTGTAAAA

CCATCAGAGTGTTCATAG

<SEQ ID NO: 8>
SEQ ID NO: 8 shows the nucleotide sequence (after codon optimization) of the CH of a bovine antibody (bovine IgG1, modified from GenBank: X62916).

GCTAGCACCACAGCACCTAAAGTTTACCCTCTGTCTTCCTGCTGCGGCGA

CAAGTCTTCATCAACTGTTACTCTTGGATGCCTGGTCTCAAGTTACATGC

CCGAGCCCGTGACAGTGACCTGGAACTCAGGCGCTCTGAAGTCTGGAGTG

CACACATTTCCAGCTGTGCTTCAGTCTAGCGGCCTGTATTCCCTCAGCTC

TATGGTTACTGTACCTGGTAGCACCAGCGGACAGACTTTCACCTGTAATG

TTGCCCATCCCGCATCTTCTACCAAGGTCGATAAAGCCGTTGACCCCACT

TGCAAACCATCCCCTTGTGATTGTTGTCCACCCCCTCCAGTGGCTGGCCC

TTCCGTCTTCATTTTCCCTCCTAAACCTAAGGATACTCTGACCATCTCAG

GGACACCCGAGGTCACCTGTGTCGTCGTGGACGTGGGACATGACGACCCA

GAAGTCAAGTTCTCATGGTTCGTGGACGATGTGGAGGTGAACACAGCAAC

AACAAAGCCCAGAGAAGAACAGTTTAACAGCACATATCGGGTGGTCAGCG

CCTTGCGTATTCAGCACCAGGACTGGACTGGTGGCAAGGAGTTTAAGTGC

AAGGTGCATAACGAAGGTCTGCCCTCTTCTATAGTGAGAACTATCTCCCG

AACTAAGGGCCCCGCTCGGGAGCCCCAGGTTTACGTCCTTGCTCCCCCTC

AGGAGGAACTGAGTAAATCAACCGTGAGTCTCACCTGTATGGTTACCTCA

TTTTACCCAGACTACATCGCCGTAGAGTGGCAGAGGAATGGACAGCCAGA

GTCTGAGGACAAATACGGCACTACTCCTCCCCAACTGGATGCCGACTCTT

CCTACTTCCTCTACTCCAAATTGCGAGTTGACCGGAACTCATGGCAGGAG

GGGGACACATACACATGCGTCGTTATGCACGAGGCCCTGCACAACCATTA

CACCCAGAAGTCCACATCTAAAAGTGCAGGTAAGTAA

<SEQ ID NO: 9>
SEQ ID NO: 9 shows the amino acid sequence of a chimeric light chain consisting of the VL of rat anti-bovine LAG-3 antibody and the CL of a bovine antibody.

MMSPVQSLFLLLLWILGTNGDVVLIQTPPTLSATIGQSVSISCRSSQSLL

DSDGNTYLNWLLQRPGQSPQLLIYSVSNLESGVPNRFSGSGSETDFTLKI

SGVEAEDLGVYYCMQATHVPFTFGSGTKLEIKQPKSPPSVTLFPPSTEEL

NGNKATLVCLISDFYPGSVTVVWKADGSTITRNVETTRASKQSNSKYAAS

SYLSLTSSDWKSKGSYSCEVTHEGSTVTKTVKPSECS

<SEQ ID NO: 10>
SEQ ID NO: 10 shows the amino acid sequence of a chimeric heavy chain consisting of the VH of rat anti-bovine LAG-3 antibody and the CH of a bovine antibody (bovine IgG1, modified from GenBank: X62916).

MVLLELVSVIALFQGVHCEVQLVESGGGLVQPKGSLRLSCAASGFDFDTY
PMSWVRQAPGKGLDWVASITIKTHNYATLYAASVKERFTISRDDSQSMVY
LQMNNLKTEDTALYYCNREDFDYWGQGVMVTVSSASTTAPKVYPLSSCCG
DKSSSTVTLGCLVSSYMPEPVTVTWNSGALKSGVHTFPAVLQSSGLYSLS
SMVTVPGSTSGQTFTCNVAHPASSTKVDKAVDPTCKPSPCDCCPPPPVAG
PSVFIFPPKPKDTLTISGTPEVTCVVVDVGHDDPEVKFSWFVDDVEVNTA
TTKPREEQFNSTYRVVSALRIQHQDWTGGKEFKCKVHNEGLPSSIVRTIS
RTKGPAREPQVYVLAPPQEELSKSTVSLTCMVTSFYPDYIAVEWQRNGQP
ESEDKYGTTPPQLDADSSYFLYSKLRVDRNSWQEGDTYTCVVMHEALHNH
YTQKSTSKSAGK

<SEQ ID NO: 14>
SEQ ID NO: 14 shows the nucleotide sequence (after codon optimization) of a chimeric light chain consisting of the VL of rat anti-bovine LAG-3 antibody and the CL of a bovine antibody.

ATGATGTCTCCCGTCCAAAGCTTGTTCCTGCTTCTCCTCTGGATTCTGGG
CACAAACGGAGATGTGGTTCTCACCCAGACCCCCCCTACTCTGTCTGCCA
CCATCGGCCAGAGCGTGTCCATATCCTGTCGCAGCTCCCAAAGCCTGCTG
GACTCCGATGGGAATACTTACCTGAATTGGCTGTTGCAGCGGCCTGGCCA
GTCCCCCCAGCTGTTGATCTACAGCGTTAGCAATCTGGAAAGCGGGGTCC
CCAACCGATTCTCCGGAAGCGGCTCCGAGACCGATTTTACCCTCAAGATC
TCCGGCGTGGAAGCCGAGGACCTGGGAGTGTATTATTGCATGCAGGCCAC
CCATGTGCCCTTCACCTTCGGTAGCGGTACCAAGTTGGAGATCAAGCAGC
CTAAGTCCCCTCCTTCAGTCACCCTGTTTCCACCATCTACCGAAGAACTC
AACGGGAATAAAGCAACACTGGTGTGCCTTATTTCTGATTTTTACCCAGG
GTCTGTGACAGTGGTTTGGAAAGCTGACGGTTCAACAATTACAAGAAACG
TGGAGACAACAAGGGCTTCTAAGCAGTCAAACTCTAAGTATGCTGCAAGT
TCTTACCTTTCTCTTACAAGTAGTGACTGGAAAAGTAAGGGCAGTTATTC
ATGCGAGGTCACTCACGAGGGAAGTACTGTAACTAAAACTGTAAAACCAT
CAGAGTGTTCATAG

<SEQ ID NO: 15>
SEQ ID NO: 15 shows the nucleotide sequence (after codon optimization) of a chimeric heavy chain consisting of the VH of rat anti-bovine LAG-3 antibody and the CH of a bovine antibody (bovine IgG1, modified from GenBank: X62916).

ATGGTGCTTCTCGAGCTGGTCAGCGTGATTGCTCTGTTTCAGGGCGTGCA
CTGCGAAGTGCAGCTGGTGGAGAGTGGTGGTGGGCTCGTGCAACCAAAAG
GCAGTCTCAGGCTGAGTTGTGCCGCCTCCGGATTCGATTTCGACACCTAC
CCAATGAGCTGGGTCAGGCAAGCCCCAGGGAAAGGACTCGATTGGGTGGC
AAGCATTACCATCAAGACACACAATTATGCTACCCTGTATGCCGCAAGCG
TAAAGGAACGCTTTACCATCTCCCGCGATGATAGCCAGTCCATGGTATAT
TTGCAAATGAATAATTTGAAGACAGAAGATACCGCTTTGTATTATTGCAA
CAGAGAAGATTTTGATTATTGGGGGCAGGGGGTGATGGTAACCGTGTCCA
GCGCTAGCACCACAGCACCTAAAGTTTACCCTCTGTCTTCCTGCTGCGGC
GACAAGTCTTCATCAACTGTTACTCTTGGATGCCTGGTCTCAAGTTACAT
GCCCGAGCCCGTGACAGTGACCTGGAACTCAGGCGCTCTGAAGTCTGGAG
TGCACACATTTCCAGCTGTGCTTCAGTCTAGCGGCCTGTATTCCCTCAGC
TCTATGGTTACTGTACCTGGTAGCACCAGCGGACAGACTTTCACCTGTAA
TGTTGCCCATCCCGCATCTTCTACCAAGGTCGATAAAGCCGTTGACCCCA
CTTGCAAACCATCCCCTTGTGATTGTTGTCCACCCCCTCCAGTGGCTGGC
CCTTCCGTCTTCATTTTCCCTCCTAAACCTAAGGATACTCTGACCATCTC
AGGGACACCCGAGGTCACCTGTGTCGTCGTGGACGTGGGACATGACGACC
CAGAAGTCAAGTTCTCATGGTTCGTGGACGATGTGGAGGTGAACACAGCA
ACAACAAAGCCCAGAGAAGAACAGTTTAACAGCACATATCGGGTGGTCAG
CGCCTTGCGTATTCAGCACCAGGACTGGACTGGTGGCAAGGAGTTTAAGT
GCAAGGTGCATAACGAAGGTCTGCCCTCTTCTATAGTGAGAACTATCTCC
CGAACTAAGGGCCCCGCTCGGGAGCCCCAGGTTTACGTCCTTGCTCCCCC
TCAGGAGGAACTGAGTAAATCAACCGTGAGTCTCACCTGTATGGTTACCT
CATTTTACCCAGACTACATCGCCGTAGAGTGGCAGAGGAATGGACAGCCA
GAGTCTGAGGACAAATACGGCACTACTCCTCCCCAACTGGATGCCGACTC
TTCCTACTTCCTCTACTCCAAATTGCGAGTTGACCGGAACTCATGGCAGG
AGGGGGACACATACACATGCGTCGTTATGCACGAGGCCCTGCACAACCAT
TACACCCAGAAGTCCACATCTAAAAGTGCAGGTAAGTAA

<SEQ ID NO: 16>
SEQ ID NO: 16 shows the amino acid sequence (QSLL-DSDGNTY) of CDR11 of the VL of rat anti-bovine LAG-3 antibody 2D8.

<SEQ ID NO: 17>
SEQ ID NO: 17 shows the amino acid sequence (MQATHVPFT)

of CDR3 of the VL of rat anti-bovine LAG-3 antibody 2D8.

<SEQ ID NO: 18>
SEQ ID NO: 18 shows the amino acid sequence (GFDFDTYP)

of CDR1 of the VH of rat anti-bovine LAG-3 antibody 2D8.

<SEQ ID NO: 19>
SEQ ID NO: 19 shows the amino acid sequence (ITIKTHNYAT)

of CDR2 of the VH of rat anti-bovine LAG-3 antibody 2D8.

<SEQ ID NO: 20>
SEQ ID NO: 20 shows the amino acid sequence (NREDFDY)

of CDR3 of the VH of rat anti-bovine LAG-3 antibody 2D8.
<SEQ ID NO: 21>
SEQ ID NO: 21 shows the amino acid sequence of the CH (CH1-CH3) of a bovine antibody (IgG1 variant 1).
<SEQ ID NO: 22>
SEQ ID NO: 22 shows the amino acid sequence of the CH (CH1-CH3) of a bovine antibody (IgG1 variant 2).
<SEQ ID NO: 23>
SEQ ID NO: 23 shows the amino acid sequence of the CH (CH1-CH3) of a bovine antibody (IgG1 variant 3).
<SEQ ID NO: 24>
SEQ ID NO: 24 shows the amino acid sequence of the CH (CH1-CH3) of a bovine antibody (IgG2 variant 1).
<SEQ ID NO: 25>
SEQ ID NO: 25 shows the amino acid sequence of the CH (CH1-CH3) of a bovine antibody (IgG2 variant 2).
<SEQ ID NO: 26>
SEQ ID NO: 26 shows the amino acid sequence of the CH (CH1-CH3) of a bovine antibody (IgG2 variant 3).
<SEQ ID NO: 27>
SEQ ID NO: 27 shows the amino acid sequence of the CH (CH1-CH3) of a bovine antibody (IgG3 variant 1).
<SEQ ID NO: 28>
SEQ ID NO: 28 shows the amino acid sequence of the CH (CH1-CH3) of a bovine antibody (IgG3 variant 2).
<SEQ ID NO: 29>
SEQ ID NO: 29 shows the nucleotide sequence of the CH (CH1-CH3) of a bovine antibody (IgG1 variant 1).
<SEQ ID NO: 30>
SEQ ID NO: 30 shows the nucleotide sequence of the CH (CH1-CH3) of a bovine antibody (IgG1 variant 2).
<SEQ ID NO: 31>
SEQ ID NO: 31 shows the nucleotide sequence of the CH (CH1-CH3) of a bovine antibody (IgG1 variant 3).
<SEQ ID NO: 32>
SEQ ID NO: 32 shows the nucleotide sequence of the CH (CH1-CH3) of a bovine antibody (IgG2 variant 1).
<SEQ ID NO: 33>
SEQ ID NO: 33 shows the nucleotide sequence of the CH (CH1-CH3) of a bovine antibody (IgG2 variant 2).
<SEQ ID NO: 34>
SEQ ID NO: 34 shows the nucleotide sequence of the CH (CH1-CH3) of a bovine antibody (IgG2 variant 3).
<SEQ ID NO: 35>
SEQ ID NO: 35 shows the nucleotide sequence of the CH (CH1-CH3) of a bovine antibody (IgG3 variant 1).
<SEQ ID NO: 36>
SEQ ID NO: 36 shows the nucleotide sequence of the CH (CH1-CH3) of a bovine antibody (IgG3 variant 2).
<SEQ ID NO: 37>
SEQ ID NO: 37 shows the amino acid sequence of the CH (CH1-CH3) of an ovine antibody (IgG1).
<SEQ ID NO: 38>
SEQ ID NO: 38 shows the nucleotide sequence of the CH (CH1-CH3) of an ovine antibody (IgG1).
<SEQ ID NO: 39>
SEQ ID NO: 39 shows the amino acid sequence of the CH (CH1-CH3) of an ovine antibody (IgG2).
<SEQ ID NO: 40>
SEQ ID NO: 40 shows the nucleotide sequence of the CH (CH1-CH3) of an ovine antibody (IgG2).
<SEQ ID NO: 41>
SEQ ID NO: 41 shows the amino acid sequence of the light chain (Ig kappa(CK)) constant region of an ovine antibody.
<SEQ ID NO: 42>
SEQ ID NO: 42 shows the nucleotide sequence of the light chain (Ig kappa(CK)) constant region of an ovine antibody.
<SEQ ID NO: 43>
SEQ ID NO: 43 shows the amino acid sequence of the light chain (Ig lambda(CL)) constant region of an ovine antibody.
<SEQ ID NO: 44>
SEQ ID NO: 44 shows the nucleotide sequence of the light chain (Ig lambda(CL)) constant region of an ovine antibody.
<SEQ ID NO: 45>
SEQ ID NO: 45 shows the amino acid sequence of the CH (CH1-CH3) of a water buffalo antibody (presumed to be IgG1).
<SEQ ID NO: 46>
SEQ ID NO: 46 shows the nucleotide sequence of the CH (CH1-CH3) of a water buffalo antibody (presumed to be IgG1).
<SEQ ID NO: 47>
SEQ ID NO: 47 shows the amino acid sequence of the CH (CH1-CH3) of a water buffalo antibody (presumed to be IgG2).
<SEQ ID NO: 48>
SEQ ID NO: 48 shows the nucleotide sequence of the CH (CH1-CH3) of a water buffalo antibody (presumed to be IgG2).
<SEQ ID NO: 49>
SEQ ID NO: 49 shows the amino acid sequence of the CH (CH1-CH3) of a water buffalo antibody (presumed to be IgG3).
<SEQ ID NO: 50>
SEQ ID NO: 50 shows the nucleotide sequence of the CH (CH1-CH3) of a water buffalo antibody (presumed to be IgG3).
<SEQ ID NO: 51>
SEQ ID NO: 51 shows the amino acid sequence of the light chain (presumed to be Ig lambda) constant region (CL) of a water buffalo antibody.
<SEQ ID NO: 52>
SEQ ID NO: 52 shows the nucleotide sequence of the light chain (presumed to be Ig lambda) constant region (CL) of a water buffalo antibody.
<SEQ ID NO: 53>
SEQ ID NO: 53 shows the amino acid sequence of the CH (CH1-CH3) of a human antibody (IgG4 variant 1).
<SEQ ID NO: 54>
SEQ ID NO: 54 shows the nucleotide sequence of the CH (CH1-CH3) of a human antibody (IgG4 variant 1).
<SEQ ID NO: 55>
SEQ ID NO: 55 shows the amino acid sequence of the CH (CH1-CH3) of a human antibody (IgG4 variant 2).
<SEQ ID NO: 56>
SEQ ID NO: 56 shows the nucleotide sequence of the CH (CH1-CH3) of a human antibody (IgG4 variant 2).
<SEQ ID NO: 57>
SEQ ID NO: 57 shows the amino acid sequence of the CH (CH1-CH3) of a human antibody (IgG4 variant 3).
<SEQ ID NO: 58>
SEQ ID NO: 58 shows the nucleotide sequence of the CH (CH1-CH3) of a human antibody (IgG4 variant 3).
<SEQ ID NO: 59>
SEQ ID NO: 59 shows the amino acid sequence of the CL of a human antibody.

<SEQ ID NO: 60>
SEQ ID NO: 60 shows the nucleotide sequence of the CL of a human antibody.

<SEQ ID NOS: 61-70>
SEQ ID NOS: 61-70 show the nucleotide sequences of primers boLAG-3-EGFP F, boLAG-3-EGFP R, boLAG-3-Ig F, boLAG-3-Ig R, buLAG-3 CDS F, buLAG-3 CDS R, ovLAG-3 CDS F, ovLAG-3 CDS R, buLAG-3-EGFP F, and buLAG-3-EGFP R in this order.

<SEQ ID NO: 71>
SEQ ID NO: 71 shows the amino acid sequence of the full length of bovine LAG-3.

MLWEAWFQVWLFLQLLWAAAVEAPEPGAEVPVVWAQEGAPAQLPCSPTIP

LQDLSLPRTRQVTWQHVPESGSAAPTPRGPGPRRYTVLRLAPGGLRIGKL

PLQPRVQLEEMGLQRGDFSLWLRPARRADAGEYHAAVRFGNRALACRLRL

RVGQAAVTASPPGPLWTSSWVVLNCSFSRPDLPASVHWFRGPGRVPVQES

PHHHLVGNFLFLPQVSSLDSGTWGCSLTYRDGFNVSITYNLAVLGLEPRA

TLTVYAGAGSKVELPCRLPPGVGIQSSLTAMWTPPGEGPDLLVAGDRNNF

TLRLEAVGQAQAGTYTCRVHLQGRQLSATVTLAVITVTPKPYGSSGSLRK

PFCEVTPASGQERFVWSPLDKRSQRRSPGPWLLTPDARPLSQPWQCHLYQ

GERLLGTAVYLTELSHPGAQRSGRALGAGRTAHLPLLILGLLFLLLLVTG

ASSFHLWRRQWRPRRFSALEHGTHPSQASSKTGELEPELEPEPDPEVEPE

PEPEPESQPQLQPEQP*

<SEQ ID NO: 72>
SEQ ID NO: 72 shows the amino acid sequence of a part of the extracellular region of bovine LAG-3 which corresponds to amino acid numbers 71 to 99).

GSAAPTPRGPGPRRYTVLRLAPGGLRIGK.

The invention claimed is:

1. An anti-LAG-3 antibody comprising (a) a light chain comprising a light chain variable region containing CDR1 having the amino acid sequence of QSLLDSDGNTY (SEQ ID NO: 16), CDR2 having the amino acid sequence of SVS and CDR3 having the amino acid sequence of MQATHVPFT (SEQ ID NO: 17) and the light chain constant region of an antibody of bovine; and (b) a heavy chain comprising a heavy chain variable region containing CDR1 having the amino acid sequence of GFDFDTYP (SEQ ID NO: 18), CDR2 having the amino acid sequence of ITIKTH-NYAT (SEQ ID NO: 19) and CDR3 having the amino acid sequence of NREDFDY (SEQ ID NO: 20) and the heavy chain constant region of an antibody of bovine, wherein the light chain constant region of the bovine antibody has the amino acid sequence as shown in SEQ ID NO: 3 and the heavy chain constant region of the bovine antibody has the amino acid sequence as shown in SEQ ID NO: 4.

2. The antibody of claim 1, wherein the light chain variable region and the heavy chain variable region are derived from rat.

3. The antibody of claim 2, wherein the light chain variable region is the light chain variable region of a rat anti-bovine LAG-3 antibody and the heavy chain variable region is the heavy chain variable region of a rat anti-bovine LAG-3 antibody.

4. The antibody of claim 3, wherein the light chain variable region has the amino acid sequence as shown in SEQ ID NO: 1 and the heavy chain variable region has the amino acid sequence as shown in SEQ ID NO: 2.

5. The antibody of claim 1 which has a four-chain structure comprising two light chains and two heavy chains.

6. A pharmaceutical composition comprising the antibody of claim 1 as an active ingredient.

7. A method to treat cancer and/or infection in cattle, buffalo or sheep comprising administering an effective amount of the pharmaceutical composition of claim 6 to cattle, buffalo or sheep in need thereof so as to treat said cancer and/or infection.

8. The method of claim 7, wherein the cancer and/or infection is selected from the group consisting of neoplastic diseases, leukemia, Johne's disease, anaplasmosis, bacterial mastitis, mycotic mastitis, mycoplasma infections, tuberculosis, *Theileria orientalis* infection, cryptosporidiosis, coccidiosis, trypanosomiasis and leishmaniasis.

9. An artificial genetic DNA encoding the antibody of claim 1.

10. A vector comprising the artificial genetic DNA of claim 9.

11. A host cell transformed with the vector of claim 10.

12. A method of preparing an antibody, comprising culturing the host cell of claim 11 and collecting an anti-LAG-3 antibody from the resultant culture.

\* \* \* \* \*

UNITED STATES PATENT AND TRADEMARK OFFICE
CERTIFICATE OF CORRECTION

PATENT NO. : 11,198,730 B2  
APPLICATION NO. : 16/325150  
DATED : December 14, 2021  
INVENTOR(S) : Konnai et al.

Page 1 of 1

It is certified that error appears in the above-identified patent and that said Letters Patent is hereby corrected as shown below:

In the Claims

In Column 125, Line 67, in Claim 1, delete "SEO" and insert --SEQ-- therefor

In Column 126, Line 53, in Claim 1, delete "SEO" and insert --SEQ-- therefor

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*